US011129881B2

(12) United States Patent
Shea et al.

(10) Patent No.: US 11,129,881 B2
(45) Date of Patent: *Sep. 28, 2021

(54) PEPTIDE CONJUGATED PARTICLES

(71) Applicant: Northwestern University, Evanston, IL (US)

(72) Inventors: Lonnie D. Shea, Evanston, IL (US); Stephen D. Miller, Evanston, IL (US); Jonathan Woon Teck Yap, Evanston, IL (US); Daniel R. Getts, Northbrook, IL (US); Derrick McCarthy, Evanston, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/847,450

(22) Filed: Apr. 13, 2020

(65) Prior Publication Data

US 2020/0316181 A1 Oct. 8, 2020

Related U.S. Application Data

(63) Continuation of application No. 15/922,241, filed on Mar. 15, 2018, now Pat. No. 10,617,747, which is a continuation of application No. 15/341,935, filed on Nov. 2, 2016, now Pat. No. 10,188,711, which is a continuation of application No. 14/678,863, filed on Apr. 3, 2015, now Pat. No. 9,522,180, which is a continuation of application No. PCT/US2014/050962, filed on Aug. 13, 2014.

(60) Provisional application No. 61/887,112, filed on Oct. 4, 2013, provisional application No. 61/869,279, filed on Aug. 23, 2013, provisional application No. 61/865,389, filed on Aug. 13, 2013.

(51) Int. Cl.
| | |
|---|---|
| *A61K 39/00* | (2006.01) |
| *A61K 47/69* | (2017.01) |
| *A61K 9/16* | (2006.01) |
| *A61K 9/19* | (2006.01) |
| *A61K 47/58* | (2017.01) |
| *A61K 9/51* | (2006.01) |

(52) U.S. Cl.
CPC ........ *A61K 39/0008* (2013.01); *A61K 9/1647* (2013.01); *A61K 9/19* (2013.01); *A61K 39/00* (2013.01); *A61K 47/58* (2017.08); *A61K 47/6911* (2017.08); *A61K 47/6935* (2017.08); *A61K 47/6937* (2017.08); *A61K 9/5153* (2013.01); *A61K 2039/55555* (2013.01); *A61K 2039/577* (2013.01); *A61K 2039/622* (2013.01)

(58) Field of Classification Search
CPC .................................................. A61K 39/008
See application file for complete search history.

(56) References Cited

U.S. PATENT DOCUMENTS

| | | | |
|---|---|---|---|
| 3,512,940 | A | 5/1970 | Shapiro |
| 4,734,262 | A | 3/1988 | Bagshawe |
| 4,990,253 | A | 2/1991 | Vcelka |
| 5,804,201 | A | 9/1998 | King |
| 5,833,860 | A | 11/1998 | Kopaciewicz et al. |
| 5,871,747 | A | 2/1999 | Gengoux-Sedlik et al. |
| 5,998,214 | A | 12/1999 | Guirguis |
| 6,004,763 | A | 12/1999 | Gengoux et al. |
| 7,829,113 | B2 | 11/2010 | Okada et al. |
| 9,522,180 | B2 | 12/2016 | Shea et al. |
| 9,616,113 | B2 | 4/2017 | Shea et al. |
| 10,617,747 | B2 * | 4/2020 | Shea .................. A61K 47/6911 |
| 2001/0031262 | A1 | 10/2001 | Caplan et al. |
| 2002/0131960 | A1 | 9/2002 | Sadelain et al. |
| 2002/0187147 | A1 * | 12/2002 | Liu .................. C07K 14/70539 |
| | | | 424/144.1 |
| 2003/0166509 | A1 | 9/2003 | Edwards et al. |
| 2004/0043075 | A1 | 3/2004 | Ritter et al. |
| 2004/0072749 | A1 | 4/2004 | Zochoer et al. |
| 2005/0002999 | A1 | 1/2005 | Mehta et al. |
| 2006/0002852 | A1 | 1/2006 | Saltzman et al. |
| 2006/0051407 | A1 | 3/2006 | Richter et al. |
| 2006/0088542 | A1 | 4/2006 | Braun |
| 2007/0014752 | A1 | 1/2007 | Roy et al. |
| 2007/0041934 | A1 | 2/2007 | William et al. |
| 2007/0172653 | A1 | 7/2007 | Berkland et al. |
| 2007/0190160 | A1 | 8/2007 | Turos et al. |
| 2008/0039816 | A1 | 2/2008 | Svarovsky et al. |
| 2008/0124350 | A1 | 5/2008 | Mumper et al. |
| 2008/0207515 | A1 | 8/2008 | Ferguson et al. |
| 2008/0268552 | A1 | 10/2008 | Geiger et al. |
| 2008/0311140 | A1 | 12/2008 | Lee et al. |
| 2009/0123509 | A1 | 5/2009 | Berkland et al. |
| 2009/0214474 | A1 | 8/2009 | Jennings |
| 2009/0304726 | A1 | 12/2009 | Solomon et al. |
| 2009/0325931 | A1 | 12/2009 | Rossi et al. |

(Continued)

FOREIGN PATENT DOCUMENTS

| | | |
|---|---|---|
| DE | 9013914 U1 | 2/1991 |
| EP | 2057998 A1 | 5/2009 |
| EP | 2123261 A1 | 11/2009 |
| EP | 2255831 A1 | 12/2010 |

(Continued)

OTHER PUBLICATIONS

Eldridge et al., Biodegradable microspheres as a vaccine delivery system, Mol. Immunol., 25(3):287-94 (1991).

(Continued)

*Primary Examiner* — Albert M Navarro
*Assistant Examiner* — Mark Navarro
(74) *Attorney, Agent, or Firm* — Marshall, Gerstein & Borun LLP

(57) ABSTRACT

The present invention provides compositions comprising peptide-coupled biodegradable poly(lactide-co-glycolide) (PLG) particles. In particular, PLG particles are surface-functionalized to allow for coupling of peptide molecules to the surface of the particles (e.g., for use in eliciting induction of immunological tolerance).

17 Claims, 54 Drawing Sheets

Specification includes a Sequence Listing.

(56) References Cited

U.S. PATENT DOCUMENTS

| | | |
|---|---|---|
| 2010/0008920 A1 | 1/2010 | Schneck et al. |
| 2010/0015060 A1 | 1/2010 | Baldi et al. |
| 2010/0028450 A1 | 2/2010 | Vasu |
| 2010/0055189 A1 | 3/2010 | Hubbell et al. |
| 2010/0151000 A1 | 6/2010 | Thomas et al. |
| 2010/0256059 A1 | 10/2010 | Johnson et al. |
| 2010/0303850 A1 | 12/2010 | Lipford et al. |
| 2011/0014292 A1 | 1/2011 | O'Hehir et al. |
| 2011/0103588 A1 | 5/2011 | Little et al. |
| 2011/0135666 A1 | 6/2011 | Tedder et al. |
| 2011/0135744 A1 | 6/2011 | Chin et al. |
| 2011/0150987 A1 | 6/2011 | Saint-Lu et al. |
| 2011/0182805 A1 | 7/2011 | Desimone et al. |
| 2011/0206773 A1 | 8/2011 | Lavik et al. |
| 2011/0212172 A1 | 9/2011 | Kellum et al. |
| 2011/0293644 A1 | 12/2011 | Anderson et al. |
| 2012/0076831 A1 | 3/2012 | Miller et al. |
| 2012/0263653 A1 | 10/2012 | Podobinski et al. |
| 2012/0276109 A1 | 11/2012 | Fraser et al. |
| 2012/0276134 A1 | 11/2012 | Fraser et al. |
| 2012/0276155 A1 | 11/2012 | Kishimoto et al. |
| 2012/0276156 A1 | 11/2012 | Fraser et al. |
| 2012/0276157 A1 | 11/2012 | Fraser et al. |
| 2012/0276158 A1 | 11/2012 | Fraser et al. |
| 2012/0276159 A1 | 11/2012 | Fraser et al. |
| 2012/0276160 A1 | 11/2012 | Maldonado |
| 2012/0294888 A1 | 11/2012 | Kishimoto et al. |
| 2012/0301498 A1 | 11/2012 | Altreuter et al. |
| 2012/0301510 A1 | 11/2012 | Kishimoto et al. |
| 2013/0011824 A1 | 1/2013 | Chan et al. |
| 2013/0028941 A1 | 1/2013 | Altreuter et al. |
| 2013/0039954 A1 | 2/2013 | Pittet et al. |
| 2013/0058994 A1 | 3/2013 | Gabivov et al. |
| 2013/0059009 A1 | 3/2013 | Kishimoto et al. |
| 2013/0202659 A1 | 8/2013 | Crawford et al. |
| 2013/0323319 A1 | 12/2013 | Getts et al. |
| 2014/0030344 A1 | 1/2014 | Zepp et al. |
| 2014/0193453 A1 | 7/2014 | Zepp et al. |
| 2014/0199340 A1 | 7/2014 | Maldonado |
| 2014/0242173 A1 | 8/2014 | Zepp et al. |
| 2015/0010631 A1 | 1/2015 | Getts |
| 2015/0174155 A1 | 6/2015 | Getts et al. |
| 2015/0190485 A1 | 7/2015 | Shea et al. |
| 2015/0209293 A1 | 7/2015 | Shea et al. |
| 2016/0166664 A1 | 6/2016 | Miller et al. |
| 2017/0258880 A1 | 9/2017 | Shea et al. |
| 2017/0312349 A1 | 11/2017 | Shea et al. |

FOREIGN PATENT DOCUMENTS

| | | |
|---|---|---|
| JP | H06157592 A | 6/1994 |
| JP | 2009203174 A | 9/2009 |
| JP | 2011-063867 A | 3/2011 |
| JP | 2012504150 A | 2/2012 |
| JP | 2012-505245 A | 3/2012 |
| WO | WO-01/12222 A1 | 2/2001 |
| WO | WO-03/043586 A2 | 5/2003 |
| WO | WO-03/092654 A1 | 11/2003 |
| WO | WO-2004/053056 A2 | 6/2004 |
| WO | WO-2005/015160 A2 | 2/2005 |
| WO | WO-2007/087341 A2 | 8/2007 |
| WO | WO-2008/109852 A2 | 9/2008 |
| WO | WO-2009/051837 A2 | 4/2009 |
| WO | WO-2009/052561 A1 | 4/2009 |
| WO | WO-2009/056332 A1 | 5/2009 |
| WO | WO-2009/108686 A1 | 9/2009 |
| WO | WO-2010/025324 A2 | 3/2010 |
| WO | WO-2010/060155 A1 | 6/2010 |
| WO | WO-2010/066049 A1 | 6/2010 |
| WO | WO-2010/085509 A1 | 7/2010 |
| WO | WO-2011/031441 A1 | 3/2011 |
| WO | WO-2011/103588 A1 | 8/2011 |
| WO | WO-2011/133617 A1 | 10/2011 |
| WO | WO-2011/150573 A1 | 12/2011 |
| WO | WO-2011/153532 A1 | 12/2011 |
| WO | WO-2012/001647 A2 | 1/2012 |
| WO | WO-2012/018380 A2 | 2/2012 |
| WO | WO-2012/019041 A2 | 2/2012 |
| WO | WO-2012/065153 A2 | 5/2012 |
| WO | WO-2012/071014 A1 | 5/2012 |
| WO | WO-2012/101638 A2 | 8/2012 |
| WO | WO-2012/116282 A2 | 8/2012 |
| WO | WO-2012/149252 A2 | 11/2012 |
| WO | WO-2012/149255 A2 | 11/2012 |
| WO | WO-2012/149411 A1 | 11/2012 |
| WO | WO-2012/149454 A2 | 11/2012 |
| WO | WO-2013/113501 A1 | 8/2013 |
| WO | WO-2013/192532 A2 | 12/2013 |
| WO | WO-2014/160465 A2 | 10/2014 |
| WO | WO-2015/023796 A2 | 2/2015 |

OTHER PUBLICATIONS

Akagi et al., Biodegradable nanoparticles as vaccine adjuvants and delivery systems: Regulation of immune responses by nanoparticle-based vaccine, IN: Bioactive Surfaces, vol. 247, pp. 31-64 (2011).

Batanero et al., "Biodegradable poly (DL-lactide glycolide) microparticles as a vehicle for allergenspecific vaccines: a study performed with Ole e 1, the main allergen of olive pollen," J. Immunol. Meth. 259:87-94 (2002).

Battaglia, et al. Rapamycin and Interleukin-10 Treatment Induces T Regulatory Type 1 Cells That Mediate Antigen-Specific Transplantation Tolerance, Diabetes. Jan. 2006, vol. 55, pp. 40-49.

Chang et al., Functionalized nanoparticles provide early cardioprotection after acute myocardial infarction, J. Control. Rel., 180:287-94 (2013).

Chauhan, et al. "Unexpected in Vivo Anti-Inflammatory Activity Observed for Simple, Surface Functionalized Poly(amidoamine) Dendrimers." Biomacromolecules. Apr. 6, 2009, vol. 10, pp. 1195-1202.

Ciccocioppo et al., The immune recognition of gluten in coeliac disease, Clin. Exp. Immunol., 140(3):408-16 (2005).

Cour Pharmaceuticals Development Company et al., "Immune-Modifying Particles for the Treatment of Ebola Virus," PCT Appl. No. PCT/US2015/054922, 52 pages (filed Oct. 9, 2015).

Danhier et al., PLGA-based nanoparticles: an overview of biomedical applications, J. Control. Release, 161(2):505-22 (2012).

Dobrovolskaia and McNeil, "Immunological properties of engineered nanornaterials," Nat. Nanotechnol. 2:469-478 (2007).

Dolgin, "The inverse of immunity," Nature Medicine. 2010; 16(7):740-743.

Eagar, et al. CTLA-4 regulates expansion and differentiation of Th1 cells following induction of peripheral T cell tolerance, J. Immunol., 172(12):7442-50 (Jun. 2004).

Eagar, et al. The role ofCTLA-4 in induction and maintenance of peripheral T cell tolerance. Eur J Immunol. Apr. 2002;32(4):972-81.

Elamanchili et al., "Pathogen-mimicking" nanoparticles for vaccine delivery to dendritic cells, J. Immunother., 30(4):378-95 (2007).

European Patent Application No. 14836306.2, Communication pursuant to Article 94(3) EPC, dated May 3, 2018.

European Patent Application No. 14836306.2, Extended European Search Report, dated Feb. 20, 2017.

Fife, et al. Insulin-induced remission in new-onset NOD mice is maintained by the PD-1-PD-L1 pathway, J. Exp. Med., 203(12):2737-47 (Nov. 2006).

Frohlich, et al., "The Role of Surface Charge in Cellular Uptake and Cytotoxicity of Medical Nanoparticles," International Journal of Nanomedicine, 7(31):5577, Oct. 2012.

Getts et al., "Current landscape for T-cell targeting in autoimmunity and transplantation," Immunotherapy. Jul. 2011;3 (7): 853-70.

Getts et al., "Microparticles bearing encephalitogenic peptides induce T-cell tolerance and ameliorate experimental autoimmune encephalomyelitis", Nature Biotechnol, 30:1217-1224 (2012).

Getts, D.R., et al., "Therapeutic Inflammatory Monocyte Modulation Using Immune-Modifying Microparticles," Science Trans. Med. 2014;6(219):1-14.

(56) References Cited

OTHER PUBLICATIONS

Getts, et al. Differential outcome of tolerance induction in naive versus activated Theiler's virus epitope-specific CD8+ cytotoxic T cells. J Virol. Jun. 2007;81(12):6584-93. Epub Apr. 11, 2007.

Getts, et al. Tolerance induced by apoptotic antigen-coupled leukocytes is induced by PD-L11+ and IL-10-producing splenic macrophages and maintained by T regulatory cells. J Immunol. 2011.

Gondeau, et al. "Design of a novel class of peptide inhibitors of cyclin-dependent kinase/cyclin 38-40 activation," J Biol Chem. Jan. 13, 2005, vol. 80, pp. 13793-13800.

Gulfam et al., Anticancer drug-loaded gliadin nanoparticles induce apoptosis in breast cancer cells, Langmuir, 28(21):8216-23 (2012).

Hacker et al., "Pathogenicity and Epitope Characteristics of Anti-Desmoglein-1 from Pernphigus Foliaceus Patients Expressing Only IgG I Autoantibodies," J invest Dermatol 121(6):1373-1378 (2003).

Hamdy et al., Co-delivery of cancer-associated antigen and Toll-like receptor 4 ligand in PLGA nanoparticles induces potent CD8+ T cell-mediated anti-tumor immunity, Vaccine, 26(39):5046-57 (2008).

Honary et al., Effect of zeta potential on the properties of nano-drug delivery systems—a review (Part 2), Trop. J. Pharm. Res., 12(2):265-73 (2013).

Hsu et al., "IL-33 Is Produced by Mast Cells and Regulates IgE Dependent Inflammation," PLoS One, 5(8):e11944 (Aug. 2010).

Hunter et al., "A Biodegradable Nanoparticle Platform for the Induction of Antigen-Specific Immune Tolerance for Treatment of Autoimmune Disease," ACS Nano 8(3):2148-2160 (2014).

International search report and written opinion dated Jan. 10, 2014 for PCT Application No. PCT/US2013/044616, 21 pages.

International search report and written opinion dated Mar. 2, 2010 for PCT/US2010/021547, authored by Lee W. Young, published by International Search Authority/US in the United States, 7 pages.

International Search Report for PCT/US2011/060537 dated Feb. 20, 2013, 3 pages.

International Search Report for PCT/US2013/047079 dated Jan. 17, 2014, 3 pages.

International Search Report for PCT/US2014/026719 dated Sep. 26, 2014, 7 pages.

International Search Report for PCT/US2014/050962 dated Mar. 20, 2015, 6 pages.

Japanese Patent Application No. 2016-534825, Notice of Reasons for Rejection, dated Apr. 26, 2018.

Jilek, et al. "Modulation of allergic responses in mice by using biodegradable poly(lactide-co-glycolide) microspheres" J Allergy Clin Immunol 2004, vol. 114: 943-950 Available online Aug. 3, 2004.

Kanno et al., "A Murine Scavenger Receptor MARCO Recognizes Polystyrene Nanoparticles," Toxicol Sci. Jun. 2007;97(2):398-406. Epub Mar. 14, 2007.

Keijzer, et al. "PLGA, PLGA-TMC and TMC-TPP Nanoparticles Differentially Modulate the Outcome of Nasal Vaccination by Inducing Tolerance or Enhancing Humoral Immunity," PLOS One Nov. 2, 2011, vol. 6(11) e26684.

Kennedy et al., "Induction of antigen-specific tolerance for the treatment of ongoing, relapsing autoimmune encephalomyelitis: a comparison between oral and peripheral tolerance," J. Immunol. 159(2):1036-1044 (1997).

Kim et al., Albumin-Coated Porous Hollow Poly(Lactic-co-Glycolic Acid) Microparticles Bound with Palmityl-Acylated Exendin-4 as a Long-Acting Inhalation Delivery System for the Treatment of Diabetes, Pharm. Res. 28:2008-2019 (2011).

Kim, et al. "Suppression of Collagen-Induced Arthritis by Single Administration of Poly(Lactic-Co-Glycolic Acid) Nanoparticles Entrapping Type II Collagen," Arthritis & Rheumatism vol. 46(4), Apr. 2002, pp. 1109-1120.

Lamprecht et al., "Biodegradable Nanoparticles for Targeted Drug Delivery in Treatment of Inflammatory Bowel Disease," J. Pharmacol. Exp. Therapeutics 299(2):775-781 (2001).

Latch Man, et al. PD-L1-deficient mice show that PD-L1 on T cells, antigen-presenting cells, and host tissues negatively regulates T cells. Proc Natl Acad Sci USA. Jul. 20, 2004;101(29):10691-6. Epub Jul. 12, 2004.

León-Rodriguez et al., Incorporation of PVMMA to PLGA MS enhances lectin grafting and their in vitro activity in macrophages, Int. J. Pharm., 402(1-2):165-74 (2010).

Liu et al., "Biocompatible and detectable caiboxylated nanodiamond on human cell," Nanotechnol. 18(32):325102, 10 pages (2007).

Lo et al., "Simultaneous release of multiple molecules from poly(lactide-co-glycolide) nanoparticles assembled onto medical devices", Biomaterials, 30: 4889-4897 (2009).

Lunov et al., "The effect of carboxydextran-coated superparamagnetic iron oxide nanoparticles on cJun N-terrninal kinase-mediated apoptosis in human macrophages," Biomaterials 31:5063-5071 (2010).

Luo et al., "ECDI-fixed allogeneic splenocytes induce donor-specific tolerance for long-term survival of islet transplants via two distinct mechanisms," Proc. Natl. Acad. Sci. USA 105(38):14527-14532 (2008).

Lutsiak et al., Biodegradable nanoparticle delivery of a Th2-biased peptide for induction of Th1 immune responses, J. Pharm. Pharmacol., 58(6):739-47 (2006).

Manish et al., A single-dose PLGA encapsulated protective antigen domain 4 nanoformulation protects mice against Bacillus anthracis spore challenge, PLoS One, 8(4):e61885 (2013).

Marazeuela E. G. et al., "Intranasal vaccination with poly(lactide-co-glycolide) microparticles containing a peptide T of Ole e 1 prevents mice against sensitization", Clinical and Experimental Allergy, vol. 38, 2008, pp. 520-528.

Martin, et al. Ethylenecarbodiimide-treated splenocytes carrying male CD4 epitopes confer histocompatibility Y chromosome antigen transplant protection by inhibiting CD154 upregulation. J immunol. Sep. 15, 2010;185(6):3326-36. Epub Aug. 16, 2010.

McCauley, et al., "Comprehensive Follow-Up of the First Genome-Wide Association Study of Multiple Sclerosis Identifies KIF21 B and TMEM39A as Susceptibility Loci, The International Multipke Sclerosis Genetics Consortium (IMSGC)," Human Molecular Genetics, 19(5):953-962, 2010.

McRae, et al. Functional evidence for epitope spreading in the relapsing pathology of experimental autoimmune encephalomyelitis. J Exp Med. Jul. 1, 1995;182(1):75-85.

Merodio, et al. Distribution of albumin nanoparticles in animals induced with the experimental allergic encephalomyelitis. J Drug Target. 2000; 8(5):289-303.

Miller et al., "The induction of cell-mediated immunity and tolerance with protein antigens coupled to syngeneic lymphoid cells," J. Exp. Med. Mar. 1, 1979;149(3):758-73.

Muller et al., Surface modification of PLGA microspheres, J. Biomed. Mater. Res., 66A:55-61 (2003).

Muthu, "Nanoparticles based on PLGA and its co-polymer: An overview," Asian J. Pharm. 3(4):266-273 (2009).

Nakajima et al., Mechanism of amide formation by carbodiimide for bioconjugation in aqueous media, Bioconjug. Chem., 6(1):123-30 (Jan.-Feb. 1995).

Nygaard, U et al. "The Allergy Adjuvant Effect of Particles—Genetic Factors Influence Antibody and Cytokine Responses." BMC Immunology. Jun. 21, 2005, vol. 6, pp. 1-10.

Orecchioni et al., Gliadin characterization by SANS and gliadin nanoparticle growth modelization, J. Nanosci. Nanotechnol., 6(9-10):3717-8 (2006).

Pawar et al., Evaluation of mucoadhesive PLGA microparticles for nasal immunization, AAPS J., 12(2):130-7 (2010).

Payne et al., "Genetic and functional characterization of human pemphigus vulgaris monoclonal autoantibodies isolated by phage display," J. Cliff. Invest. 115(4): 888-899 (2005).

Pecquet, et al. "Oral tolerance elicited in mice by b-lactoglobulin entrapped in biodegradable microspheres," Vaccine 2000 vol. 18: 1196-1202.

Peterson, et al. Split tolerance of Th1 and Th2 cells in tolerance to Theiler's murine encephalomyelitis virus. Eur J Immunol. Jan. 1993; 23(1):46-55.

(56) References Cited

OTHER PUBLICATIONS

Prasad et al., Tolerance strategies employing antigen-coupled apoptotic cells and carboxylated PLG nanoparticles for the treatment of type 1 diabetes, Rev. Diabet. Stud., 9(4):319-27 (2012).
Russian Patent Application No. 2016107998, Office English (English translation), dated Apr. 18, 2018.
Sahoo et al., "Residual polyvinyl alcohol associated with poly (D,L-lactide-co-glycolide) nanoparticels affects their physical properties and cellular uptake," J. Control. Rel. 82:105-114 (2002).
Saint-Lu et al., "Targeting the allergen to oral dendritic cells with mucoadhesive chitosan particles enhances tolerance induction," Allergy 64(7):1003-1013 (2009).
Salvador-Morales et al., "Immunocompatibility properties of lipid-polymer hybrid nanoparticles with heterogeneous surface functional groups," Biomaterials 30:2231-2240 (2009).
Sampson and Armbrustntacher. "West Nile Encephalitis: The Neuropathology of Four Fatalities," Ann. N.Y. Acad. Sci. 951:172-178 (2001).
Schmidt et al., "Glucocorticoids Induce Apoptosis in Human Monocytes: Potential Role of IL-10," J. Inmiunol. 163:3484-3490 (1999).
Schrand et al., "Nanodiamond Particles: Properties and Perspectives for Bioapplications," Critical Reviews in Solid State and Materials Sciences, 34:18-74, 2009.
Sekiguchi et al., "Dominant Autoimmune Epitopes Recognized by Pemphigus Antibodies Map to the N-Terminal Adhesive Region of Desmogleins," The Journal of Immunology 167:5439-5448 (2001).
Senger et al., Identification of immunodominant epitopes of alpha-gliadin in HLA-DQ8 transgenic mice following oral immunization, J. Immunol., 175(12):8087-95 (2005).
Slütter et al., Nasal vaccination with N-trimethyl chitosan and PLGA based nanoparticles: nanoparticle characteristics determine quality and strength of the antibody response in mice against the encapsulated antigen, Vaccine, 28(38):6282-91 (2010).
Smarr et al., Biodegradable antigen-associated PLG nanoparticles tolerize Th2-mediated allergic airway inflammation pre- and postsensitization, Proc. Natl. Acad. Sci. USA, 113(18):5059-64 (2016).
Smith, et al. Epitope spread is not critical for the relapse and progression of MOG 8-21 induced EAE in Biozzi ABH mice. J Neuroimmunol. Jul. 2005; 164(1-2):76-84.
Sollid et al. "Nomenclature and listing of celiac disease relevant gluten T-cell epitopes restricted by HLA-DQ molecules," Immunogenetics 2012 vol. 64: 455-460. Published online: Feb. 10, 2012.
Supplementary European Search Report, EP appl. No. 10733824.6, 11 pages (dated Jul. 11, 2012).
Supplementary European Search Report, EP appl. No. 13807832.4, 11 pages (dated Mar. 31, 2016).
Supplementary European Search Report, EP appl. No. 14773771.2, 9 pages (dated Sep. 5, 2016).
Supplementary European Search Report, European patent application No. 14836306, dated Feb. 13, 2017.
Supplementary European Search Report. EP appl. No. 11839890.8, 8 pages (dated Jun. 15, 2016).
TSE, "Particulate promotion of tolerance", Nature Rev Drug Discovery, 12: 22-23 (2013).
Turley et al., "Peripheral tolerance induction using ethylenecarbodiimide-fixed APCs uses both direct and indirect mechanisms of antigen presentation for prevention of experimental autoimmune encephalomyelitis," J. Immunol 178(4):2212-2220 (2007).
Waeckerle-Men et al., Encapsulation of proteins and peptides into biodegradable poly(D,L-lactide-co-glycolide) microspheres prolongs and enhances antigen presentation by human dendritic cells, Vaccine, 24(11):1847-57 (2006).
Written Opinion of the International Searching Authority, PCT Appl. No. PCT/US2013/047079, 7 pages (dated Jan. 17, 2014).
Written Opinion of the International Searching Authority, PCT Appl. No. PCT/US2014/050962, 15 pages (dated Mar. 20, 2015).
Zolnik, et al. Nanoparticles and the immune system. Endocrinology. Feb. 2010; 151(2):458-65. doi: 10.1210/en.2009-1082. Epub Dec. 16, 2009.
Sharif et al., Biodegradable microparticles as a delivery system for the allergens of Dermatophagoides pteronyssinus (house dust mite): I. Preparation and characterization of microparticles, Int. J. Pharm., 119(2):239-46 (Jun. 1995).
Keegan et al., Biodegradable Microspheres with Enhanced Capacity for Covalently Bound Surface Ligands, Macromolecules, 37(26):9779-84 (2004).
Keegan, A Dissertation Presented to the Faculty of the Graduate School of Cornell University in Partial Fulfillment of the Requirements for the Degree of Doctor of Philosophy, May 2004.
Pearson et al., Overcoming Challenges in Treating Autoimmuntity: Development of Tolerogenic Immune-Modifying Nanoparticles, Nanomedicine, 18:282-291 (Jun. 2019).
Marin et al., Critical evaluation of biodegradable polymers used in nanodrugs, Int. J. Nanomedicine, 8(1):3071-3091 (2013).
Ojala et al., Crystal Structure of the Cysteine-Rich Domain of Scavenger Receptor MARCO Reveals the Presence of a Basic and an Acidic Cluster That Both Contribute to Ligand Recognition, J. Biol. Chem., 282(22):16654-66 (Jun. 2007).
Mukhopadhyay et al., MARCO, an Innate Activation Marker of Macrophages, Is a Class a Scavenger Receptor for Neisseria Meningitidis, Eur. J. Immunol., 36(4):940-9 (Apr. 2006).

\* cited by examiner

FIG. 1A
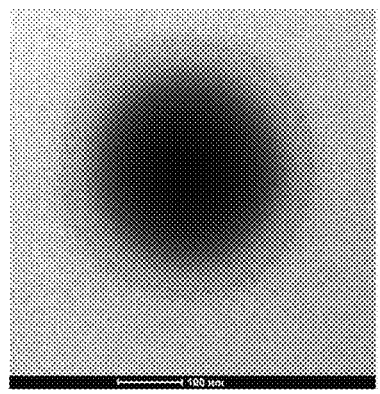
FIG. 1B
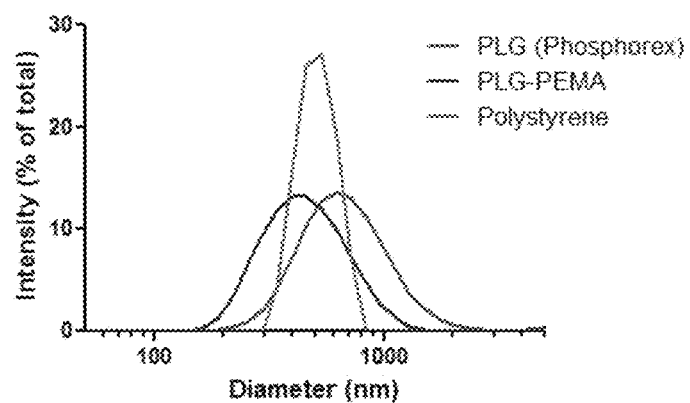
FIG. 1C
| Particle | Z-average size by intensity (nm) | ζ-potential (mV) | PLP(139-151) Coupling Efficiency (%) | OVA(323-339) Coupling Efficiency (%) |
|---|---|---|---|---|
| PLG (Phosphorex) | 624.3 | -32.7 ± 4.71 | 3.75 ± 0.25 | 3.12 ± 0.02 |
| PLG-PEMA | 429.9 | -67.4 ± 10.9 | 10.61 ± 0.29 | 9.37 ± 0.01 |
| Polystyrene | 503.6 | -66.4 ± 6.97 | 61.96 ± 5.79 | 29.53 ± 1.19 |

Change in Body Temperature Following Treatment

** 3 out of 6 mice in the soluble PLP139 group died before 60 minute time point. The remaining 3 had temperatures that began increasing after 50 minutes, and were able to restabilize.

Tolerize Day +21, $PLP_{139-151}$/CFA Active Disease

Cat B Brain

Cat B Spinal Cord

AngioSense Brain

AngioSense Spinal Cord

Day + 14 Therapeutic Tolerance, Adoptive Transfer Disease

Day + 18 (remission) tolerance, $PLP_{178}$/CFA, Active Disease

Active EAE Onset

Adoptive EAE Onset

Microglia

Macrophages pDCs

CD11b+ DCs

PEPTIDE CONJUGATED PARTICLES

RELATED APPLICATIONS

The application claims priority to U.S. Provisional Patent Application No. 61/865,389, filed Aug. 13, 2013, U.S. Provisional Patent Application No. 61/869,279, filed Aug. 23, 2013 and U.S. Provisional Patent Application No. 61/887,112, filed Oct. 4, 2013. This application is also related to PCT Application No. PCT/US2013/047079 filed Jun. 21, 2013 which claims priority to U.S. Provisional Application No. 61/662,687, filed Jun. 21, 2012. The contents of each of which is hereby incorporated by reference in its entirety.

FEDERAL SUPPORT

This invention was made with government support under R01 EB013198 awarded by the National Institutes of Health. The government has certain rights in this invention.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: COUR-002_01US_Seqlist.txt, date recorded: Aug. 13, 2013, file size 1.17 megabytes).

BACKGROUND OF INVENTION

Inflammatory diseases and disorders are conditions in which an abnormal or otherwise deregulated inflammatory response contributes to the etiology or severity of disease. Examples include autoimmune diseases such as type 1 diabetes and Celiac disease.

Many of these diseases are characterized by a mononuclear cell infiltration at a site of tissue injury or other insult. Examples of mononuclear cells that have been observed in these infiltrations include lymphocytes, especially T lymphocytes, and cells of the mononuclear phagocyte system (MPS cells) such as monocytes, macrophages, dendritic cells, microglial cells and others.

Many of the cells observed in the mononuclear cell infiltrates are suspected of having a role in these abnormal inflammatory responses. For example, in diseases such as multiple sclerosis, CD4$^+$ T cells are known to play a central role in the pathologic autoimmune response. At an earlier time point in T cell activation, dendritic cells and other MPS cells may be responsible for activation of CD4$^+$ T cells. MPS cells could also contribute to inflammation through phagocytosis although in at least some inflammatory diseases it is not clear whether such cells would be capable of this in the absence of CD4$^+$ T cells.

Peripheral blood monocytes may be classified into one of two groups according to the expression or not of certain cell surface molecules. In particular, human "resident monocytes" or "mature monocytes" are understood to have a CD14$^{lo}$CD16$^+$ phenotype (the mouse counterpart is CX$_3$CR1$^{hi}$CCR2$^-$Gr1$^-$). Another group of cells, the "inflammatory monocytes" or "immature monocytes" are understood to have a CD14$^+$CD16$^-$ phenotype (the mouse counterpart is CX$_3$CR1$^{lo}$CCR2$^+$Gr1$^+$). (Geissmann F. et al. 2003 Immunity 19: 71-82)

Importantly, while the latter are understood to be "inflammatory" in the sense that they are observed to migrate into inflamed tissue from bone marrow derived peripheral blood cells, these cells have not been shown to cause inflammation either directly or through the action of other cells. Further, the various MPS cells that may be formed when these cells differentiate have also not been shown to cause inflammation.

Conventional clinical strategies for general long-term immunosuppression in disorders associated with an undesired immune response are based on the long-term administration of broad acting immunosuppressive drugs, for example, signal 1 blockers such as cyclosporin A (CsA), FK506 (tacrolimus) and corticosteroids. Long-term use of high doses of these drugs can have toxic side-effects. Moreover, even in those patients that are able to tolerate these drugs, the requirement for life-long immunosuppressive drug therapy carries a significant risk of severe side effects, including tumors, serious infections, nephrotoxicity and metabolic disorders.

Methods of inducing antigen-specific tolerance have been developed, including cell coupling of an antigen or peptide. For example, in one method, peptide induced cell coupled tolerance involved collection, separation and treatment of peripheral blood cells with disease specific autoantigens and the ethylene carbodimide (ECDI) coupling reagent under sterile conditions, and subsequent re-infusion into the donor/patient. This process is costly and must be conducted under closely monitored conditions by skilled practitioners and is limited in the number of centers that can conduct the procedure. The use of red blood cells as the donor cell type expands the potential source to include allogeneic donors thus increasing the supply of source cells dramatically and potentially expanding the delivery of this therapy to any setting certified for blood transfusion. These approaches have significant limitations in terms of supply of source cells and necessity for tissue type matching to minimize immune response to the donor cells. In addition the local treatment of the cells to couple autoantigens via EDCI presents a significant quality control issue. Furthermore, these approaches also require at least some knowledge of the pathological antigen for which immune tolerance is sought.

Recently, peptide-coupled particles have been described which eliminates the requirement for a supply of source cells and circumvents the tissue-typing requirement of the prior approaches, See WO 2010/085509, incorporated by reference herein in its entirety. Not withstanding, the use of antigens coupled to the outside of particles is associated with increased anaphylaxis and has significant chemistry, manufacturing and control issues. Surprisingly, when the antigen is encapsulated within the particle, these adverse events are avoided. Even more surprisingly, the size and the charge can be altered to enhance tolerance to specific antigens.

Antigen-specific tolerance is generally not ideal because specific antigens/epitopes are generally not known in human diseases. Furthermore, antigens can vary from subject to subject in order for an antigen specific approach to be effective, therefore it would be necessary to determine which antigens each individual patient would recognize, or it would require coupling a library of possible peptides to the particles prior to administration. The synthesis and individual coupling of these peptides is both time consuming and expensive. Therefore, a need exists for a therapy which solves both of these problems thereby eliminating the need to for a source of tissue matched cells.

SUMMARY OF THE INVENTION

In some embodiments, the present invention provides compositions (e.g., for induction of antigen-specific tolerance) comprising a carrier particle (e.g., PLG particle) attached to an antigenic peptide. In certain embodiments, the carrier particle is a poly(lactide-co-glycolide) (PLG) particle. In other embodiments, the carrier particle is a PLURIONICS® stabilized polypropylene sulfide particle.

In some embodiments, the present invention provides compositions comprising: an antigen coupled to a carrier particle with a negative zeta potential. In some embodiments, the zeta potential of the particle is from about −100 mV to about 0 mV. In some embodiments, the zeta potential of the particle is from about −50 mV to about −40 mV. In some embodiments, the particle is a co-polymer having a molar ratio from about 50:50, 80:20 to about 100:0. In some embodiments, the co-polymers ratio may be, but not limited to, polystyrene:poly(vinyl carboxylate)/80:20, polystyrene:poly(vinyl carboxylate)/90:10, poly(vinyl carboxylate):polystyrene/80:20, poly(vinyl carboxylate):polystyrene/90:10, polylactic acid:polyglycolic acid/80:20, or polylactic acid:polyglycolic acid/90:10, or polylactic acid:polyglycolic acid/50:50. Yet in other embodiments, the particle is a polystyrene particle, a carboxylated polysterene particle, PLURIONICS® stabilized polypropylene sulfide particle, or a poly(lactic-co-glycolic acid) particle. In some embodiments, the particle is a poly(lactic-co-glycolic acid) particle.

In some embodiments, the particle has an average diameter of between about 0.1 µm to about 10 µm. In some embodiments, the particle has an average diameter of between 0.2 µm and about 2 µm. In some embodiments, the particle has a diameter of between about 0.3 µm to about 5 µm. In some embodiments, the particle has a diameter of between about 0.5 µm to about 3 µm. In some embodiments, the particle has a diameter of between about 0.5 µm to about 1 µm. In some embodiments, the particle has a diameter of about 0.5 µm.

In further embodiments, the antigen comprises at least a portion of an autoimmune antigen, an antigen expressed on a tissue to be transplanted into a subject, an enzyme, or an allergen. In some embodiments, the antigen comprises at least a portion of myelin basic protein, acetylcholine receptor, endogenous antigen, myelin oligodendrocyte glycoprotein, pancreatic beta-cell antigen, insulin, proinsulin, islet-specific glucose-6-phophatase catalytic subunit-related protein (IGRP), glutamic acid decarboxylase (GAD), collagen type 11, human cartilage gp39, fp130-RAPS, proteolipid protein, fibrillarin, small nucleolar protein, thyroid stimulating factor receptor, histones, glycoprotein gp70, pyruvate dehydrogenase dehydrolipoamide acetyltransferase (PCD-E2), hair follicle antigen, aqua porin 4, Desmoglein 1, Desmoglein 3, nicotinic acetylcholine receptor, A-gliaden, and human tropomyosin isoform 5, Bahia grass pollen (BaGP), peach allergen Pru p 3, alpha s 1-Caein Milk allergen, Apig1 celery allergen, Bere1 Brazil nut allergen, B-Lactoglobulin Milk allergen, Bovine serum albumin, Cor a 1.04 Hazelnut allergen, Ovalbumin Egg allergen, Advate, antihemophilic factor, Kogenate, Eloctate, recombinant factor VIII Fc fusion protein, Refacto, Novo VIIa, recombinant factor VII, eptacog alfa, Helixate, Monanine, Coagulation Factor IX, Wilate, Ceredase, Alglucerase, Cerezyme, Imiglucerase, Elelso, taliglucerase alfa, Fabrazyme, Agalsidase beta, Aldurazyme, -I-iduronidase, Myozyme, Acid-glucosidase, Elaprase, iduronate-2-sulfatase, Naglazyme arylsufatase B, or N-acetylgalactosamin e-4-sulfatase, proteinaceous therapies used in enzyme or coagluation factor replacement such as myozyme, alglucerase, imiglucerase, taliglucerase, agalsidase beta, 1-iduronidase, acid glucosidase, Iduronate-2-sulfatase, N-acetylgalactosamnie-4-sulfatase, antihemophilic factor, factor VII, eptacogalfa, factor IX, miglustat, romiplastim, epotetin alpha, protein C, laronidase, lumizyme or Factor VIII.

In further embodiments, the antigen comprises an autoimmune antigen, an antigen expressed on a tissue to be transplanted into a subject, an enzyme, or an allergen. In non-limiting embodiments, the antigen comprises, for example, myelin basic protein, acetylcholine receptor, endogenous antigen, myelin oligodendrocyte glycoprotein, pancreatic beta-cell antigen, insulin, glutamic acid decarboxylase (GAD), collagen type 11, human cartilage gp39, fp130-RAPS, proteolipid protein, fibrillarin, small nucleolar protein, thyroid stimulating factor receptor, histones, glycoprotein gp70, pyruvate dehydrogenase dehydrolipoamide acetyltransferase (PCD-E2), hair follicle antigen, aqua porin 4, Desmoglein 1, Desmoglein 3, nicotinic acetylcholine receptor, A-gliaden, and human tropomyosin isoform 5, Bahia grass pollen (BaGP), peach allergen Pru p 3, alpha s 1-Caein Milk allergen, Apig1 celery allergen, Bere1 Brazil nut allergen, B-Lactoglobulin Milk allergen, Bovine serum albumin, Cor a 1.04 Hazelnut allergen, insulin, proinsulin, islet-specific glucose-6-phophatase catalytic subunit-related protein (IGRP), Ovalbumin Egg allergen, proteinaceous therapies used in enzyme or coagluation factor replacement such as myozyme, alglucerase, imiglucerase, taliglucerase, agalsidase beta, 1-iduronidase, acid glucosidase, Iduronate-2-sulfatase, N-acetylgalactosamnie-4-sulfatase, antihemophilic factor, factor VII, eptacogalfa, factor IX, miglustat, romiplastim, epotetin alpha, protein C, laronidase, lumizyme Factor VIII.

In further embodiments, the particles are coupled to an antigen comprising one or more epitopes. In a further embodiment, the epitope is associated with an allergy, an autoimmune disease, an enzyme used in enzyme replacement therapy, lysosomal storage disease, or an inflammatory disease or disorder. In one embodiment, the epitope is associated with type 1 diabetes, multiple sclerosis, Systemic Lupus, Neuromyelitis Optica, Idiopathic Thrombocytopenic Purpura, Thrombotic Thrombocytopenic Purpura, Membranous Nephropathy, Bullous Phemphigoid, Phemphigus Vulgaris, Myasthenia Gravis, a mucopolysaccharide storage disorder, gangliosidosis, alkaline hypophosphatasia, cholesterol ester storage disease, hyperuricemia, growth hormone deficiency, renal anemia, Gaucher's disease, Fabry's disease, Hurler's disease, Hunter's disease, Maroteaux-Lamy disease, hemophilia A, hemophilia B, von Wilebrand disease, venous thrombosis, purpura fulminans, mucopolysaccaridosis VI, pompe disease, Celiac's disease, or inflammatory bowel disease, including Crohn's disease or colitis, e.g. ulcerative colitis. In a further embodiment the epitopes are found within proteinaceous therapies used in enzyme or coagluation factor replacement such as myozyme, alglucerase, imiglucerase, taliglucerase, agalsidase beta, 1-iduronidase, acid glucosidase, Iduronate-2-sulfatase, N-acetylgalactosamnie-4-sulfatase, antihemophilic factor, factor VII, eptacogalfa, factor IX, miglustat, romiplastim, epotetin alpha, protein C, laronidase, lumizyme Factor VIII. In a further embodiment, the epitope is an epitope described in Tables 2 or 3. In one embodiment, the particles are coupled to antigens comprising only one epitope associated with one disease and/or disorder. In a further embodiment, antigens comprise more than one epitope associated with the same disease and/or disorder. In a further embodiment, the antigens comprise more than one epitope associated with different diseases and/or disorders.

In some embodiments, the antigen is coupled to said particle by a conjugate molecule. In some embodiments, the antigen is coupled to said particle by a linker. In some embodiments, the conjugate molecule is ethylene carbodiimide (ECDI). In certain embodiments, the antigen is linked by a streptavidin-biotin complex. In some embodiments, the linkers can include, but are not limited to, a variety of bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis-(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particular coupling agents include N-succinimidyl-3-(2-pyridyldithio)propionate (SPDP) and N-succinimidyl-4-(2-pyridylthio)pentanoate (SPP) to provide for a disulfide linkage.

In some embodiments, the antigen is coupled to the outside of the particle with a negative zeta potential. In some embodiments, the antigen is encapsulated in the particle which has a negative surface zeta potential. In some embodiments, the particle is biodegradable. In some embodiments, the particle is surface functionalized. In some embodiments, the particle is carboxylate surface functionalized.

In some embodiments, the present invention provides methods of inducing antigen-specific tolerance in a subject comprising: administering to said subject an effective amount of a composition comprising an antigen-coupled particle to said subject, wherein said particle has a negative zeta potential, and wherein said particle and antigen induce tolerance of said antigen in said subject. In some embodiments, administering is performed to treat or prevent a disease or condition. In some embodiments, administering is performed prior or subsequent to onset of a disease or condition that is caused by said antigen. In some embodiments, the disease or condition is selected from the group consisting of: an autoimmune disease, inflammatory disease, an allergy, transplantation rejection, a lysosomal storage disease, an enzyme deficiency, inflammatory response and a hyperimmune response. In some embodiments, the disease or condition is selected from the group consisting of: multiple sclerosis, type 1 diabetes, asthma, a food allergy, an environmental allergy, Celiac disease, inflammatory bowel disease, including Crohn's disease or ulcerative colitis, and a condition caused by said antigen in said subject to reduce overreaction to said antigen. In some embodiments, methods further comprise repeating said administration of said composition into said subject.

In a further embodiment, the administration of the particles results in activation induced death of effector T cells.

In a further embodiment, the administration of the particles results in anergy of effector T cells.

In a further embodiment, the administration of particles results in apoptosis of effector T cells.

In a further embodiment, the administration of particles results in the conversion of effector T cells to regulatory T cells.

In a further embodiment, the administration of particles results in the induction and expansion of both antigen specific and non-specific regulatory T cells. In a further embodiment, the administration of particles results in the isolation of effector T cells in the lymph nodes and spleen inhibiting their ability to traffic to peripheral sites and cause inflammation.

In a further embodiment, the administration of particles results in the down regulation of T cell dependent antibody production.

In certain embodiments, the present invention provides methods for treating celiac disease in a subject comprising administering to said subject an effective amount of a composition comprising an antigen-coupled particle to the subject, wherein the particle has a negative zeta potential. In certain embodiments, the antigen is gliaden or a gliaden epitope. In some embodiments, the antigen is one or more antigens selected from the group consisting of SEQ ID NOs: 1295-1724, SEQ ID NOs: 1726-1766 and SEQ ID NOs: 4986-5140. In some embodiments, the antigen is gliaden and the antigen-coupled particle has a post-synthesis average size of about 600-1500 nanometers and a post-synthesis average charge of about −30 to about −80 mV. In some embodiments, the particle has a post-synthesis average size of about 600-1200 nanometers and a post-synthesis average charge of about −40 to about −70 mV. In certain embodiments, the particle has a post-synthesis average size of about 600 microns and a post-synthesis average charge of about −50 mV. In further embodiments, the particle is a polystyrene particle, a carboxylated polysterene particle, a PLURIONICS stabilized polypropylene sulfide particle, or a poly (lactic-co-glycolic acid) particle. In some embodiments, the present invention provides methods of treating diabetes in a subject comprising administering to said subject an effective amount of a composition comprising an antigen-coupled particle to the subject, wherein the particle has a negative zeta potential. In some embodiments, the diabetes is type I diabetes. In some embodiments, the diabetes is type II diabetes.

In some embodiments, the antigen is insulin, proinsulin, islet-specific glucose-6-phophatase catalytic subunit-related protein (IGRP) or epitopes derived from insulin proinsulin, or IGRP. In some embodiments, the antigen is one or more antigen selected from the group consisting of ID NOs: 1767-1840, SEQ ID NOs: 1842-1962, SEQ ID NOs: 1964-2027, SEQ ID NOs: 2029-2073, SEQ ID NOs: 2075-2113, SEQ ID NOs: 2115-2197, SEQ ID NOs: 2199-2248, SEQ ID NOs: 2250-2259, SEQ ID NOs: 2261-2420, SEQ ID NOs: 2422-2486, and SEQ ID NOs: 2489-2505. In some embodiments, antigen is insulin and the antigen-coupled particle has a post-synthesis average size of about 300-800 nanometers and a post-synthesis average charge of about −30-to about −70 mV. In some embodiments, the particle has a post-synthesis average size of about 350-600 nanometers and a post-synthesis average charge of about −40 to about −60 mV. In some embodiments, the particle has a post-synthesis average size of about 500 nanometers and a post-synthesis average charge of about −50 mV. In some embodiments, the antigen is pro-insulin and the antigen-coupled particle has a post-synthesis average size of about 300-800 nanometers and a post-synthesis average charge of about −30 to about −70 mV. In certain embodiments, the particle has a has a post-synthesis average size of about 400-600 nanometers and a post-synthesis average charge of about −40 to about −60 mV. In some embodiments, the particle has a post-synthesis average size of about 570 nanometers and a post-synthesis average charge of about −45. In some embodiments, the antigen is IGRP and the antigen-coupled particle has a post-synthesis average size of about 300-800 nanometers and a post-synthesis average charge of about −30 to about −70 mV. In some embodiments, the particle has a has a post-synthesis average size of about 400-700 nanometers and a post-synthesis average charge of about −40 to about −60 mV. In some embodiments, the particle has a post-synthesis average size of about 600 nanometers and a post-synthesis average charge of about −40. In certain embodiments, the particle is a polystyrene particle, a carboxylated polysterene particle, a PLURIONICS stabilized polypropylene sulfide particle, or a poly(lactic-co-glycolic acid) particle.

In some embodiments, the present invention provides methods of treating a subject undergoing enzyme replacement therapy, comprising administering to said subject an effective amount of a composition comprising an antigen-coupled particle to the subject, wherein the particle has a negative zeta potential. In some embodiments, the subject is undergoing enzyme replacement therapy for treatment of a disease selected from the group consisting of Hemophilia, Hemophilia A, Hemophilia B, von Willebrand disease, a mucopolysaccharide storage disorder, gangliosidosis, alkaline hypophosphatasia, cholesterol ester storage disease, hyperuricemia, growth hormone deficiency, renal anemia Gaucher's Disease, Fabry's Disease, Hurler's Disease, Pompe's Disease, Hunter's Disease, and Maroteaux-Lary Disease. In some embodiments the antigen coupled particle comprises one or more enzyme selected from the group consisting of Advate, antihemophilic factor, Kogenate, Eloctate, recombinant factor VIII Fc fusion protein, Refacto, Novo VIIa, recombinant factor VII, eptacog alfa, Helixate, Monanine, Coagulation Factor IX, Wilate, Ceredase, Alglucerase, Cerezyme, Imiglucerase, Elelso, taliglucerase alfa, Fabrazyme, Agalsidase beta, Aldurazyme, -I-iduronidase, Myozyme, Acid-glucosidase, Elaprase, iduronate-2-sulfatase, Naglazyme arylsufatase B, and N-acetylgalactosamine-4-sulfatase. In some embodiments, the particle is a polystyrene particle, a carboxylated polysterene particle, a PLURIONICS stabilized polypropylene sulfide particle, or a poly(lactic-co-glycolic acid) particle. In certain embodiments, the particle is a co-polymer having a molar ratio from about 80:20 to about 100:0. In certain embodiments, the particle is a polystyrene particle, a carboxylated polysterene particle, a PLURIONICS stabilized polypropylene sulfide particle, or a poly(lactic-co-glycolic acid) particle. In other embodiments, the particle is a poly(lactic-co-glycolic acid) particle and has a copolymer ratio of about 50:50 polylactic acid:polyglycolic acid. In some embodiments, the particle is a poly(lactic-co-glycolic acid) particle and has a copolymer ratio of about 50:50 polylactic acid:polyglycolic acid.

In a further embodiment, the administration of the particles of the invention prevents the accumulation of neutrophils and other granulocytes in a subject. In a further embodiment, the particles of the invention are administered to a subject who has cancer.

In one embodiment, administration of the particles of the invention increases regeneration of damaged tissue. In a further embodiment, the particles increase regeneration of epithelial cells. In yet a further embodiment, the particles increase remyelination of neurons. In another embodiment, the subject has an autoimmune disease. In yet another embodiment, the subject has inflammatory bowel disease, including ulcerative colitis, and/or Crohn's disease. In yet another embodiment, the subject has multiple sclerosis.

In some embodiments the composition is administered intravenously. In some embodiments, the composition is administered subcutaneously, orally, intramuscularly, intralymphatically, portally or via aerosol. In one embodiment, administration of the negatively charged particles induces antigen-specific tolerance in a subject. In one embodiment, the particles that induce antigen-specific tolerance comprise one or more epitopes associated with an allergy, autoimmune disease, and/or inflammatory disease. In one embodiment, the epitopes are selected from those described in Tables 2 or 3. In one embodiment, the negatively charged particles are polystyrene, diamond, PLURONICS® stabilized polypropylene sulfide, or poly(lacti-co-glycolic acid) particles. In one embodiment the particles are carboxylated. In one embodiment, the particles have a zeta potential of less than about −100 mV. In one embodiment, the particles have a zeta potential between about −75 mV and 0 mV, for example, between −50 mV and 0 mV, or between −100 mV and −50 mV or between −75 mV and −50 mV or between −50 mV and −40 mV. In one embodiment, the particle has an average diameter of about 0.1 µm to about 10 µm, for example from about 0.2 µm to about 2 µm or about 0.3 µm to about 5 µm, or 0.5 µm to about 3 µm or about 0.5 µm to about 1 µm.

In one embodiment, the subject has an autoimmune disease. In one embodiment, the autoimmune disease is multiple sclerosis, scleroderma, type-I diabetes, rheumatoid arthritis, thyroiditis, systemic lupus erythmatosis, Reynaud's syndrome, Sjorgen's syndrome, autoimmune uveitis, autoimmune myocarditis, inflammatory bowel disease, Amyotrophic Lateral Sclerosis (ALS), Systemic Lupus, Neuromyelitis Optica, Idiopathic Thrombocytopenic Purpura, Thrombotic Thrombocytopenic Purpura, Membranous Nephropathy, Bullous Phemphigoid, Phemphigus Vulgaris, Myasthenia Gravis, Celiac disease, ulcerative colitis, or Crohn's disease. In one embodiment, the particle comprises a full-length polypeptide or fragment thereof. In one embodiment, the particle comprises one or more myelin basic protein epitopes. In one embodiment, the myelin basic protein epitope is from SEQ ID NO: 4975 or SEQ ID NO: 4976. In one embodiment, the particles comprise one or more myelin oligodendrocyte glycoprotein epitopes. In one embodiment, the myelin oligodendrocyte glycoprotein epitope is from SEQ ID NO: 1 or SEQ ID NO: 4978. In one embodiment, the particle contains one or more insulin epitopes. In one embodiment, the one or more insulin epitopes is from SEQ ID NO: 4981. In one embodiment, the particle comprises one or more glutamic acid decarboxylase epitopes. In one embodiment, the glutamic acid decarboxylase epitopes is from SEQ ID NO: 4982. In one embodiment, the particle contains one or more proteolipid protein epitopes. In one embodiment, the proteolipid protein epitope is from SEQ ID NO: 4977. In one embodiment, the particle comprises one or more gliaden epitopes. In one embodiment, the gliaden epitopes comprise SEQ ID NOs: 4983-4985.

In some embodiments, the present invention further provides a process for the preparation an immune modified particle with a negative zeta potential said process comprising: contacting an immune modified particle precursor with a buffer solution under conditions effective to form the immune modified particle with a negative zeta potential. In some embodiments, the immune modified particle precursor is formed by co-polymerization. In some embodiments, the buffer solution has a basic pH. In some embodiments, buffer solution is sodium bicarbonate, potassium bicarbonate, lithium bicarbonate, potassium dihydrogen phosphate, sodium dihydrogen phosphate, or lithium dihydrogen phosphate.

In some embodiments, the present invention provides a composition comprising an antigen encapsulated within the core of a surface-functionalized liposome. In a further embodiment, the liposome is composed at a 30:30:40 ratio of phosphatidylcholine:phosphatidylglycerol:cholesterol. In yet a further embodiment, said antigen comprises an autoimmune antigen, an antigen expressed on a tissue to be transplanted into a subject, or an allergen. In some embodiments, the particle is a poly(lactic-co-glycolic acid) particle and has a copolymer ratio of about 50:50 polylactic acid:polyglycolic acid. In some embodiments, the particles comprise PEMA. In some embodiments, the PEMA is present at about 0.1% to about 2.0%.

BRIEF DESCRIPTION OF THE DRAWINGS

FIGS. 1A-1C show (FIG. 1A) a micrograph of a poly (lactide-co-glycolide) (PLG) particle. FIG. 1B and FIG. 1C show the characterization of surface-functionalized poly (lactide-co-glycolide) particles by dynamic light scattering analysis, including the size distribution, average size (nm), $\zeta$ potential (mV), and peptide coupling efficiency (%) of $OVA_{323-339}$ and $PLP_{139-151}$ peptides with PLG-PEMA particles. Surface-functionalized poly(lactide-co-glycolide) particles were analyzed on a Malvern Zetasizer Nano ZS (Malvern Instruments, Westborough, Mass.) at a count rate of $2.5 \times 10^5$ counts per second in 18.2 M$\Omega$ water. The population of surface-functionalized poly(lactide-co-glycolide) particles varied by 5-15% per batch but generally had a Z-average diameter of 567 nm, a peak diameter of 670 nm and a polydispersity index of 0.209.

(FIG. 3A) shows the mean clinical score and FIG. 3B) shows the mean cumulative score of the EAE animals. Mice were treated with EITHER $OVA_{323-339}$-PLS (N=5), $OVA_{323-339}$-PLGA$_{PHOSPOREX}$ (N=5), $OVA_{323-339}$-PLGA$_{PEMA}$ (N=5), $PLP_{139-151}$-PLA (N=5), $PLP_{139-151}$-PLGA$_{PHOSPOREX}$ (N=5), or $PLP_{139-151}$-PLG$_{PEMA}$ (N=5) on day −7 relative to the time of immunization (day 0). Peak disease was typically observed around day 12 to 14, and mice are scored for clinical disease. Particles, of any composition that were modified with the control peptide $OVA_{323-339}$ did not prevent disease induction. However, the $PLP_{139-151}$ coupled PLG beads were more effective in down-regulating induction of R-EAE than $PLP_{139-151}$ coupled commercial (phosphorex) PLG or polystyrene.

FIGS. 11C-F are graphs showing the quantification of the image data.

FIG. 40A shows the mean clinical score, and FIG. 40B shows the mean cumulative score of the EAE animals. Mice received TIMP (tolerogenic immune modifying particles) having a charge of either −60 mv or −25 mv conjugated to an antigen. Mice were treated with either $OVA_{323-339}$-$TIMP_{-60mv}$, $OVA_{323-339}$-$PLGA_{-25mv}$, $PLP_{139-151}$-$TIMP_{-60mv}$, or $PLP_{139-151}$-$PLGA_{-25mv}$ and scored for clinical disease. The more negatively charged particles, $TIMP_{-60mv}$, induce tolerance more effectively than the $PLGA_{-25mv}$ particles.

FIG. 42A shows that the most effective average particle size is 500 nm. Mice were treated with either 500 nm $OVA_{323-339}$-PSB, 100 nm $PLP_{139-151}$-PSB, 500 nm $PLP_{139-151}$-PSB, 1.75 μm $PLP_{139-151}$-PSB, or 4.5 μm $PLP_{139-151}$-PSB and scored for clinical disease. FIG. 42B shows that 24 hours after i.v. infusion fluorescently labelled particles with a 50:50 lactide:glycolide ratio have significantly cleared from the spleen, liver and lung.

FIG. 43A shows that OVA-PLG surface coupled particles fail to reduce the TH2 response. FIG. 43B shows that $TIMP_{PEMA-60mv}$ (OVA encapsulated within the particle)

inhibit the TH2 response. FIG. 43C shows that TIMP$_{PEMA-60mv}$ (OVA encapsulated within the particle) inhibit recall responses.

DETAILED DESCRIPTION OF THE INVENTION

Figure 2:
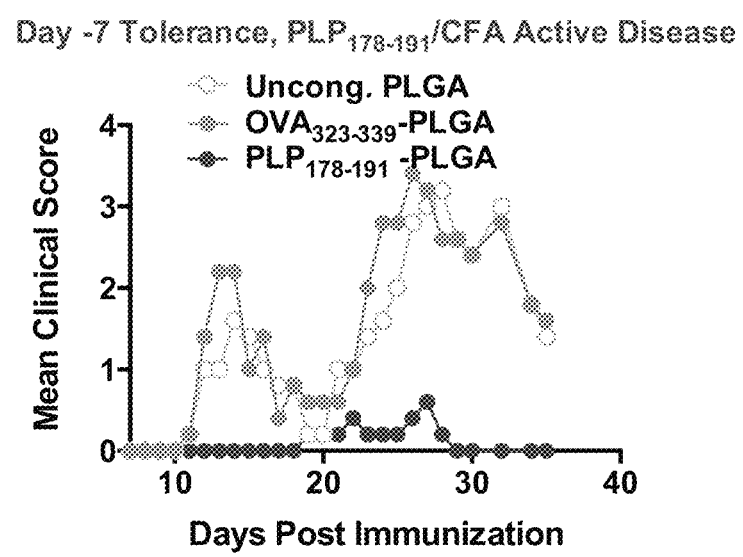
FIG. 2 shows that PLG nanoparticles induce antigen-specific tolerance. The immunodominant proteolipid protein $PLP_{139-151}$ epitope (PLG-$PLP_{139-151}$) was used to induce tolerance for prevention of Relapsing Experimental Autoimmune Encephalitis (R-EAE). Mice were treated with either $PLP_{139-151}$-PLGA (N=5), $OVA_{323-339}$-PLGA (N=5), or uncongugated PLGA (N=5) on day −7 relative to the time of immunization (day 0). Peak disease was typically observed around day 12 to 14, and mice are scored for clinical disease. Particles without peptide, or modified with the control peptide $OVA_{323-339}$ did not prevent disease induction. However, PLGA particles modified with $PLP_{139-151}$ produced a clinical score of 0 (no disease) at all except low clinical scores of under 1 exhibited between days 20 and 30.

The present inventors have found that nanoparticles coupled to an antigen can induce tolerance to autoimmune disease and decrease the immune response. These particles can induce tolerance regardless of whether they are bound to the surface of the particle or encapsulated within. These, particles, therefore, may be useful in the treatment of any disease or condition characterized by an excessive inflammatory immune response, such as autoimmune diseases or allergies.

"Particle" as used herein refers to any non-tissue derived composition of matter, it may be a sphere or sphere-like entity, bead, or liposome. The term "particle", the term "immune modifying particle", the term "carrier particle", and the term "bead" may be used interchangeably depending on the context. Additionally, the term "particle" may be used to encompass beads and spheres.

"Negatively charged particle" as used herein refers to particles which have been modified to possess a net surface charge that is less than zero.

"Carboxylated particles" or "carboxylated beads" or "carboxylated spheres" includes any particle that has been modified to contain a carboxyl group on its surface. In some embodiments the addition of the carboxyl group enhances phagocyte/monocyte uptake of the particles from circulation, for instance through the interaction with scavenger receptors such as MARCO. Carboxylation of the particles can be achieved using any compound which adds carboxyl groups, including, but not limited to, Poly(ethylene-maleic anhydride) (PEMA).

"Antigenic moiety" as used herein refers to any moiety, for example a peptide, that is recognized by the host's immune system. Examples of antigenic moieties include, but are not limited to, autoantigens, enzymes, and/or bacterial or viral proteins, peptides, drugs or components. Without being bound by theory, while the carboxylated beads themselves may be recognized by the immune system, the carboxylated beads with nothing more attached thereto are not considered an "antigenic moiety" for the purposes of the invention.

"Naked beads" or "naked particles" or "naked spheres" as used herein refers to beads, particles or spheres that have not been carboxylated.

"Pro-inflammatory mediators" or "pro-inflammatory polypeptides" as used herein refers to polypeptides or fragments thereof which induce, maintain, or prolong inflammation in a subject. Examples of pro-inflammatory mediators include, but are not limited to, cytokines and chemokines.

As used herein, the term "Inflammatory monocyte" refers to any myeloid cell expressing any combination of CD14/CD26 and CCR2.

As used herein, the term "inhibitory neutrophil" refers to neutrophils, and/or monocyte derived suppressor cells.

As used herein, the term "Th cell" or "helper T cell" refers to CD4$^+$ cells. CD4$^+$ T cells assist other white blood cells with immunologic processes, including maturation of B cells into plasma cells and memory B cells, and activation of cytotoxic T cells and macrophages. T cells become activated when they are presented with peptide antigens by MHC class II molecules, which are expressed on the surface of antigen-presenting cells (APCs).

As used herein, the term "Th1 cell" refers to a subset of Th cells which produce proinflammatory mediators. Th1 cells secrete cytokines to facilitate immune response and play a role in host defense against pathogens in part by mediating the recruitment of neutrophils and macrophages to infected tissues. Th1 cells secrete cytokines including IFN-gamma, IL2, IL-10, and TNF alpha/beta to coordinate defense against intracellular pathogens such as viruses and some bacteria.

As used herein, the term "Th2 cell" refers to a subset of Th cells that mediate the activation and maintenance of the antibody-mediated immune response against extracellular parasites, bacteria, allergens, and toxins. Th2 cells mediate these functions by producing various cytokines such as IL-4, IL-5, IL-6, IL-9, IL-13, and IL-17E (IL-25) that are responsible for antibody production, eosinophil activation, and inhibition of several macrophage functions, thus providing phagocyte-independent protective responses.

As used herein, the term "Th17 cell" refers to a subset of Th cells. Th17 cells secrete cytokines to facilitate immune response and play a role in host defense against pathogens by mediating the recruitment of neutrophils and macrophages to infected tissues. TH17 cells secrete cytokines such as IL17, IL21, IL22, IL24, IL26 and TNF alpha to coordinate defense against extracellular pathogens including fungi and bacteria.

"Coupled" as used herein refers to an antigen fixed to the outside of a particle or encapsulated within a particle. Thus, an antigen coupled to a particle includes both surface coupling as well as encapsulation within the particle.

The term "IMP" as used herein refers to immune-modifying particles which are not coupled to an antigen. The term "TIMP" as used herein refers to tolerizing immune modifying particles which are coupled to an antigen. In some embodiments, the antigen is attached to the surface of the TIMP. In other embodiments, the antigen is encapsulated within the TIMP.

The particle may have any particle shape or conformation. However, in some embodiments it is preferred to use particles that are less likely to clump in vivo. Examples of particles within these embodiments are those that have a spherical shape.

Another aspect of the invention relates to a composition which comprises an immune modified particle having a negative zeta potential and free from antigenic moieties. In a further embodiment, the invention provides compositions comprising an immune modified particle with a negative zeta potential coupled to an antigen. In a further embodiment, the antigen is coupled to the outside of the particle. In a preferred embodiment, the antigen is encapsulated within the particle.

Yet another aspect of the invention relates to a process for the preparation an immune modified particle with a negative zeta potential and free from antigenic moieties. The process involves contacting an immune modified particle precursor with a buffer solution under conditions effective to form the immune modified particle with a negative zeta potential. In some embodiments of this invention, the immune modified particle precursor is formed via co-polymerization. The particle microstructure may depend on the method of co-polymerization.

In some embodiments, an antigenic peptide molecule is coupled to the carrier particle (e.g. immune modified particle) by a conjugate molecule and/or linker group. In some embodiments, coupling of the antigenic peptide and/or apoptotic signalling molecule to the carrier (e.g., PLG particle) comprises one or more covalent and/or non-covalent interactions. In some embodiments, the antigenic peptide is attached to the surface of the carrier particle with a negative zeta potential. In some embodiments, the antigenic peptide is encapsulated within the carrier particle with a negative zeta potential.

In one embodiment, the buffer solution contacting the immune modified particle may have a basic pH. Suitable basic pH for the basic solution include 7.1, 7.5, 8.0, 8.5, 9.5, 10.0 10.5, 11.0, 11.5, 12.0, 12.5, 13.0, and 13.5. The buffer solution may also be made of any suitable base and its conjugate. In some embodiments of the invention, the buffer solution may include, without limitation, sodium bicarbonate, potassium bicarbonate, lithium bicarbonate, potassium dihydrogen phosphate, sodium dihydrogen phosphate, or lithium dihydrogen phosphate and conjugates thereof.

In one embodiment of the invention, the immune modified particles contain co-polymers. These co-polymers may have varying molar ratio. Suitable co-polymer ratio of present immune modified particles may be 25:75, 30:70, 35:65, 40:60, 45:55, 50:50, 55:45, 60:40, 65:35, 70:30, 75:25, 80:20, 81:19, 82:18, 83:17, 84:16, 85:15, 86:14, 87:13, 88:12, 89:11, 90:10, 91:9, 92:8, 93:7, 94:6, 95:5, 96:4, 97:3, 98:2, 99:1, or 100:0. In another embodiment, the co-polymer may be periodical, statistical, linear, branched (including star, brush, or comb co-polymers) co-polymers. In some embodiments, the co-polymers ratio may be, but not limited to, polystyrene:poly(vinyl carboxylate)/80:20, polystyrene:poly(vinyl carboxylate)/90:10, poly(vinyl carboxylate):polystyrene/80:20, poly(vinyl carboxylate):polystyrene/90:10, polylactic acid:polyglycolic acid/50:50, polylactic acid:polyglycolic acid/80:20, or polylactic acid:polyglycolic acid/90:10.

In one embodiment, the particles of the invention are made by adding a composition comprising the polymer (e.g. PLGA) to a solution of Poly(ethylene-maleic anhydride) (PEMA). The concentration of PEMA in the solution can be between about 0.1% and about 10%. In one embodiment, the concentration of PEMA in the solution is between about 0.2% and about 5%. In another embodiment, the concentration of PEMA in the solution is between about 0.1% and 4%. In another embodiment, the concentration of PEMA in the solution is between about 0.1% and 2%. In another embodiment, the concentration of PEMA in the solution is between about 0.5% and 1%. In one embodiment, the percentage of PEMA in solution is 0.1%, 0.2%, 0.3%, 0.4%, 0.5%, 0.6% 0.7%, 0.8%, 0.9%, 1%, 1.5%, 2%, 2.5%, 3%, 3.5%, 4%, 4.5%, 5%, 6%, 6.5%, 7%, 7.5%, 8%, 8.5%, 9%, 9.5% or 10%. In one embodiment, the percentage of PEMA in the solution is about 0.5%. In another embodiment, the percentage of PEMA in the solution is about 1.0%. Other compounds that may be used include, but are not limited to, Poly(ethylene-alt-maleic anhydride), Poly(isobutylene-co-maleic acid), Poly(methyl vinyl ether-alt-maleic acid), Poly(methyl vinyl ether-alt-maleic acid monoethyl ester), Poly(methyl vinyl ether-alt-maleic anhydride), Poly(methyl vinyl ether-alt-maleic anhydride) cross-linked with 1,9-decadiene powder, and/or Poly(styrene-alt-maleic acid) sodium salt.

In one embodiment, the particle is a liposome. In a further embodiment, the particle is a liposome composed of the following lipids at the following molar ratios—30:30:40 phosphatidylcholine:phosphatidylglycerol:cholesterol. In yet a further embodiment, the particle is encapsulated within a liposome.

It is not necessary that each particle be uniform in size, although the particles must generally be of a size sufficient to be sequestered in the spleen or liver and trigger phagocytosis or uptake through receptor or non-receptor mediated mechanism by an antigen presenting cell, including endothelial cell or other MPS cell. Preferably, the particles are microscopic or nanoscopic in size, in order to enhance solubility, avoid possible complications caused by aggregation in vivo and to facilitate pinocytosis. Particle size can be a factor for uptake from the interstitial space into areas of lymphocyte maturation. A particle having a diameter of from about 0.1 µm to about 10 µm is capable of triggering phagocytosis. Thus in one embodiment, the particle has a diameter within these limits. In another embodiment, the particle has an average diameter of about 0.3 µm to about 5 µm. In still another embodiment, the particle has an average diameter of about 0.5 µm to about 3 µm. In another embodiment, the particle has an average diameter of about 0.2 µm to about 2 µm. In a further embodiment the particle has an average size of about 0.1 µm, or about 0.2 µm or about 0.3 µm or about 0.4 µm or about 0.5 µm or about 1.0 µm or about 1.5 µm or about 2.0 µm or about 2.5 µm or about 3.0 µm or about 3.5 µm or about 4.0 µm or about 4.5 µm or about 5.0 µm. In a particular embodiment the particle has an average size of about 0.5 µm. In some embodiments, the overall weights of the particles are less than about 10,000 kDa, less than about 5,000 kDa, or less than about 1,000 kDa, 500 kDa, 400 kDa, 300 kDa, 200 kDa, 100 kDa, 50 kDa, 20 kDa, 10 kDa. The particles in a composition need not be of uniform diameter. By way of example, a pharmaceutical formulation may contain a plurality of particles, some of which are about 0.5 µm, while others are about 1.0 µm. Any mixture of particle sizes within these given ranges will be useful.

The particles of the current invention can possess a particular zeta potential. In certain embodiments, the zeta potential is negative. In one embodiment, the zeta potential is less than about −100 mV. In one embodiment, the zeta potential is less than about −50 mV. In certain embodiments, the particles possess a zeta potential between −100 mV and 0 mV. In a further embodiment, the particles possess a zeta potential between −75 mV and 0 mV. In a further embodiment, the particles possess a zeta potential between −60 mV and 0 mV. In a further embodiment, the particles possess a zeta potential between −50 mV and 0 mV. In still a further embodiment, the particles possess a zeta potential between −40 mV and 0 mV. In a further embodiment, the particles possess a zeta potential between −30 mV and 0 mV. In a further embodiment, the particles possess a zeta potential between −20 mV and +0 mV. In a further embodiment, the particles possess a zeta potential between −10 mV and −0 mV. In a further embodiment, the particles possess a zeta potential between −100 mV and −50 mV. In another particular embodiment, the particles possess a zeta potential between −75 mV and −50 mV. In a particular embodiment, the particles possess a zeta potential between −50 mV and −40 mV.

In some embodiments, the charge of a carrier (e.g., positive, negative, neutral) is selected to impart application-specific benefits (e.g., physiological compatibility, beneficial surface-peptide interactions, etc.). In some embodiments, a carrier has a net neutral or negative charge (e.g., to reduce non-specific binding to cell surfaces which, in general, bear a net negative charge). In certain embodiments carriers are capable of being conjugated, either directly or indirectly, to an antigen to which tolerance is desired (also referred to herein as an antigen-specific peptide, antigenic peptide, autoantigen, inducing antigen or tolerizing antigen). In some instances, a carrier has multiple binding sites (e.g., 2, 3, 4, 5, 6, 7, 8, 9, 10 . . . 20 . . . 50 . . . 100, or more) in order to have multiple copies of an antigen-specific peptide, or multiple different peptides, exposed on the surface (e.g., to increase the likelihood of a tolerance response). In some embodiments, a carrier displays a single type of antigenic peptide. In some embodiments, a carrier displays multiple different antigenic peptides on the surface. In some embodiments, a carrier surface displays functional groups for the covalent attachment of selected moieties (e.g., antigenic peptides). In some embodiments, carrier surface functional groups provide sites for non-covalent interaction with selected moieties (e.g., antigenic peptides). In some embodiments, a carrier has a surface to which conjugating moieties may be adsorbed without chemical bond formation.

The size and charge of the particles are critical for tolerance induction. While the particles will differ in size and charge based on the antigen encapsulated within them (See Table 1 for examples of specific particles), in general, particles of the current invention are effective at inducing tolerance when they are between about 100 nanometers and about 1500 nanometers and have a charge of 0 to about −70 mV and are most effective at inducing tolerance when they are 400-800 microns and have a charge of between about −25 mV and −70 mV. Furthermore, as shown in Table 1, due in part to the concentration of the particles and presence of sucrose and D-mannitol in the lyophilisation process, the average particle size and charge of the particles can be slightly altered in the lyophilisation process, therefore, both post-synthesis averages and post-lyophilization averages are given below. As used herein, the term "post-synthesis size" and "post synthesis charge" refer to the size and charge of the particle prior to lyophilization. The term "post lyophilization size" and "post lyophilization charge" refer to the size and charge of the particle after lyophilization.

without there being an accumulation of particles in the individual. Examples of suitable particles include polystyrene particles, PLGA particles, PLURIONICS stabilized polypropylene sulfide particles, and diamond particles.

Preferably the particle surface is composed of a material that minimizes non-specific or unwanted biological interactions. Interactions between the particle surface and the interstitium may be a factor that plays a role in lymphatic uptake. The particle surface may be coated with a material to prevent or decrease non-specific interactions. Steric stabilization by coating particles with hydrophilic layers such as poly(ethylene glycol) (PEG) and its copolymers such as PLURONICS® (including copolymers of poly(ethylene glycol)-bl-poly(propylene glycol)-bl-poly(ethylene glycol)) may reduce the non-specific interactions with proteins of the interstitium as demonstrated by improved lymphatic uptake following subcutaneous injections. All of these facts point to the significance of the physical properties of the particles in terms of lymphatic uptake. Biodegradable polymers may be used to make all or some of the polymers and/or particles and/or layers. Biodegradable polymers may undergo degradation, for example, by a result of functional groups reacting with the water in the solution. The term "degradation" as used herein refers to becoming soluble, either by reduction of molecular weight or by conversion of hydrophobic groups to hydrophilic groups. Polymers with ester groups are generally subject to spontaneous hydrolysis, e.g., polylactides and polyglycolides.

Particles of the present invention may also contain additional components. For example, carriers may have imaging agents incorporated or conjugated to the carrier. An example of a carrier nanosphere having an imaging agent that is currently commercially available is the Kodak X-sight nanospheres. Inorganic quantum-confined luminescent nanocrystals, known as quantum dots (QDs), have emerged as ideal donors in FRET applications: their high quantum yield and tunable size-dependent Stokes Shifts permit different sizes to emit from blue to infrared when excited at a single ultraviolet wavelength. (Bruchez, et al., Science, 1998, 281, 2013; Niemeyer, C. M Angew. Chem. Int. Ed. 2003, 42, 5796; Waggoner, A. Methods Enzymol. 1995, 246, 362;

TABLE 1

REPRESENTATIVE PARTICLE ANALYSIS

| Antigen | Particle Material | Copolymer ratio | Surfactant used | Average Size post synthesis (post lyophilisation) nm | Average Charge post synthesis (post lyophilisation) mV |
|---|---|---|---|---|---|
| OVA | PLGA (carboxylated) | 50:50 | PEMA | 566.5 (538.5) | 51.2 (66.0) |
| Insulin | PLGA (carboxylated) | 50:50 | PEMA | 500.9 (385.2) | 48.4 (53.7) |
| $PLP_{139-151}$ | PLGA (carboxylated) | 50:50 | PEMA | 429.9 (359.6) | 53.7 (69.4) |
| Gliaden | PLGA (carboxylated) | 50:50 | PEMA | 606.1 (1104.0) | 48.8 (68.1) |
| Proinsulin | PLGA (carboxylated) | 50:50 | PEMA | 566.6 (407.2) | 44.1 (49.7) |
| Lysozyme | PLGA (carboxylated) | 50:50 | PEMA | 435.3 (393.3) | 48.1 (65.1) |
| IGRP | PLGA (carboxylated) | 50:50 | PEMA | 612.5 (399.3) | 41.0 (57.6) |
| Empty particle (No As) | PLGA (carboxylated) | 50:50 | PEMA | 383.9 (343.3) | 52.6 (61.3) |

In some embodiments, the particle is non-metallic. In these embodiments the particle may be formed from a polymer. In a preferred embodiment, the particle is biodegradable in an individual. In this embodiment, the particles can be provided in an individual across multiple doses Brus, L. E. J. Chem. Phys. 1993, 79, 5566). Quantum dots, such as hybrid organic/inorganic quantum dots based on a class of polymers known as dendrimers, may used in biological labeling, imaging, and optical biosensing systems. (Lemon, et al., J. Am. Chem. Soc. 2000, 122, 12886). Unlike the traditional synthesis of inorganic quantum dots, the synthesis of these hybrid quantum dot nanoparticles does not require high temperatures or highly toxic, unstable reagents. (Etienne, et al., Appl. Phys. Lett. 87, 181913, 2005).

Particles can be formed from a wide range of materials. The particle is preferably composed of a material suitable for biological use. For example, particles may be composed of glass, silica, polyesters of hydroxy carboxylic acids, polyanhydrides of dicarboxylic acids, or copolymers of hydroxy carboxylic acids and dicarboxylic acids. More generally, the carrier particles may be composed of polyesters of straight chain or branched, substituted or unsubstituted, saturated or unsaturated, linear or cross-linked, alkanyl, haloalkyl, thioalkyl, aminoalkyl, aryl, aralkyl, alkenyl, aralkenyl, heteroaryl, or alkoxy hydroxy acids, or polyanhydrides of straight chain or branched, substituted or unsubstituted, saturated or unsaturated, linear or cross-linked, alkanyl, haloalkyl, thioalkyl, aminoalkyl, aryl, aralkyl, alkenyl, aralkenyl, heteroaryl, or alkoxy dicarboxylic acids. Additionally, carrier particles can be quantum dots, or composed of quantum dots, such as quantum dot polystyrene particles (Joumaa et al. (2006) Langmuir 22: 1810-6). Carrier particles including mixtures of ester and anhydride bonds (e.g., copolymers of glycolic and sebacic acid) may also be employed. For example, carrier particles may comprise materials including polyglycolic acid polymers (PGA), polylactic acid polymers (PLA), polysebacic acid polymers (PSA), poly(lactic-co-glycolic) acid copolymers (PLGA or PLG; the terms are interchangeable), [rho]oly(lactic-co-sebacic) acid copolymers (PLSA), poly(glycolic-co-sebacic) acid copolymers (PGSA), polypropylene sulfide polymers, poly(caprolactone), chitosan, etc. Other biocompatible, biodegradable polymers useful in the present invention include polymers or copolymers of caprolactones, carbonates, amides, amino acids, orthoesters, acetals, cyanoacrylates and degradable urethanes, as well as copolymers of these with straight chain or branched, substituted or unsubstituted, alkanyl, haloalkyl, thioalkyl, aminoalkyl, alkenyl, or aromatic hydroxy- or di-carboxylic acids. In addition, the biologically important amino acids with reactive side chain groups, such as lysine, arginine, aspartic acid, glutamic acid, serine, threonine, tyrosine and cysteine, or their enantiomers, may be included in copolymers with any of the aforementioned materials to provide reactive groups for conjugating to antigen peptides and proteins or conjugating moieties. Biodegradable materials suitable for the present invention include diamond, PLA, PGA, polypropylene sulfide, and PLGA polymers. Biocompatible but non-biodegradable materials may also be used in the carrier particles of the invention. For example, non-biodegradable polymers of acrylates, ethylene-vinyl acetates, acyl substituted cellulose acetates, non-degradable urethanes, styrenes, vinyl chlorides, vinyl fluorides, vinyl imidazoles, chlorosulphonated olefins, ethylene oxide, vinyl alcohols, TEFLON® (DuPont, Wilmington, Del.), and nylons may be employed.

The particles of the instant invention can be manufactured by any means commonly known in the art. Exemplary methods of manufacturing particles include, but are not limited to, microemulsion polymerization, interfacial polymerization, precipitation polymerization, emulsion evaporation, emulsion diffusion, solvent displacement, and salting out (Astete and Sabliov, J. Biomater. Sci. Polymer Edn., 17:247-289 (2006)). Manipulation of the manufacturing process for PLGA particles can control particle properties (e.g. size, size distribution, zeta potential, morphology, hydrophobicity/hydrophilicity, polypeptide entrapment, etc). The size of the particle is influenced by a number of factors including, but not limited to, the concentration of PLGA, the solvent used in the manufacture of the particle, the nature of the organic phase, the surfactants used in manufacturing, the viscosity of the continuous and discontinuous phase, the nature of the solvent used, the temperature of the water used, sonication, evaporation rate, additives, shear stress, sterilization, and the nature of any encapsulated antigen or polypeptide.

Particle size is affected by the polymer concentration; higher particles are formed from higher polymer concentrations. For example, an increase in PLGA concentration from 1% to 4% (w/v) can increase mean particle size from about 205 nm to about 290 nm when the solvent propylene carbonate is used. Alternatively, in ethyl acetate and 5% Pluronic F-127, an increase in PLGA concentration from 1% to 5% (w/v) increases the mean particle size from 120 nm to 230 nm.

The viscosity of the continuous and discontinuous phase is also an important parameter that affects the diffusion process, a key step in forming smaller particles. The size of the particles increases with an increase in viscosity of the dispersed phase, whereas the size of the particles decreases with a more viscous continuous phase. In general, the lower the phase ratio of organic to aqueous solvent, the smaller the particle size.

Homogenizer speed and agitation also affect particle size; in general, higher speeds and agitation cause a decrease in particle size, although there is a point where further increases in speed and agitation no longer decrease particle size. There is a favorable impact in the size reduction when the emulsion is homogenized with a high pressure homogenizer compared with just high stirring. For example, at a phase ration of 20% in 5% PVA, the mean particle size with stirring is 288 nm and the mean particle size with homogenization (high pressure of 300 bars) is 231 nm.

An important size reduction of the particles can be achieved by varying the temperature of the water added to improve the diffusion of the solvent. The mean particle size decreases with an increase in water temperature.

The nature of the polypeptide encapsulated in the particle also affects particle size. In general, encapsulation of hydrophobic polypeptides leads to the formation of smaller particles compared with the encapsulation of more hydrophilic polypeptides. In the double emulsion process, the entrapment of more hydrophilic polypeptides is improved by using high molecular mass PLGA and a high molecular mass of the first surfactant which causes a higher inner phase viscosity. The interaction between the solvent, polymer, and polypeptide affects the efficiency of incorporating the polypeptide into the particle.

The PLGA molecular mass impacts the final mean particle size. In general, the higher the molecular mass, the higher the mean particle size. For example, as the composition and molecular mass of PLGA varies (e.g. 12 to 48 kDa for 50:50 PLGA; 12 to 98 kDa for 75:25 PLGA) the mean particle size varies (about 102 nm-154 nm; about 132 nm to 152 nm respectively). Even when particles are the same molecular mass, their composition can affect average particle size; for example, particles with a 50:50 ratio generally form particles smaller than those with a 75:25 ratio. The end groups on the polymer also affects particle size. For example, particles prepared with ester end-groups form particles with an average size of 740 nm (PI=0.394) compared with the mean size for the acid PLGA end-group is 240 nm (PI=0.225).

The solvent used can also affect particle size; solvents that reduce the surface tension of the solution also reduce particle size.

The organic solvent is removed by evaporation in a vacuum to avoid polymer and polypeptide damage and to promote final particle size reduction. Evaporation of the organic solvent under vacuum is more efficient in forming smaller particles. For example, evaporation in vacuum produces a mean particle size around 30% smaller than the mean particle size produced under a normal rate of evaporation.

The amplitude of the sonication wavelength also affects the particle characteristics. The amplitude of the wavelength should be over 20% with 600 to 800 s of sonication to form sable miniemulsions with no more droplet size changes. However, the main draw-back of sonication is the lack of monodispersity of the emulsion formed.

Organic phases that may be used in the production of the particles of the invention include, but are not limited to, ethyl acetate, methyl ethyl ketone, propylene carbonate, and benzyl alcohol. The continuous phases that may be used, include but are not limited to the surfactant poloxamer 188.

A variety of surfactants can be used in the manufacturing of the particles of the invention. The surfactant can be anionic, cationic, or nonionic. Surfactants in the poloxamer and poloaxamines family are commonly used in particle synthesis. Surfactants that may be used, include, but are not limited to PEG, Tween-80, gelatin, dextran, pluronic L-63, PVA, methylcellulose, lecithin and DMAB. Additionally, biodegradable and biocompatible surfactants including, but not limited to, vitamin E TPGS (D-α-tocopheryl polyethylene glycol 1000 succinate). In certain embodiments, two surfactants are needed (e.g. in the double emulsion evaporation method). These two surfactants can include a hydrophobic surfactant for the first emulsion, and a hydrophobic surfactant for the second emulsion.

Solvents that may be used in the production of the particles of the invention include, but are not limited to, acetone, Tetrahydrofuran (THF), chloroform, and members of the chlorinate family, methyl chloride. The choice of organic solvents require two selection criteria: the polymer must be soluble in this solvent, and the solvent must be completely immiscible with the aqueous phase.

Salts that may be used in the production of the particles of the invention include, but are not limited to magnesium chloride hexahydrate, magnesium acetate tetrahydrate.

Common salting-out agents include, but are not limited to, electrolytes (e.g. sodium chloride, magnesium acetate, magnesium chloride), or non-electrolytes (e.g. sucrose).

The stability and size of the particles of the invention may be improved by the addition of compounds including, but not limited to, fatty acids or short chains of carbons. The addition of the longer carbon chain of lauric acid is associated with the improvement of particle characteristics. Furthermore, the addition of hydrophobic additives can improve the particle size, incorporation of the polypeptide into the particle, and release profile. Preparations of particles can be stabilized by lyophilization. The addition of a cryoprotectant such as trehalose can decrease aggregation of the particles upon lyophilization.

Suitable beads which are currently available commercially include polystyrene beads such as FluoSpheres (Molecular Probes, Eugene, Oreg.).

In some embodiments, the present invention provides systems comprising: (a) a delivery scaffold configured for the delivery of chemical and/or biological agents to a subject; and (b) antigen-coupled poly(lactide-co-glycolide) particles for induction of antigen-specific tolerance. In some embodiments, at least a portion of said delivery scaffold is microporous. In some embodiments, the antigen-coupled poly(lactide-co-glycolide) particles are encapsulated within said scaffold. In some embodiments, the chemical and/or biological agents are selected from the group consisting of: protein, peptide, small molecules, nucleic acids, cells, and particles. In some embodiments, chemical and/or biological agents comprise cell, and said cells comprise pancreatic islet cells.

Physical properties are also related to a nanoparticle's usefulness after uptake and retention in areas having immature lymphocytes. These include mechanical properties such as rigidity or rubberiness. Some embodiments are based on a rubbery core, e.g., a poly(propylene sulfide) (PPS) core with an overlayer, e.g., a hydrophilic overlayer, as in PEG, as in the PPS-PEG system recently developed and characterized for systemic (but not targeted or immune) delivery. The rubbery core is in contrast to a substantially rigid core as in a polystyrene or metal nanoparticle system. The term rubbery refers to certain resilient materials besides natural or synthetic rubbers, with rubbery being a term familiar to those in the polymer arts. For example, cross-linked PPS can be used to form a hydrophobic rubbery core. PPS is a polymer that degrades under oxidative conditions to polysulphoxide and finally polysulphone, transitioning from a hydrophobic rubber to a hydrophilic, water-soluble polymer. Other sulphide polymers may be adapted for use, with the term sulphide polymer referring to a polymer with a sulphur in the backbone of the mer. Other rubbery polymers that may be used are polyesters with glass transition temperature under hydrated conditions that is less than about 37° C. A hydrophobic core can be advantageously used with a hydrophilic overlayer since the core and overlayer will tend not to mingle, so that the overlayer tends to sterically expand away from the core. A core refers to a particle that has a layer on it. A layer refers to a material covering at least a portion of the core. A layer may be adsorbed or covalently bound. A particle or core may be solid or hollow. Rubbery hydrophobic cores are advantageous over rigid hydrophobic cores, such as crystalline or glassy (as in the case of polystyrene) cores, in that higher loadings of hydrophobic drugs can be carried by the particles with the rubbery hydrophobic cores.

Another physical property is the surface's hydrophilicity. A hydrophilic material may have a solubility in water of at least 1 gram per liter when it is uncrosslinked. Steric stabilization of particles with hydrophilic polymers can improve uptake from the interstitium by reducing non-specific interactions; however, the particles' increased stealth nature can also reduce internalization by phagocytic cells in areas having immature lymphocytes. The challenge of balancing these competing features has been met, however, and this application documents the creation of nanoparticles for effective lymphatic delivery to DCs and other APCs in lymph nodes. Some embodiments include a hydrophilic component, e.g., a layer of hydrophilic material. Examples of suitable hydrophilic materials are one or more of polyalkylene oxides, polyethylene oxides, polysaccharides, polyacrylic acids, and polyethers. The molecular weight of polymers in a layer can be adjusted to provide a useful degree of steric hindrance in vivo, e.g., from about 1,000 to about 100,000 or even more; artisans will immediately appreciate that all the ranges and values within the explicitly stated ranges are contemplated, e.g., between 10,000 and 50,000.

The nanoparticles may incorporate functional groups for further reaction. Functional groups for further reaction include electrophiles or nucleophiles; these are convenient for reacting with other molecules. Examples of nucleophiles are primary amines, thiols, and hydroxyls. Examples of electrophiles are succinimidyl esters, aldehydes, isocyanates, and maleimides.

A great variety of means, well known in the art, may be used to conjugate antigenic peptides and proteins to carriers. These methods include any standard chemistries which do not destroy or severely limit the biological activity of the antigen peptides and proteins, and which allow for a sufficient number of antigen peptides and proteins to be conjugated to the carrier in an orientation which allows for interaction of the antigen peptide or protein with a cognate T cell receptor. Generally, methods are preferred which conjugate the C-terminal regions of an antigen peptide or protein, or the C-terminal regions of an antigen peptide or protein fusion protein, to the earner. The exact chemistries will, of course, depend upon the nature of the earner material, the presence or absence of C-terminal fusions to the antigen peptide or protein, and/or the presence or absence of conjugating moieties.

Functional groups can be located on the particle as needed for availability. One location can be as side groups or termini on the core polymer or polymers that are layers on a core or polymers otherwise tethered to the particle. For instance, examples are included herein that describe PEG stabilizing the nanoparticles that can be readily functionalized for specific cell targeting or protein and peptide drug delivery.

Conjugates such as ethylene carbodiimide (ECDI), hexamethylene diisocyanate, propyleneglycol di-glycidylether which contain 2 epoxy residues, and epichlorohydrin may be used for fixation of peptides or proteins to the carrier surface. Without being bound by theory, ECDI is suspected of carrying out two major functions for induction of tolerance: (a) it chemically couples the protein/peptides to the cell surface via catalysis of peptide bond formation between free amino and free carboxyl groups; and (b) it induces the carrier to mimic apoptotic cell death such that they are picked up by host antigen presenting cells (which may include endothelial cells) in the spleen and induce tolerance. It is this presentation to host T-cells in a non-immunogenic fashion that leads to direct induction of anergy in autoreactive cells. In addition, ECDI serves as a potent stimulus for the induction of specific regulatory T cells.

In one series of embodiments, the antigen peptides and proteins are bound to the carrier via a covalent chemical bond. For example, a reactive group or moiety near the C-terminus of the antigen (e.g., the C-terminal carboxyl group, or a hydroxyl, thiol, or amine group from an amino acid side chain) may be conjugated directly to a reactive group or moiety on the surface of the carrier (e.g., a hydroxyl or carboxyl group of a PLA or PGA polymer, a terminal amine or carboxyl group of a dendrimer, or a hydroxyl, carboxyl or phosphate group of a phospholipid) by direct chemical reaction. Alternatively, there may be a conjugating moiety which covalently conjugates to both the antigen peptides and proteins and the carrier, thereby linking them together.

Reactive carboxyl groups on the surface of a carrier may be joined to free amines (e.g., from Lys residues) on the antigen peptide or protein, by reacting them with, for example, 1-ethyl-3-[3,9-dimethyl aminopropyl] carbodiimide hydrochloride (EDC) or N-hydroxysuccinimide ester (NHS). Similarly, the same chemistry may be used to conjugate free amines on the surface of a carrier with free carboxyls (e.g., from the C-terminus, or from Asp or Glu residues) on the antigen peptide or protein. Alternatively, free amine groups on the surface of a carrier may be covalently bound to antigen peptides and proteins, or antigen peptide or protein fusion proteins, using sulfo-SIAB chemistry, essentially as described by Arano et al. (1991) Chem. 2:71-6.

In another embodiment, a non-covalent bond between a ligand bound to the antigen peptide or protein and an anti-ligand attached to the carrier may conjugate the antigen to the carrier. For example, a biotin ligase recognition sequence tag may be joined to the C-terminus of an antigen peptide or protein, and this tag may be biotinylated by biotin ligase. The biotin may then serve as a ligand to non-covalently conjugate the antigen peptide or protein to avidin or streptavidin which is adsorbed or otherwise bound to the surface of the carrier as an anti-ligand. Alternatively, if the antigen peptides and proteins are fused to an immunoglobulin domain bearing an Fc region, as described above, the Fc domain may act as a ligand, and protein A, either covalently or non-covalently bound to the surface of the carrier, may serve as the anti-ligand to non-covalently conjugate the antigen peptide or protein to the carrier. Other means are well known in the art which may be employed to non-covalently conjugate antigen peptides and proteins to carriers, including metal ion chelation techniques (e.g., using a poly-His tag at the C-terminus of the antigen peptide or protein or antigen peptide or protein fusion proteins, and a Nit-coated carrier), and these methods may be substituted for those described here.

Conjugation of a nucleic acid moiety to a platform molecule can be effected in any number of ways, typically involving one or more crosslinking agents and functional groups on the nucleic acid moiety and platform molecule. Linking groups are added to platforms using standard synthetic chemistry techniques. Linking groups can be added to nucleic acid moieties using standard synthetic techniques. The practitioner has a number of choices for antigens used in the combinations of this invention. The inducing antigen present in the combination contributes to the specificity of the tolerogenic response that is induced. It may or may not be the same as the target antigen, which is the antigen present or to be placed in the subject being treated which is a target for the unwanted immunological response, and for which tolerance is desired.

An inducing antigen of this invention may be a polypeptide, polynucleotide, carbohydrate, glycolipid, or other molecule isolated from a biological source, or it may be a chemically synthesized small molecule, polymer, or derivative of a biological material, providing it has the ability to induce tolerance according to this description when combined with the mucosal binding component.

In some embodiments, the present invention provides a carrier (e.g., immune modifying particle) coupled to one or more peptides, polypeptides, and/or proteins. In some embodiments, a carrier (e.g., PLG carrier), such as those described herein, are effective to induce antigen-specific tolerance and/or prevent the onset of an immune related disease (such as EAE in a mouse model) and/or diminish the severity of a pre-existing immune related disease. In some embodiments, the compositions and methods of the present invention can cause T cells to undertake early events associated with T-cell activation, but do not allow T-cells to acquire effector function. For example, administration of compositions of the present invention can result in T-cells having a quasi-activated phenotype, such as CD69 and/or CD44 upregulation, but do not display effector function, such as indicated by a lack of IFN-γ or IL-17 synthesis. In some embodiments, administration of compositions of the present invention results in T-cells having a quasi-activated phenotype without having conversion of naive antigen-specific T-cells to a regulatory phenotype, such as those having $CD25^+/Foxp3^+$ phenotypes.

In some embodiments, the surface of a carrier (e.g., particle) comprises chemical moieties and/or functional groups that allow attachment (e.g., covalently, non-covalently) of antigenic peptides and/or other functional elements to the carrier. In some embodiments, the number, orientation, spacing, etc. of chemical moieties and/or functional groups on the carrier (e.g., particle) vary according to carrier chemistry, desired application, etc.

In some embodiments, a carrier comprises one or more biological or chemical agents adhered to, adsorbed on, encapsulated within, and/or contained throughout the carrier. In some embodiments, a chemical or biological agent is encapsulated in and/or contained throughout the particles. The present invention is not limited by the nature of the chemical or biological agents. Such agents include, but are not limited to, proteins, nucleic acid molecules, small molecule drugs, lipids, carbohydrates, cells, cell components, and the like. In some embodiments, two or more (e.g., 3, 4, 5, etc.) different chemical or biological agents are included on or within the carrier. In some embodiments, agents are configured for specific release rates. In some embodiments, multiple different agents are configured for different release rates. For example, a first agent may release over a period of hours while a second agent releases over a longer period of time (e.g., days, weeks, months, etc.). In some embodiments, the carrier or a portion thereof is configured for slow-release of biological or chemical agents. In some embodiments, the slow release provides release of biologically active amounts of the agent over a period of at least 30 days (e.g., 40 days, 50 days, 60 days, 70 days, 80 days, 90 days, 100 days, 180 days, etc.). In some embodiments, the carrier or a portion thereof is configured to be sufficiently porous to permit ingrowth of cells into the pores. The size of the pores may be selected for particular cell types of interest and/or for the amount of ingrowth desired. In some embodiments, the particles comprise the antigen of interest without other non-peptide active agents, such as drugs or immunomodulators. Furthermore, in some embodiments the particles of the invention do not contain immunostimulatory or immunosuppressive peptides in addition to the antigen of interest. Furthermore, in some embodiments, the particles do not contain other proteins or peptides (e.g. costimulatory molecules, MHC molecules, immunostimulatory peptides or immunosuppressive peptides) either on the surface or encapsulated within the particle.

Encapsulation of the antigen, biological, and/or chemical agents in the particle of the invention has been surprisingly found to induce immunological tolerance and has several advantages. First, the encapsulated particles have a slower cytokine response. Second, when using multiple antigens, biological, and/or chemical agents, encapsulation removes the competition between these various molecules that might occur if the agents were attached to the surface of the particle. Third, encapsulation allows more antigens, biological, and/or chemical agents to be incorporated with the particle. Fourth, encapsulation allows for easier use of complex protein antigens or organ homogenates (e.g. pancreas homogenate for type 1 diabetes or peanut extract in peanut allergy). Finally, encapsulation of antigens, biological, and/or chemical agents within the particle instead of conjugation to the surface of the particle maintains the net negative charge on the surface of the particle. The encapsulation of the antigen, biological, and/or chemical agents in the particles of the invention may be performed by any method known in the art. In one embodiment, polypeptide antigens are encapsulated in the particles by a double-emulsion process. In a further embodiment, the polypeptide antigens are water soluble.

In another embodiment, the polypeptide antigens are encapsulated in the particles by a single-emulsion process. In a further embodiment, the polypeptide antigens are more hydrophobic. Sometimes, the double emulsion process leads to the formation of large particles which may result in the leakage of the hydrophilic active component and low entrapment efficiencies. The coalescence and Ostwald ripening are two mechanisms that may destabilize the double-emulsion droplet, and the diffusion through the organic phase of the hydrophilic active component is the main mechanism responsible of low levels of entrapped active component. In some embodiments, it may be beneficial to reduce the nanoparticle size. One strategy to accomplish this is to apply a second strong shear rate. The leakage effect can be reduced by using a high polymer concentration and a high polymer molecular mass, accompanied by an increase in the viscosity of the inner water phase and in increase in the surfactant molecular mass.

In certain embodiments, the present invention provides carriers having thereon (or therein) cells or other biological or chemical agents. Where cells are employed, the carriers are not limited to a particular type of cells. In some embodiments, the carriers have thereon pancreatic islet cells. In some embodiments, the microporous carriers additionally have thereon ECM proteins and/or exendin-4. The carriers are not limited to a particular type. In some embodiments, a carrier has regions of varying porosity (e.g., varying pore size, pore depth, and/or pore density). In some embodiments, carriers have thereon (or therein) pharmaceutical agents, DNA, RNA, extracellular matrix proteins, exendin-4, etc. In certain embodiments, the present invention provides methods for transplanting pancreatic islet cells with such carriers. In certain embodiments of this invention, the inducing antigen is a single isolated or recombinantly produced molecule. For treating conditions where the target antigen is disseminated to various locations in the host, it is generally necessary that the inducing antigen be identical to or immunologically related to the target antigen. Examples of such antigens are most polynucleotide antigens, and some carbohydrate antigens (such as blood group antigens).

Any suitable antigens may find use within the scope of the present invention. In some embodiments, the inducing antigen contributes to the specificity of the tolerogenic response that is induced. The inducing antigen may or may not be the same as the target antigen, which is the antigen present or to be placed in the subject being treated which is a target for the unwanted immunological response, and for which tolerance is desired.

Where the target antigen is preferentially expressed on a particular organ, cell, or tissue type, the practitioner again has the option of using an inducing antigen which is identical with or immunologically related to the target antigen. However, there is also the additional option of using an antigen which is a bystander for the target. This is an antigen which may not be immunologically related to the target antigen, but is preferentially expressed in a tissue where the target antigen is expressed. A working theory as to the effectiveness of bystander suppression is that suppression is an active cell-mediated process that down-regulates the effector arm of the immune response at the target cells. The suppressor cells are specifically stimulated by the inducer antigen at the mucosal surface, and home to a tissue site where the bystander antigen is preferentially expressed. Through an interactive or cytokine-mediated mechanism, the localized suppressor cells then down-regulate effector cells (or inducers of effector cells) in the neighborhood, regardless of what they are reactive against. If the effector cells are specific for a target different from the inducing antigen, then the result is a bystander effect. For further elaboration of the bystander reaction and a list of tolerogenic peptides having this effect, the reader is referred to International Patent Publication WO 93/16724. An implication of bystander theory is that one of ordinary skill need not identify or isolate a particular target antigen against which tolerance is desired in order to practice the present invention. The practitioner need only be able to obtain at least one molecule preferentially expressed at the target site for use as an inducing antigen.

In certain embodiments of this invention, the inducing antigen is not in the same form as expressed in the individual being treated, but is a fragment or derivative thereof. Inducing antigens of this invention include peptides based on a molecule of the appropriate specificity but adapted by fragmentation, residue substitution, labeling, conjugation, and/or fusion with peptides having other functional properties. The adaptation may be performed for any desirable purposes, including but not limited to the elimination of any undesirable property, such as toxicity or immunogenicity; or to enhance any desirable property, such as mucosal binding, mucosal penetration, or stimulation of the tolerogenic arm of the immune response. Terms such as insulin peptide, collagen peptide, and myelin basic protein peptide, as used herein, refer not only to the intact subunit, but also to allotypic and synthetic variants, fragments, fusion peptides, conjugates, and other derivatives that contain a region that is homologous (preferably 70% identical, more preferably 80% identical and even more preferably 90% identical at the amino acid level) to at least 10 and preferably 20 consecutive amino acids of the respective molecule for which it is an analog, wherein the homologous region of the derivative shares with the respective parent molecule an ability to induce tolerance to the target antigen.

It is recognized that tolerogenic regions of an inducing antigen are often different from immunodominant epitopes for the stimulation of an antibody response. Tolerogenic regions are generally regions that can be presented in particular cellular interactions involving T cells. Tolerogenic regions may be present and capable of inducing tolerance upon presentation of the intact antigen. Some antigens contain cryptic tolerogenic regions, in that the processing and presentation of the native antigen does not normally trigger tolerance. An elaboration of cryptic antigens and their identification is found in International Patent Publication WO 94/27634.

In certain embodiments of this invention, two, three, or a higher plurality of inducing antigens is used. It may be desirable to implement these embodiments when there are a plurality of target antigens, or to provide a plurality of bystanders for the target. For example, both insulin and glucagon can be mixed with a mucosal binding component in the treatment of diabetes. It may also be desirable to provide a cocktail of antigens to cover several possible alternative targets. For example, a cocktail of histocompatibility antigen fragments could be used to tolerize a subject in anticipation of future transplantation with an allograft of unknown phenotype. Allovariant regions of human leukocyte antigens are known in the art: e.g., Immunogenetics 29:231, 1989. In another example, a mixture of allergens may serve as inducing antigen for the treatment of atopy.

Inducing antigens can be prepared by a number of techniques known in the art, depending on the nature of the molecule. Polynucleotide, polypeptide, and carbohydrate antigens can be isolated from cells of the species to be treated in which they are enriched. Short peptides are conveniently prepared by amino acid synthesis. Longer proteins of known sequence can be prepared by synthesizing an encoding sequence or PCR-amplifying an encoding sequence from a natural source or vector, and then expressing the encoding sequence in a suitable bacterial or eukaryotic host cell.

In certain embodiments of this invention, the combination comprises a complex mixture of antigens obtained from a cell or tissue, one or more of which plays the role of inducing antigen. The antigens may be in the form of whole cells, either intact or treated with a fixative such as formaldehyde, glutaraldehyde, or alcohol. The antigens may be in the form of a cell lysate, created by detergent solubilization or mechanical rupture of cells or tissue, followed by clarification. The antigens may also be obtained by subcellular fractionation, particularly an enrichment of plasma membrane by techniques such as differential centrifugation, optionally followed by detergent solubilization and dialysis. Other separation techniques are also suitable, such as affinity or ion exchange chromatography of solubilized membrane proteins.

In one embodiment, the antigenic peptide or protein is an autoantigen, an alloantigen or a transplantation antigen. In yet another particular embodiment, the autoantigen is selected from the group consisting of myelin basic protein, collagen or fragments thereof, DNA, nuclear and nucleolar proteins, mitochondrial proteins and pancreatic (3-cell proteins.

The invention provides for the induction of tolerance to an autoantigen for the treatment of autoimmune diseases by administering the antigen for which tolerance is desired. For example, autoantibodies directed against the myelin basic protein (MBP) are observed in patients with multiple sclerosis, and, accordingly, MBP antigenic peptides or proteins may be used in the invention to be delivered using the compositions of the present invention to treat and prevent multiple sclerosis.

By way of another non-limiting example, an individual who is a candidate for a transplant from a non-identical twin may suffer from rejection of the engrafted cells, tissues or organs, as the engrafted antigens are foreign to the recipient. Prior tolerance of the recipient individual to the intended graft abrogates or reduces later rejection. Reduction or elimination of chronic anti-rejection therapies may be achieved by the practice of the present invention. In another example, many autoimmune diseases are characterized by a cellular immune response to an endogenous or self antigen. Tolerance of the immune system to the endogenous antigen is desirable to control the disease.

In a further example, sensitization of an individual to an industrial pollutant or chemical, such as may be encountered on-the-job, presents a hazard of an immune response. Prior tolerance of the individual's immune system to the chemical, in particular in the form of the chemical reacted with the individual's endogenous proteins, may be desirable to prevent the later occupational development of an immune response.

Allergens are other antigens for which tolerance of the immune response thereto is also desirable. In one embodiment, the antigen is a gliaden. In a further embodiment, the antigen is A-gliaden.

Notably, even in diseases where the pathogenic autoantigen is unknown, bystander suppression may be induced using antigens present in the anatomical vicinity. For example, autoantibodies to collagen are observed in rheumatoid arthritis and, accordingly, a collagen-encoding gene may be utilized as the antigen-expressing gene module in order to treat rheumatoid arthritis (see e.g. Choy (2000) Curr Opin Investig Drugs 1: 58-62). Furthermore, tolerance to beta cell autoantigens may be utilized to prevent development of type 1 diabetes (see e.g. Bach and Chatenoud (2001) Ann Rev Immunol 19: 131-161).

As another example, auto-antibodies directed against myelin oligodendrocyte glycoprotein (MOG) are observed in autoimmune encephalomyelitis and in many other CNS diseases as well as multiple sclerosis (see e.g. Iglesias et al. (2001) Glia 36: 22-34). Accordingly, use of MOG antigen expressing constructs in the invention allows for treatment of multiple sclerosis as well as related autoimmune disorders of the central nervous system.

Still other examples of candidate autoantigens for use in treating autoimmune disease include: pancreatic beta-cell antigens, insulin and GAD to treat insulin-dependent diabetes mellitus; collagen type 11, human cartilage gp 39 (HCgp39) and gp130-RAPS for use in treating rheumatoid arthritis; myelin basic protein (MBP), proteo lipid protein (PLP) and myelin oligodendrocyte glycoprotein (MOG, see above) to treat multiple sclerosis; fibrillarin, and small nucleolar protein (snoRNP) to treat scleroderma; thyroid stimulating factor receptor (TSH-R) for use in treating Graves' disease; nuclear antigens, histones, glycoprotein gp70 and ribosomal proteins for use in treating systemic lupus erythematosus; pyruvate dehydrogenase dehydrolipoamide acetyltransferase (PCD-E2) for use in treating primary billiary cirrhosis; hair follicle antigens for use in treating alopecia areata; and human tropomyosin isoform 5 (hTM5) for use in treating ulcerative colitis.

In one embodiment, the particles of the invention are coupled to antigens comprising one or more epitopes associated with allergies, autoimmune diseases and/or inflammatory diseases or disorders. The antigens may comprise one or more copies of an epitope. In one embodiment, the antigens comprise a single epitope associated with one disease or disorder. In a further embodiment, the antigens comprise more than one epitope associated with the same disease or disorder. In yet a further embodiment, the antigens comprise more than one epitope associated with different diseases or disorders. In a further embodiment, the antigens comprise one or more epitopes associated with one or more allergies. In a further embodiment, the antigens comprise one or more epitopes associated with multiple sclerosis, type 1 diabetes. Celiac's disease, and/or inflammatory bowel disease, including Crohn's disease or ulcerative colitis. In one embodiment, the epitopes are from myelin basic protein (e.g. SEQ ID NOs:4975 & 4976), proteolipid protein (e.g. SEQ ID NO: 4977), myelin oligodendrocyte glycoprotein (e.g. SEQ ID NOs: 1 & 4978), aquaporin, (e.g. SEQ ID NO: 4979), myelin associated glycoprotein (e.g. SEQ ID NO: 4980), insulin (e.g. SEQ ID NO: 4981), glutamic acid decarboxylase (e.g. SEQ ID NO: 4982), gliadin (e.g. SEQ ID NOs:4983-4985 or 5136-5140), the α3 chain of type IV collagen (e.g. SEQ ID NO: 5017), or fragments, homologs, or isoforms thereof. In a further embodiment, the epitopes are from gluten, including from gliadin and/or glutenin. In one embodiment, the epitopes are from insulin homologs, such as those described in U.S. Pat. No. 8,476,228 hereby incorporated in its entirety for all purposes. In one embodiment, the gliaden epitopes are SEQ ID NOs: 13, 14, 16, 320, or 321 in U.S. Application No. 20110293644, hereby incorporated in its entirety for all purposes.

Further non-limiting examples of epitopes associated with various autoimmune diseases and/or inflammatory diseases or disorders that are contemplated by the instant invention are described in Tables 2 and 3.

TABLE 2

Representative Linear Epitopes

| Disease | Representative Epitopes |
|---|---|
| Multiple Sclerosis | SEQ ID NOs: 2-1294 |
| Celiac Disease | SEQ ID NOs: 1295-1724; |
|  | SEQ ID NOs: 1726-1766; |
|  | SEQ ID NOs: 4986-5140 |
| Diabetes | SEQ ID NOs: 1767-1840; |
|  | SEQ ID NOs: 1842-1962; |
|  | SEQ ID NOs: 1964-2027; |
|  | SEQ ID NOs: 2029-2073; |
|  | SEQ ID NOs: 2075-2113; |
|  | SEQ ID NOs: 2115-2197; |
|  | SEQ ID NOs: 2199-2248; |
|  | SEQ ID NOs: 2250-2259; |
|  | SEQ ID NOs: 2261-2420; |
|  | SEQ ID NOs: 2422-2486; |
|  | SEQ ID NOs: 2489-2505 |
| Rheumatoid Arthritis | SEQ ID NOs: 2506-3260; |
|  | SEQ ID NOs: 3262-3693 |
| Systemic Lupus Erythematosus | SEQ ID NOs: 3694-3857; |
|  | SEQ ID NOs: 3860-4565 |
| Good Pasture's Syndrome | SEQ ID NOs: 4566-4576; |
|  | SEQ ID NOs: 4578-4610; |
|  | SEQ ID NOs: 4612-4613; |
|  | SEQ ID NOs: 5018-5039 |
| Autoimmune Uveitis | SEQ ID NOs: 4614-4653 |
| Autoimmune Thyroiditis | SEQ ID NOs: 4654-4694; |
|  | SEQ ID NOs: 4696-4894; |
|  | SEQ ID NOs: 4896-4901 |
| Autoimmune Myositis | SEQ ID NOs: 4902-4906 |
| Autoimmune Vasculitis | SEQ ID NOs: 4907-4914 |
| Autoimmune Pancreatitis | SEQ ID NOs: 4915-4917 |
| Crohns Disease | SEQ ID NOs: 4918-4941 |
| Ulcerative Colitis | SEQ ID NOs: 4942-4952 |
| Psoriasis | SEQ ID NOs: 4953-4963 |
| Reactive Arthritis | SEQ ID NOs: 4964-4974 |

Not all epitopes are linear epitopes; epitopes can also be discontinuous, conformational epitopes. A number of discontinuous epitopes associated with autoimmune diseases or inflammatory diseases and/or disorders are known. Non-limiting examples of discontinuous epitopes are described in Table 3.

TABLE 3

Representative Discontinuous Epitopes

| Disease | Epitope | Full Length Polypeptide |
|---|---|---|
| Celiac Disease | D151, E153, E154, E155, E158; | Protein-glutamine gamma-glutamyltransferase 2 |
|  | D306, N308, N310; | SEQ ID NO: 1725 |

TABLE 3-continued

Representative Discontinuous Epitopes

| Disease | Epitope | Full Length Polypeptide |
|---|---|---|
| | D434, E435, E437, D438;<br>E329;<br>E153;<br>R19, E153, M659; or<br>C277, H335, D358 | |
| Diabetes | E517;<br>R255, F256, K257, K263,<br>E264, K265, L270, P271,<br>R272, L273, L285, K286,<br>K287, I294, G295, T296,<br>D297, S298, R317, R318;<br>N483, I484, I485, K486,<br>N487, R488, E489, G490,<br>Y491, E492, M493, V494,<br>F495, D496, G497, K498,<br>P499, F556, F557, R558,<br>M559, V560, I561, S562,<br>N563, P564, A565, A566,<br>T567, H568, Q569, D570,<br>I571, D572, F573, L574,<br>I575, E576, E577, I578,<br>E579, R580, L581, G582,<br>Q583, D584, L585;<br>E264;<br>E517, E520, E521, S524,<br>S527, V532;<br>E517, E521;<br>K358;<br>R536, Y540 | Glutamate decarboxylase 2<br>SEQ ID NOs: 1841, 1963,<br>2114, & 2249 |
| Diabetes | P876, A877, E878, T880;<br>T804;<br>T804, V813, D821, R822,<br>Q862, P886;<br>T804, V813, D821, R822,<br>Q862, P886;<br>W799, E836, N858;<br>D911;<br>Q862;<br>L831, H833, V834, E836,<br>Q860;<br>W799, E836, N858;<br>W799, L831, H833, V834,<br>Y835, E836, Q860; | protein tyrosine phosphatase,<br>receptor type, N precursor<br>SEQ ID NOs: 2028 & 2074 |
| Diabetes | R325, R332, E333, K336,<br>K340;<br>R325;<br>W325 | zinc transporter 8 isoform a<br>SEQ ID NO: 2421 |
| Diabetes | E872, C945 | Receptor-type tyrosine-<br>protein phosphatase N2<br>SEQ ID NOs: 2198, 2260, &<br>2487 |
| Diabetes | W799, C909 | tyrosine phosphatase<br>SEQ ID NO: 2488 |
| Rheumatoid Arthritis | L14, M15, I16, S17, R18,<br>N147, G148, S187, M191,<br>H196, N197, H198, Y199,<br>Q201, S203 | Chain A, Crystal Structure Of<br>A Human Igm Rheumatoid<br>Factor Fab In Complex With<br>Its Autoantigen Igg Fc<br>SEQ ID NO: 3261 |
| Systemic Lupus<br>Erythematosus | K591, S592, G593 | ATP-dependent DNA<br>helicase 2 subunit 1<br>SEQ ID NO: 3858 |
| Systemic Lupus<br>Erythematosus | M1, K2, L3, V4, R5, F6, L7,<br>M8, K9, L10, S11, H12,<br>E13, T14, V15, T16, I17,<br>E18, L19, K20, N21, G22,<br>T23, Q24, V25, H26, P85,<br>K86, V87, K88, S89, K90,<br>K91, R92, E93, A94, V95,<br>A96, G97, R98, G99, R100,<br>G101, R102, G103, R104,<br>G105, R106, G107, R108,<br>G109, R110, G111, R112,<br>G113, R114, G115, G116,<br>P117, R118, R119 | Small nuclear<br>ribonucleoprotein Sm D1<br>SEQ ID NO: 3859 |

TABLE 3-continued

Representative Discontinuous Epitopes

| Disease | Epitope | Full Length Polypeptide |
| --- | --- | --- |
| Systemic Lupus Erythematosus | G59, R62 | beta-2-glycoprotein I<br>SEQ ID NO: 4357 |
| Good Pasture's Syndrome | T24, A25, I26, S28, E31, V34, P35, S38, Q64 | type IV collagen alpha3 chain<br>SEQ ID NO: 4577 |
| Good Pasture's Syndrome | T1455, A1456, I1457, S1459, E1462, T1464, V1465, P1466, Y1468, S1469, Q1495, T1537, T1565, P1569, H1572, K1579, A1634 | alpha3 type IV collagen<br>SEQ ID NO: 4611 |
| Autoimmune Thyroiditis | E604, D620, K627, D630;<br>R225, R646, D707;<br>K627;<br>R225;<br>Y772;<br>K713, F714, P715, E716;<br>P715, D717 | Thyroid peroxidase<br>SEQ ID NO: 4695 |
| Autoimmune Thyroiditis | D36, R38, K42, Q55, K58, I60, E61, R80, Y82, S84, T104, H105, E107, R109, N110, K129, F130, D151, F153, I155, E157, T181, K183, D203 | Thyrotropin receptor<br>SEQ ID NO: 4895 |

Combinations of antigens and/or epitopes can be tested for their ability to promote tolerance by conducting experiments with isolated cells or in animal models.

In some embodiments, the tolerance inducing compositions of the present invention contain an apoptosis signaling molecule (e.g., in addition to an antigenic peptide or other antigenic molecule). In some embodiments, the apoptosis signaling molecule is coupled and/or associated with the surface of the carrier. In some embodiments an apoptotic signaling molecules allows a carrier to be perceived as an apoptotic body by antigen presenting cells of the host, such as cells of the host reticuloendothelial system; this allows presentation of the associated peptide epitopes in a tolerance-inducing manner. Without being bound by theory, this is presumed to prevent the upregulation of molecules involved in immune cell stimulation, such as MHC class I/II, and costimulatory molecules. These apoptosis signaling molecules may also serve as phagocytic markers. For example, apoptosis signaling molecules suitable for the present invention have been described in US Pat App No. 20050113297, which is hereby incorporated by reference in its entirety. Molecules suitable for the present invention include molecules that target phagocytes, which include macrophages, dendritic cells, monocytes, granulocytes and neutrophils.

In some embodiments, molecules suitable as apoptotic signalling molecules act to enhance tolerance of the associated peptides. Additionally, a carrier bound to an apoptotic signaling molecule can be bound by C1q in apoptotic cell recognition (Paidassi et al., (2008) J. Immunol. 180:2329-2338; herein incorporated by reference in its entirety). For example, molecules that may be useful as apoptotic signalling molecules include phosphatidyl serine, annexin-1, annexin-5, milk fat globule-EGF-factor 8 (MFG-E8), or the family of thrombospondins (e.g., thrombospondin-1 (TSP-1)). Various molecules suitable for use as apoptotic signalling molecules with the present invention are discussed, for example, in U.S. Pat. App. 2012/0076831; herein incorporated by reference in its entirety).

In some embodiments, the apoptotic signalling molecule may be conjugated to the antigen-specific peptide. In some instances, the apoptotic signalling molecule and antigen-specific peptide are conjugated by the creation of a fusion protein. For example a fusion protein may comprise at least one antigen-specific peptide (or a fragment or a variant thereof) coupled to at least one molecule of an apoptotic signalling molecule (or a fragment or a variant thereof). For the creation of fusion proteins, the terms "fusion protein," "fusion peptide," "fusion polypeptide," and "chimeric peptide" are used interchangably. Suitable fragments of the antigen-specific peptide include any fragment of the full-length peptide that retains the function of generating the desired antigen-specific tolerance function of the present invention. The fusion protein may be created by various means understood in the art (e.g., genetic fusion, chemical conjugation, etc.). The two proteins may be fused either directly or via an amino acid linker. The polypeptides forming the fusion protein are typically linked C-terminus to N-terminus, although they can also be linked C-terminus to C-terminus, N-terminus to N-terminus, or N-terminus to C-terminus. The polypeptides of the fusion protein can be in any order. A peptide linker sequence may be employed to separate the first and second polypeptide components by a distance sufficient to ensure that each polypeptide folds into its secondary and tertiary structures. Amino acid sequences which may be usefully employed as linkers include those disclosed in Maratea et. al., Gene 40:39-46 (1985); Murphy et al., Proc. Natl. Acad. Sci. USA 83:8258-8262 (1986); U.S. Pat. Nos. 4,935,233 and 4,751,180; herein incorporated by reference in their entireties. The linker sequence may generally be from 1 to about 50 amino acids in length. In some embodiments, linker sequences are not required and/or utilized, for example, when the first and second polypeptides have non-essential N-terminal amino acid regions that can be used to separate the functional domains and prevent steric interference.

A proxy for tolerogenic activity is the ability of an intact antigen or fragment to stimulate the production of an appropriate cytokine at the target site. The immunoregulatory cytokine released by T suppressor cells at the target site is thought to be TGF-β (Miller et al., Proc. Natl. Acad. Sci. USA 89:421, 1992). Other factors that may be produced during tolerance are the cytokines IL4 and IL-10, and the mediator PGE. In contrast, lymphocytes in tissues undergoing active immune destruction secrete cytokines such as IL-I, IL-2, IL-6, and γ-IFN. Hence, the efficacy of a candidate inducing antigen can be evaluated by measuring its ability to stimulate the appropriate type of cytokines.

With this in mind, a rapid screening test for tolerogenic epitopes of the inducing antigen, effective mucosal binding components, effective combinations, or effective modes and schedules of mucosal administration can be conducted using syngeneic animals as donors for in vitro cell assays. Animals are treated at a mucosal surface with the test composition, and at some time are challenged with parenteral administration of the target antigen in complete Freund's adjuvant. Spleen cells are isolated, and cultured in vitro in the presence of the target antigen at a concentration of about 50 μg/mL. Target antigen can be substituted with candidate proteins or sub-fragments to map the location of tolerogenic epitopes. Cytokine secretion into the medium can be quantitated by standard immunoassay.

The ability of the cells to suppress the activity of other cells can be determined using cells isolated from an animal immunized with the target antigen, or by creating a cell line responsive to the target antigen (Ben-Nun et al., Eur. J. Immunol. 11:195, 1981, herein incorporated by reference in its entirety). In one variation of this experiment, the suppressor cell population is mildly irradiated (about 1000 to 1250 rads) to prevent proliferation, the suppressors are co-cultured with the responder cells, and then tritiated thymidine incorporation (or MTT) is used to quantitate the proliferative activity of the responders. In another variation, the suppressor cell population and the responder cell population are cultured in the upper and lower levels of a dual chamber transwell culture system (Costar, Cambridge Mass.), which permits the populations to coincubate within 1 mm of each other, separated by a polycarbonate membrane (WO 93/16724). In this approach, irradiation of the suppressor cell population is unnecessary, since the proliferative activity of the responders can be measured separately.

In embodiments of the invention where the target antigen is already present in the individual, there is no need to isolate the antigen or precombine it with the mucosal binding component. For example, the antigen may be expressed in the individual in a certain fashion as a result of a pathological condition (such as inflammatory bowel disease or Celiac disease) or through digestion of a food allergen. Testing is performed by giving the mucosal binding component in one or more doses or formulations, and determining its ability to promote tolerization against the antigen in situ.

The effectiveness of compositions and modes of administration for treatment of specific disease can also be elaborated in a corresponding animal disease model. The ability of the treatment to diminish or delay the symptomatology of the disease is monitored at the level of circulating biochemical and immunological hallmarks of the disease, immunohistology of the affected tissue, and gross clinical features as appropriate for the model being employed. Non-limiting examples of animal models that can be used for testing are included in the following section.

The invention contemplates modulation of tolerance by modulating TH1 response, TH2 response, TH17 response, or a combination of these responses. Modulating TH1 response encompasses changing expression of, e.g., interferon-gamma. Modulating TH2 response encompasses changing expression of, e.g., any combination of IL-4, IL-5, IL-10, and IL-13. Typically an increase (decrease) in TH2 response will comprise an increase (decrease) in expression of at least one of IL-4, IL-5, IL-10, or IL-13; more typically an increase (decrease) in TH2 response will comprise an increase in expression of at least two of IL-4, IL-5, IL-10, or EL-13, most typically an increase (decrease) in TH2 response will comprise an increase in at least three of DL-4, IL-5, IL-10, or IL-13, while ideally an increase (decrease) in TH2 response will comprise an increase (decrease) in expression of all of IL-4, IL-5, IL-10, and IL-13. Modulating TH 17 encompasses changing expression of, e.g., TGF-beta, IL-6, IL-21 and IL23, and effects levels of IL-17, IL-21 and IL-22.

Other suitable methods for assessing the effectiveness of compositions and methods of the present invention are understood in the art, as are discussed, for example, in U.S. Pat. App. 2012/0076831 (herein incorporated by reference in its entirety).

Certain embodiments of this invention relate to priming of immune tolerance in an individual not previously tolerized by therapeutic intervention. These embodiments generally involve a plurality of administrations of a combination of antigen and mucosal binding component. Typically, at least three administrations, frequently at least four administrations, and sometimes at least six administrations are performed during priming in order to achieve a long-lasting result, although the subject may show manifestations of tolerance early in the course of treatment. Most often, each dose is given as a bolus administration, but sustained formulations capable of mucosal release are also suitable. Where multiple administrations are performed, the time between administrations is generally between 1 day and 3 weeks, and typically between about 3 days and 2 weeks. Generally, the same antigen and mucosal binding component are present at the same concentration, and the administration is given to the same mucosal surface, but variations of any of these variables during a course of treatment may be accommodated.

Other embodiments of this invention relate to boosting or extending the persistence of a previously established immune tolerance. These embodiments generally involve one administration or a short course of treatment at a time when the established tolerance is declining or at risk of declining. Boosting is generally performed 1 month to 1 year, and typically 2 to 6 months after priming or a previous boost. This invention also includes embodiments that involve regular maintenance of tolerance on a schedule of administrations that occur semiweekly, weekly, biweekly, or on any other regular schedule.

The particles of the current invention can be given in any dose effective to dampen the inflammatory immune response in a subject in need thereof or to treat a bacterial or viral infection in a subject in need thereof. In certain embodiments, about $10^2$ to about $10^{20}$ particles are provided to the individual. In a further embodiment between about $10^3$ to about $10^{15}$ particles are provided. In yet a further embodiment between about $10^6$ to about $10^{12}$ particles are provided. In still a further embodiment between about $10^8$ to about $10^{10}$ particles are provided. In a preferred embodiment the preferred dose is 0.1% solids/ml. Therefore, for 0.5 μm beads, a preferred dose is approximately $4 \times 10^9$ beads, for 0.05 μm beads, a preferred dose is approximately $4 \times 10^{12}$ beads, for 3 μm beads, a preferred dose is $2 \times 10^7$ beads. However, any dose that is effective in treating the particular condition to be treated is encompassed by the current invention.

The invention is useful for treatment of immune related disorders such as autoimmune disease, transplant rejection, enzyme deficiencies and allergic reactions. Substitution of a synthetic, biocompatible particle system to induce immune tolerance could lead to ease of manufacturing, broad availability of therapeutic agents, increase uniformity between samples, increase the number of potential treatment sites and dramatically reduce the potential for allergic responses to a carrier cell.

As used herein, the term "immune response" includes T cell mediated and/or B cell mediated immune responses. Exemplary immune responses include T cell responses, e.g., cytokine production and cellular cytotoxicity. In addition, the term immune response includes immune responses that are indirectly effected by T cell activation, e.g., antibody production (humoral responses) and activation of cytokine responsive cells, e.g., macrophages. Immune cells involved in the immune response include lymphocytes, such as B cells and T cells (CD4+, CD8+, Th1 and Th2 cells); antigen presenting cells (e.g., professional antigen presenting cells such as dendritic cells, macrophages, B lymphocytes, Langerhans cells, and nonprofessional antigen presenting cells such as keratinocytes, endothelial cells, astrocytes, fibroblasts, oligodendrocytes); natural killer cells; myeloid cells, such as macrophages, eosinophils, mast cells, basophils, and granulocytes. In some embodiments, the modified particles of the present invention are effective to reduce inflammatory cell trafficking to the site of inflammation.

As used herein, the term "anergy," "tolerance," or "antigen-specific tolerance" refers to insensitivity of T cells to T cell receptor-mediated stimulation. Such insensitivity is generally antigen-specific and persists after exposure to the antigenic peptide has ceased. For example, anergy in T cells is characterized by lack of cytokine production, e.g., IL-2. T-cell anergy occurs when T cells are exposed to antigen and receive a first signal (a T cell receptor or CD-3 mediated signal) in the absence of a second signal (a costimulatory signal). Under these conditions, re-exposure of the cells to the same antigen (even if re-exposure occurs in the presence of a costimulatory molecule) results in failure to produce cytokines and subsequently failure to proliferate. Thus, a failure to produce cytokines prevents proliferation. Anergic T cells can, however, proliferate if cultured with cytokines (e.g., IL-2). For example, T cell anergy can also be observed by the lack of IL-2 production by T lymphocytes as measured by ELISA or by a proliferation assay using an indicator cell line. Alternatively, a reporter gene construct can be used. For example, anergic T cells fail to initiate DL-2 gene transcription induced by a heterologous promoter under the control of the 5' IL-2 gene enhancer or by a multimer of the API sequence that can be found within the enhancer (Kang et al. 1992 Science. 257:1134).

As used herein, the term "immunological tolerance" refers to methods performed on a proportion of treated subjects in comparison with untreated subjects where: a) a decreased level of a specific immunological response (thought to be mediated at least in part by antigen-specific effector T lymphocytes, B lymphocytes, antibody, or their equivalents); b) a delay in the onset or progression of a specific immunological response; or c) a reduced risk of the onset or progression of a specific immunological response. "Specific" immunological tolerance occurs when immunological tolerance is preferentially invoked against certain antigens in comparison with others. "Non-Specific" immunological tolerance occurs when immunological tolerance is invoked indiscriminately against antigens which lead to an inflammatory immune response. "Quasi-Specific" immunological tolerance occurs when immunological tolerance is invoked semi-discriminately against antigens which lead to a pathogenic immune response but not to others which lead to a protective immune response.

Tolerance to autoantigens and autoimmune disease is achieved by a variety of mechanisms including negative selection of self-reactive T cells in the thymus and mechanisms of peripheral tolerance for those autoreactive T cells that escape thymic deletion and are found in the periphery. Examples of mechanisms that provide peripheral T cell tolerance include "ignorance" of self antigens, anergy or unresponsiveness to autoantigen, cytokine immune deviation, and activation-induced cell death of self-reactive T cells. In addition, regulatory T cells have been shown to be involved in mediating peripheral tolerance. See, for example, Walker et al. (2002) Nat. Rev. Immunol. 2: 11-19; Shevach et al. (2001) Immunol. Rev. 182:58-67. In some situations, peripheral tolerance to an autoantigen is lost (or broken) and an autoimmune response ensues. For example, in an animal model for EAE, activation of antigen presenting cells (APCs) through TLR innate immune receptors was shown to break self-tolerance and result in the induction of EAE (Waldner et al. (2004) J. Clin. Invest. 113:990-997).

Accordingly, in some embodiments, the invention provides methods for increasing antigen presentation while suppressing or reducing TLR7/8, TLR9, and/or TLR 7/8/9 dependent cell stimulation. As described herein, administration of particular modified particles results in antigen presentation by DCs or APCs while suppressing the TLR 7/8, TLR9, and/or TLR7/8/9 dependent cell responses associated with immunostimulatory polynucleotides. Such suppression may include decreased levels of one or more TLR-associated cytokines.

As discussed above this invention provides novel compounds that have biological properties useful for the treatment of Mac-1 and LFA-1 mediated disorders.

Accordingly, in another aspect of the present invention, pharmaceutical compositions are provided, which comprise the immune modifying particles and optionally comprise a pharmaceutically acceptable carrier. In certain embodiments, these compositions optionally further comprise one or more additional therapeutic agents. Alternatively, the modified particles of the current invention may be administered to a patient in need thereof in combination with the administration of one or more other therapeutic agents. For example, additional therapeutic agents for conjoint administration or inclusion in a pharmaceutical composition with a compound of this invention may be an approved anti-inflammatory agent, or it may be any one of a number of agents undergoing approval in the Food and Drug Administration that ultimately obtain approval for the treatment of any disorder characterized by an uncontrolled inflammatory immune response or a bacterial or viral infection. It will also be appreciated that certain of the modified particles of present invention can exist in free form for treatment, or where appropriate, as a pharmaceutically acceptable derivative thereof.

The pharmaceutical compositions of the present invention additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogenfree water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

The particles of the invention may be administered orally, nasally, intravenously, intramuscularly, ocularly, transdermally, intraperitoneally, or subcutaneously. In one embodiment, the particles of the invention are administered intravenously.

The effective amounts and method of administration of the present invention for modulation of an immune response can vary based on the individual, what condition is to be treated and other factors evident to one skilled in the art. Factors to be considered include route of administration and the number of doses to be administered. Such factors are known in the art and it is well within the skill of those in the art to make such determinations without undue experimentation. A suitable dosage range is one that provides the desired regulation of immune. Useful dosage ranges of the carrier, given in amounts of carrier delivered, may be, for example, from about any of the following: 0.5 to 10 mg/kg, 1 to 9 mg/kg, 2 to 8 mg/kg, 3 to 7 mg/kg, 4 to 6 mg/kg, 5 mg/kg, 1 to 10 mg/kg, 5 to 10 mg/kg. Alternatively, the dosage can be administered based on the number of particles. For example, useful dosages of the carrier, given in amounts of carrier delivered, may be, for example, about $10^6$, $10^7$, $10^8$, $10^9$, $10^{10}$, or greater number of particles per dose. The absolute amount given to each patient depends on pharmacological properties such as bioavailability, clearance rate and route of administration. Details of pharmaceutically acceptable carriers, diluents and excipients and methods of preparing pharmaceutical compositions and formulations are provided in Remmingtons Pharmaceutical Sciences $18^{th}$ Edition, 1990, Mack Publishing Co., Easton, Pa., USA., which is hereby incorporated by reference in its entirety.

The effective amount and method of administration of the particular carrier formulation can vary based on the individual patient, desired result and/or type of disorder, the stage of the disease and other factors evident to one skilled in the art. The route(s) of administration useful in a particular application are apparent to one of skill in the art. Routes of administration include but are not limited to topical, dermal, transdermal, transmucosal, epidermal, parenteral, gastrointestinal, and naso-pharyngeal and pulmonary, including transbronchial and transalveolar. A suitable dosage range is one that provides sufficient IRP-containing composition to attain a tissue concentration of about 1-50 μM as measured by blood levels. The absolute amount given to each patient depends on pharmacological properties such as bioavailability, clearance rate and route of administration.

The present invention provides carrier formulations suitable for topical application including, but not limited to, physiologically acceptable implants, ointments, creams, rinses and gels. Exemplary routes of dermal administration are those which are least invasive such as transdermal transmission, epidermal administration and subcutaneous injection.

Transdermal administration is accomplished by application of a cream, rinse, gel, etc. capable of allowing the carrier to penetrate the skin and enter the blood stream. Compositions suitable for transdermal administration include, but are not limited to, pharmaceutically acceptable suspensions, oils, creams and ointments applied directly to the skin or incorporated into a protective carrier such as a transdermal device (so-called "patch"). Examples of suitable creams, ointments etc. can be found, for instance, in the Physician's Desk Reference. Transdermal transmission may also be accomplished by iontophoresis, for example using commercially available patches which deliver their product continuously through unbroken skin for periods of several days or more. Use of this method allows for controlled transmission of pharmaceutical compositions in relatively great concentrations, permits infusion of combination drugs and allows for contemporaneous use of an absorption promoter.

Parenteral routes of administration include but are not limited to electrical (iontophoresis) or direct injection such as direct injection into a central venous line, intravenous, intramuscular, intraperitoneal, intradermal, or subcutaneous injection. Formulations of carrier suitable for parenteral administration are generally formulated in USP water or water for injection and may further comprise pH buffers, salts bulking agents, preservatives, and other pharmaceutically acceptable excipients. Immunoregulatory polynucleotide for parenteral injection may be formulated in pharmaceutically acceptable sterile isotonic solutions such as saline and phosphate buffered saline for injection.

Gastrointestinal routes of administration include, but are not limited to, ingestion and rectal routes and can include the use of, for example, pharmaceutically acceptable powders, pills or liquids for ingestion and suppositories for rectal administration.

Naso-pharyngeal and pulmonary administration include are accomplished by inhalation, and include delivery routes such as intranasal, transbronchial and transalveolar routes. The invention includes formulations of carrier suitable for administration by inhalation including, but not limited to, liquid suspensions for forming aerosols as well as powder forms for dry powder inhalation delivery systems. Devices suitable for administration by inhalation of carrier formulations include, but are not limited to, atomizers, vaporizers, nebulizers, and dry powder inhalation delivery devices.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension or crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include (poly(orthoesters) and poly(anhydrides). Depot injectable formulations are also prepared by entrapping the drug in liposomes or microemulsions which are compatible with body tissues.

In some embodiments, the synthetic, biodegradable particles of the present invention provide ease of manufacturing, broad availability of therapeutic agents, and increased treatment sites. In particular embodiments, surface-functionalized biodegradable poly(lactide-co-glycolide) particles with a high density of surface carboxylate groups, synthesized using the surfactant poly(ethylene-alt-maleic anhydride) provide a carrier that offers numerous advantages over other carrier particles and/or surfaces. Experiments conducted during development of embodiments of the present invention demonstrated the conjugation of peptides (e.g., $PLP_{139-151}$ peptide) to these particles. Such peptide-coupled particles have shown that they are effective for the prevention of disease development and the induction of immunological tolerance (e.g., in the SJL/J $PLP_{139-151}$/CFA-induced R-EAE murine model of multiple sclerosis). Peptide coupled carriers of the present invention provide numerous advantages over other tolerance induction structures. In some embodiments, the particles are biodegradable, and therefore will not persist for long times in the body. The time for complete degradation can be controlled. In some embodiments, particles are functionalized to facilitate internalization without cell activation (e.g., phosphatidylserine loaded into PLG microspheres). In some embodiments, particles incorporate targeting ligands for a specific cell population. In some embodiments, anti-inflammatory cytokines such as IL-10 and TGF-β, are included on or within particles to limit activation of the cell type that is internalizing the particles and to facilitate the induction of tolerance via energy and/or deletion and the activation of regulatory T cells. The composition of the particles has been found to affect the length of time the particles persist in the body and tolerance requires rapid particle uptake and clearance/degradation. Since ratios of over 50:50 lactide:glycolide slow the degradation rate, the particles of the invention have a lactide:glycolide ratio of about 50:50 or below. In one embodiment the particles of the invention have about a 50:50 D,L-lactide:glycolide ratio.

Solid dosage forms for oral administration include capsules, tablets, pills, powders, and granules. In such solid dosage forms, the modified particles are mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The modified particles can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose and starch. Such dosage forms may also comprise, as in normal practice, additional substances other than inert diluents, e.g., tableting lubricants and other tableting aids such as magnesium stearate and microcrystalline cellulose. In the case of capsules, tablets and pills, the dosage forms may also comprise buffering agents. They may optionally contain opacifying agents and can also be of a composition that they release the modified particles only, or preferentially, in a certain part of the intestinal tract, optionally, in a delayed manner. Examples of embedding compositions which can be used include polymeric substances and waxes.

The present invention encompasses pharmaceutically acceptable topical formulations of the inventive modified particles. The term "pharmaceutically acceptable topical formulation", as used herein, means any formulation which is pharmaceutically acceptable for intradermal administration of modified microparticles of the invention by application of the formulation to the epidermis. In certain embodiments of the invention, the topical formulation comprises a carrier system. Pharmaceutically effective carriers include, but are not limited to, solvents (e.g., alcohols, poly alcohols, water), creams, lotions, ointments, oils, plasters, liposomes, powders, emulsions, microemulsions, and buffered solutions (e.g., hypotonic or buffered saline) or any other carrier known in the art for topically administering pharmaceuticals. A more complete listing of art-known carriers is provided by reference texts that are standard in the art, for example, Remington's Pharmaceutical Sciences, 16th Edition, 1980 and 17th Edition, 1985, both published by Mack Publishing Company, Easton, Pa., the disclosures of which are incorporated herein by reference in their entireties. In certain other embodiments, the topical formulations of the invention may comprise excipients. Any pharmaceutically acceptable excipient known in the art may be used to prepare the inventive pharmaceutically acceptable topical formulations. Examples of excipients that can be included in the topical formulations of the invention include, but are not limited to, preservatives, antioxidants, moisturizers, emollients, buffering agents, solubilizing agents, other penetration agents, skin protectants, surfactants, and propellants, and/or additional therapeutic agents used in combination to the modified particles. Suitable preservatives include, but are not limited to, alcohols, quaternary amines, organic acids, parabens, and phenols. Suitable antioxidants include, but are not limited to, ascorbic acid and its esters, sodium bisulfite, butylated hydroxytoluene, butylated hydroxyanisole, tocopherols, and chelating agents like EDTA and citric acid. Suitable moisturizers include, but are not limited to, glycerine, sorbitol, polyethylene glycols, urea, and propylene glycol. Suitable buffering agents for use with the invention include, but are not limited to, citric, hydrochloric, and lactic acid buffers. Suitable solubilizing agents include, but are not limited to, quaternary ammonium chlorides, cyclodextrins, benzyl benzoate, lecithin, and polysorbates. Suitable skin protectants that can be used in the topical formulations of the invention include, but are not limited to, vitamin E oil, allatoin, dimethicone, glycerin, petrolatum, and zinc oxide.

In certain embodiments, the pharmaceutically acceptable topical formulations of the invention comprise at least the modified particles of the invention and a penetration enhancing agent. The choice of topical formulation will depend or several factors, including the condition to be treated, the physicochemical characteristics of the inventive compound and other excipients present, their stability in the formulation, available manufacturing equipment, and costs constraints. As used herein the term "penetration enhancing agent" means an agent capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, Percutaneous Penetration Enhancers, Maibach H. I. and Smith H. E. (eds.), CRC Press, Inc., Boca Raton, Fla. (1995), which surveys the use and testing of various skin penetration enhancers, and Buyuktimkin et al., Chemical Means of Transdermal Drug Permeation Enhancement in Transdermal and Topical Drug Delivery Systems, Gosh T. K., Pfister W. R., Yum S. I. (Eds.), Interpharm Press Inc., Buffalo Grove, Ill. (1997). In certain exemplary embodiments, penetration agents for use with the invention include, but are not limited to, triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate) and N-methylpyrrolidone.

In certain embodiments, the compositions may be in the form of ointments, pastes, creams, lotions, gels, powders, solutions, sprays, inhalants or patches. In certain exemplary embodiments, formulations of the compositions according to the invention are creams, which may further contain saturated or unsaturated fatty acids such as stearic acid, palmitic acid, oleic acid, palmito-oleic acid, cetyl or oleyl alcohols, stearic acid being particularly preferred. Creams of the invention may also contain a non-ionic surfactant, for example, polyoxy-40-stearate. In certain embodiments, the active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are made by dissolving or dispensing the compound in the proper medium. As discussed above, penetration enhancing agents can also be used to increase the flux of the compound across the skin. The rate can be controlled by either providing a rate controlling membrane or by dispersing the compound in a polymer matrix or gel.

The modified particles can be administered by aerosol. This is accomplished by preparing an aqueous aerosol, liposomal preparation or solid particles containing the modified particles. A nonaqueous (e.g., fluorocarbon propellant) suspension could be used.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics®, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

It will also be appreciated that the modified particles and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anti-inflammatory agent), or they may achieve different effects (e.g., control of any adverse effects).

In certain embodiments, the pharmaceutical compositions containing the modified particles of the present invention further comprise one or more additional therapeutically active ingredients (e.g., anti-inflammatory and/or palliative). For purposes of the invention, the term "Palliative" refers to treatment that is focused on the relief of symptoms of a disease and/or side effects of a therapeutic regimen, but is not curative. For example, palliative treatment encompasses painkillers, antinausea medications and anti-sickness drugs.

The invention provides methods of regulating an immune response in an individual, preferably a mammal, more preferably a human, comprising administering to the individual the modified particles described herein. Methods of immunoregulation provided by the invention include those that suppress and/or inhibit an innate immune response or an adaptive immune response, including, but not limited to, an immune response stimulated by immunostimulatory polypeptides or viral or bacterial components.

The modified particles are administered in an amount sufficient to regulate an immune response. As described herein, regulation of an immune response may be humoral and/or cellular, and is measured using standard techniques in the art and as described herein.

In some embodiments, compositions described herein are administered along with (e.g., concurrent with, prior to, or following) an implant (e.g., device) and/or transplant (e.g., tissue, cells, organ) to mediate, negate, regulate and/or reduce the immune response associated therewith.

In certain embodiments, the individual suffers from a disorder associated with unwanted immune activation, such as allergic disease or condition, allergy and asthma. An individual having an allergic disease or asthma is an individual with a recognizable symptom of an existing allergic disease or asthma. Tolerance can be induced in such an individual, for example, by particles complexed with the specific foods (e.g. peanut proteins, etc.), injected substances (e.g. bee venom proteins, etc.), or inhaled substances (e.g. ragweed pollen proteins, pet dander proteins, etc.) which elicit the allergic reaction.

In certain embodiments, the individual suffers from a disorder associated with unwanted immune activation, such as autoimmune disease and inflammatory disease. An individual having an autoimmune disease or inflammatory disease is an individual with a recognizable symptom of an existing autoimmune disease or inflammatory disease. Tolerance can be induced in such an individual, for example, by particles complexed with the relevant autoantigens driving the particular autoimmune disease.

In certain embodiments, the individual suffers from a disorder associated with enzyme replacement therapy. Tolerance can be induced in such an individual, for example, by particles complexed with the enzymes which patients with genetic deficiencies fail to produce, to prevent them from making neutralizing antibody responses to recombinantly-produced enzymes administered to treat their particular deficiency, e.g. tolerance to human Factor VIII in patients with hemophilia due to a genetic deficiency in the ability to make Factor VIII. Another example may include enzyme replacement in for conditions such as mucopolysaccharide storage disorder, gangliosidosis, alkaline hypophosphatasia, cholesterol ester storage disease, hyperuricemia, growth hormone deficiency, renal anemia or with lysomal storage disorders including Fabry's disease, Gaucher's disease, Hurler's disease, Hunter's syndrome, Maroteaux-Lamy disease, Niemann-Pick disease, Tay-Sachs disease, and Pompe disease.

In certain embodiments, the individual suffers from a robust, or otherwise adverse, immune response towards an agent administered for the treatment of a disease that actually or potentially compromises patient health or treatment. Additionally, novel compounds provided by this invention may be provided to individuals who do not show an immune response to an agent but may potentially do so in the future. In certain embodiments, the individual is receiving enzyme replacement therapy. In certain embodiments, therapeutic agents include, but are not limited to, peptides or protein-based agents, DNA vaccines, siRNA, splice-site switching oligomers, and RNA-based nanoparticles. In some embodiments, the therapeutic agents include, but are not limited to, Advate, antihemophilic factor, Kogenate, Eloctate, recombinant factor VIII Fc fusion protein, Refacto, Novo VIIa, recombinant factor VII, eptacog alfa, Helixate, Monanine, Coagulation Factor IX, Wilate, Ceredase, Alglucerase, Cerezyme, Imiglucerase, Elelso, taliglucerase alfa, Fabrazyme, Agalsidase beta, Aldurazyme, -I-iduronidase, Myozyme, Acid-glucosidase, Elaprase, iduronate-2-sulfatase, Naglazyme arylsufatase B, and N-acetylgalactosamin e-4-sulfatase. In some embodiments, the individual is administered therapeutic agents administered to treat diseases including, but not limited to, Hemophilia, Hemophilia A, Hemophilia B, von Willebrand disease, Gaucher's Disease, Fabry's Disease, Hurler's Disease, Pompe's Disease, Hunter's Disease, mucopolysaccharide storage disorder, gangliosidosis, alkaline hypophosphatasia, cholesterol ester storage disease, hyperuricemia, growth hormone deficiency, renal anemia and Maroteaux-Lary Disease.

In certain embodiments, the individual suffers from an orphan autoimmune condition. Such conditions include, but are not limited to, idiopathic thrombocytopenic purpura, membranous nephropathy, bullous pemphigoid, pemphigus vulgaris, and Myasthenia Gravis.

In certain embodiments, the individual suffers from a disorder associated with disease therapy. In the case of recombinant antibodies, tolerance is induced for example, to a humanized antibody being employed in a therapeutic context to prevent a patient from making neutralizing antibodies against the antibody therapeutic, e.g. tolerance to a humanized immune subset depleting antibody or anti-cytokine antibody being used as a treatment for autoimmune disease.

Autoimmune diseases can be divided in two broad categories: organ-specific and systemic. Autoimmune diseases include, without limitation, rheumatoid arthritis (RA), systemic lupus erythematosus (SLE), type I diabetes mellitus, type II diabetes mellitus, multiple sclerosis (MS), immune-mediated infertility such as premature ovarian failure, scleroderma, Sjogren's disease, vitiligo, alopecia (baldness), polyglandular failure, Grave's disease, hypothyroidism, polymyositis, pemphigus vulgaris, pemphigus foliaceus, inflammatory bowel disease including Crohn's disease and ulcerative colitis, autoimmune hepatitis including that associated with hepatitis B virus (HBV) and hepatitis C virus (HCV), hypopituitarism, graft-versus-host disease (GvHD), myocarditis, Addison's disease, autoimmune skin diseases, uveitis, pernicious anemia, Celiac disease, hypoparathyroidism neuomyelitis optica, membraneous nephropathy, bullous pemphigoid, pemphigus vulgaris, myasthenia gravis.

Autoimmune diseases may also include, without limitation, Hashimoto's thyroiditis, Type I and Type II autoimmune polyglandular syndromes, paraneoplastic pemphigus, bullus pemphigoid, dermatitis herpetiformis, linear IgA disease, epidermolysis bullosa acquisita, erythema nodosa, pemphigoid gestationis, cicatricial pemphigoid, mixed essential cryoglobulinemia, chronic bullous disease of childhood, hemolytic anemia, thrombocytopenic purpura, Goodpasture's syndrome, autoimmune neutropenia, myasthenia gravis, Eaton-Lambert myasthenic syndrome, stiff-man syndrome, acute disseminated encephalomyelitis, Guillain-Barre syndrome, chronic inflammatory demyelinating polyradiculoneuropathy, multifocal motor neuropathy with conduction block, chronic neuropathy with monoclonal gammopathy, opsonoclonus-myoclonus syndrome, cerebellar degeneration, encephalomyelitis, retinopathy, primary biliary sclerosis, sclerosing cholangitis, gluten-sensitive enteropathy, ankylosing spondylitis, reactive arthritides, polymyositis/dermatomyositis, mixed connective tissue disease, Bechet's syndrome, psoriasis, polyarteritis nodosa, allergic anguitis and granulomatosis (Churg-Strauss disease), polyangiitis overlap syndrome, hypersensitivity vasculitis, Wegener's granulomatosis, temporal arteritis, Takayasu's arteritis, Kawasaki's disease, isolated vasculitis of the central nervous system, thromboangiutis obliterans, sarcoidosis, glomerulonephritis, and cryopathies. These conditions are well known in the medical arts and are described, for example, in Harrison's Principles of Internal Medicine, 14th ed., Fauci A S et al., eds., New York: McGraw-Hill, 1998.

Animal models for the study of autoimmune disease are known in the art. For example, animal models which appear most similar to human autoimmune disease include animal strains which spontaneously develop a high incidence of the particular disease. Examples of such models include, but are not limited to, the nonobese diabetic (NOD) mouse, which develops a disease similar to type 1 diabetes, and lupus-like disease prone animals, such as New Zealand hybrid, MRL-$Fas^{lpr}$ and BXSB mice. Animal models in which an autoimmune disease has been induced include, but are not limited to, experimental autoimmune encephalomyelitis (EAE), which is a model for multiple sclerosis, collagen-induced arthritis (CIA), which is a model for rheumatoid arthritis, Desmoglein 3 transgenic T cell mouse, which can be used as an experimental model of Pemphigus Vulgaris and experimental autoimmune uveitis (EAU), which is a model for uveitis. Animal models for autoimmune disease have also been created by genetic manipulation and include, for example, IL-2/IL-10 knockout mice for inflammatory bowel disease, Fas or Fas ligand knockout for SLE, and IL-I receptor antagonist knockout for rheumatoid arthritis.

In certain embodiments, the individual suffers from a bacterial or viral infection. An individual having a bacterial or viral infection is an individual with a recognizable symptom of an existing bacterial or viral infection.

A non-limiting list of viral infections treatable with the modified particles of the current invention includes herpes virus infections, hepatitis virus infections, west nile virus infections, flavivrus infections, influenza virus infections, rhinovirus infections, papillomavirus infections, paromyxovirus infections, parainfluenza virus infections, and retrovirus infections. Preferred viruses are those viruses that infect the central nervous system of the subject. Most preferred viruses are those that cause hemorrgic fever, encephalitis or meningitis.

A non-limiting list of bacterial infections treatable with the modified particles of the current invention include staphlococcus infections, streptococcus infections, mycobacterial infections, bacillus infections, *Salmonella* infections, *Vibrio* infections, spirochete infections, and *Neisseria* infections. Preferred are bacteria that infect the central nervous system of the subject. Most preferred are bacteria that cause encephalitis or meningitis.

In some embodiments, the invention relates to uses of compositions of this invention prior to the onset of disease. In other embodiments, the invention relates to uses of the compositions of this invention to inhibit ongoing disease. In some embodiments, the invention relates to ameliorating disease in a subject. By ameliorating disease in a subject is meant to include treating, preventing or suppressing the disease in the subject.

In some embodiments, the invention relates to preventing the relapse of disease. For example, an unwanted immune response can occur at one region of a peptide (such as an antigenic determinant). Relapse of a disease associated with an unwanted immune response can occur by having an immune response attack at a different region of the peptide. Since the immune modifying particles of the current invention are free from attached peptides or antigenic moieties, the particles will be effective against multiple epitopes. T-cell responses in some immune response disorders, including MS and other ThI/17-mediated autoimmune diseases, can be dynamic and evolve during the course of relapsing-remitting and/or chronic-progressive disease. The dynamic nature of the T-cell repertoire has implications for treatment of certain diseases, since the target may change as the disease progresses. Previously, pre-existing knowledge of the pattern of responses was necessary to predict the progression of disease. The present invention provides compositions that can prevent the effect of dynamic changing disease, a function of "epitope spreading." A known model for relapse is an immune reaction to proteolipid protein (PLP) as a model for multiple sclerosis (MS). Initial immune response can occur by a response to $PLP_{139-15}$. Subsequent disease onset can occur by a relapse immune response to PLP[pi]s-iβi.

Other embodiments of this invention relate to transplantation. This refers to the transfer of a tissue sample or graft from a donor individual to a recipient individual, and is frequently performed on human recipients who need the tissue in order to restore a physiological function provided by the tissue. Tissues that are transplanted include (but are not limited to) whole organs such as kidney, liver, heart, lung; organ components such as skin grafts and the cornea of the eye; and cell suspensions such as bone marrow cells and cultures of cells selected and expanded from bone marrow or circulating blood, and whole blood transfusions.

A serious potential complication of any transplantation ensues from antigenic differences between the host recipient and the engrafted tissue. Depending on the nature and degree of the difference, there may be a risk of an immunological assault of the graft by the host, or of the host by the graft, or both, may occur. The extent of the risk is determined by following the response pattern in a population of similarly treated subjects with a similar phenotype, and correlating the various possible contributing factors according to well accepted clinical procedures. The immunological assault may be the result of a preexisting immunological response (such as preformed antibody), or one that is initiated about the time of transplantation (such as the generation of Th cells). Antibody, Th cells, or Tc cells may be involved in any combination with each other and with various effector molecules and cells. However, the antigens which are involved in the immune response are generally not known, therefore posing difficulties in designing antigen-specific therapies or inducing antigen-specific tolerance.

Certain embodiments of the invention relate to decreasing the risk of host versus graft disease, leading to rejection of the tissue graft by the recipient. The treatment may be performed to prevent or reduce the effect of a hyperacute, acute, or chronic rejection response. Treatment is preferentially initiated sufficiently far in advance of the transplant so that tolerance will be in place when the graft is installed; but where this is not possible, treatment can be initiated simultaneously with or following the transplant. Regardless of the time of initiation, treatment will generally continue at regular intervals for at least the first month following transplant. Follow-up doses may not be required if a sufficient accommodation of the graft occurs, but can be resumed if there is any evidence of rejection or inflammation of the graft. Of course, the tolerization procedures of this invention may be combined with other forms of immunosuppression to achieve an even lower level of risk.

Certain embodiments of the invention relate to decreasing or otherwise ameliorating the inflammatory response induced as a response to surgery. In one embodiment of the invention, the immune-modifying particles are administered before surgery. In a further embodiment of the invention, the immune-modifying particles are administered concurrently with or during surgery. In yet a further embodiment of the invention, the immune-modifying particles are administered after surgery.

The particles of the invention may also be used to treat abscesses or empyemas to decrease the inflammatory response produced in the subject after exposure to infectious agents such as bacteria or parasites. In one embodiment of the invention, the immune-modifying particles are administered in conjunction with anti-bacterial and/or anti-parasitic treatments known in the art.

The particles of the invention may also be used to decrease or otherwise ameliorate the inflammatory response induced as a response to physical trauma or injury including, but not limited to, a sports injury, a wound, a spinal cord injury, a brain injury, and/or a soft tissue injury. In one embodiment of the invention, the immune-modifying particles are administered after the subject experiences trauma or injury.

The particles of the invention may also be used to decrease the inflammatory response associated with the development and/or growth of cancer cells. Cancers that can be treated include, but are not limited to, central nervous system cancer, basal cell carcinoma, cancerous brain tumors, Burkitt's lymphoma, lymphoma, cervical cancer, ovarian cancer, testicular cancer, liver cancer, non-small cell and small cell lung cancers, melanoma, bladder cancer, breast cancer, colon and rectal cancers, endometrial cancer, kidney (renal cell) cancer, leukemia, Non-Hodgkin lymphoma, pancreatic cancer, prostate cancer, melanoma, and thyroid cancer. In one embodiment, the subcutaneous injection of the particles of the invention prevents the accumulation of inhibitory neutrophils, thereby decreasing inflammation in the cancer patient.

The particles of the invention are also useful for the regeneration of damaged tissue. In one embodiment, administration of the particles to a patient increases the regeneration of damaged epithelial cells in the digestive tract. In a further embodiment, the patient suffers from colitis, Crohn's disease, or inflammatory bowel disease. In another embodiment, administration of the particles of the invention to a patient increases remyelination of neurons. In a further embodiment, the patient suffers from multiple sclerosis.

In some embodiments, compositions of the present invention (e.g., PLG carrier coupled to antigenic molecule) find use with one or more scaffolds, matrices, and/or delivery systems (See, e.g., U.S. Pat. App. 2009/0238879; U.S. Pat. Nos. 7,846,466; 7,427,602; 7,029,697; 6,890,556; 6,797,738; 6,281,256; herein incorporated by reference in their entireties). In some embodiments, particles (e.g., antigen-coupled PLG particles) are associated with, adsorbed on, embedded within, conjugated to, etc. a scaffold, matrix, and/or delivery system (e.g., for delivery of chemical/biological material, cells, tissue, and/or an organ to a subject). In some embodiments, a scaffold, matrix, and/or delivery system (e.g., for delivery of chemical/biological material, cells, tissue, and/or an organ to a subject) comprises and/or is made from materials described herein (e.g., PLG conjugated to one or more antigenic peptides).

In some embodiments, microporous scaffolds (e.g., for transplanting biological material (e.g., cells, tissue, etc.) into a subject) are provided. In some embodiments, microporous scaffolds are provided having thereon agents (e.g., extracellular matrix proteins, exendin-4) and biological material (e.g., pancreatic islet cells). In some embodiments, the scaffolds are used in the treatment of diseases (e.g., type 1 diabetes), and related methods (e.g., diagnostic methods, research methods, drug screening). In some embodiments, scaffolds are provided with the antigen-conjugated carriers described herein on and/or within the scaffold. In some embodiments, scaffolds are produced from antigen conjugated materials (e.g., antigen conjugated PLG).

In some embodiments, a scaffold and/or delivery system comprises one or more layers and/or has one or more chemical and/or biological entities/agents (e.g., proteins, peptide-conjugated particles, small molecules, cells, tissue, etc.), see, e.g., U.S. Pat. App. 2009/0238879; herein incorporated by reference in its entirety. In some embodiments, antigen-coupled particles are co-administered with a scaffold delivery system to elicit induction of immunological tolerance to the scaffold and the associated materials. In some embodiments, microporous scaffold is administered to a subject with particles described herein on or within the scaffold. In some embodiments, antigen-coupled particles coupled to a scaffold delivery system. In some embodiments, a scaffold delivery system comprises antigen-coupled particles.

Various modification, recombination, and variation of the described features and embodiments will be apparent to those skilled in the art without departing from the scope and spirit of the invention. Although specific embodiments have been described, it should be understood that the invention as claimed should not be unduly limited to such specific embodiments. Indeed, various modifications of the described modes and embodiments that are obvious to those skilled in the relevant fields are intended to be within the scope of the following claims. For example, U.S. Pat. Applications 2012/0076831, 2002/0045672, 2005/0090008, 2006/0002978, and 2009/0238879 (each of which is herein incorporated by reference in their entirety) and U.S. Pat. Nos. 7,846,466; 7,427,602; 7,029,697; 6,890,556; 6,797,738; and 6,281,256 (each of which is herein incorporated by reference in their entirety) provide details, modifications, and variations that find use in various embodiments described herein.

All publications and patents mentioned in the present application and/or listed below are herein incorporated by reference in their entireties.

EXAMPLES

The following examples are provided to further illustrate the advantages and features of the invention, but are not intended to limit the scope of this disclosure.

Materials and Methods

Generation of Chimeric Mice

Six- to eight-week old B6.SJL-Ptprc$^a$Pep3$^b$/BoyJ (CD45.1) mice were irradiated with one dose of 950 rads. Twelve hours later, mice were reconstituted with $10^7$ bone marrow cells from C57BL/6-7.2fms-EGFP donors. Mice were given sulfamethoxazole (Sigma Aldrich) and trimethoprim (Sigma Aldrich) in the drinking water for 10 days following irradiation. Mice were infected with WNV six weeks after irradiation, as described above. Chimerism was checked using flow cytometry and was invariably found to be 96-99% of donor origin as previously demonstrated (Getts et al., J Neurochem. 103: 1019, 2007).

Immunohistology

Mice were anesthetized and perfused with 50 mL sterile PBS. With the exception of the heart, which were processed into paraffin blocks (Getts et al., J. Neurochem 103:10919-1030, 2007), all organs were isolated and snap frozen in Optimum Cutting Temperature Compound (OCT; Tissue-Tek, Tokyo, Japan). Eight-micron tissue sections were cut on a cryostat microtome, air-dried overnight and then stored at −80° C. until required. Frozen sections were thawed and histology (standard haematoxylin and eosin staining) or immunohistochemistry was performed (Getts et al., J. Exp Med 205:2319-2337, 2008). Antibodies against MARCO, SIGN-R1 and SIGLEC-1 (R&D Systems, MN, USA), CD68 (Abcam, Mass., USA) and Ki67 (Abcam), were used as indicated. Images were acquired on an Olympus BX-51 microscope using a DP-70 camera and DP manager 2.2.1 software (Olympus, Tokyo, Japan).

Microscope and Image Acquisition

Images were acquired on an Olympus BX-51 microscope (Olympus, Japan), using a DP-70 camera and DP manager 2.2.1 software (Olympus).

Isolation of Leukocytes from the Brain and Liver

As previously described (Getts et al, J Exp Med. 29: 2319, 2007) leukocytes were obtained from the brains of PBS-perfused mice by digesting brains for 60 minutes at 37° C. in PBS with deoxy-ribonuclease (0.005 g/ml; Sigma Aldrich) and collagenase IV (0.05 g/ml; Sigma Aldrich). Digestion was stopped with 10% FCS, and the homogenate was passed through a 70 µm nylon cell strainer (Becton Dickinson, N.J., USA). The pellet, obtained after 10 minutes centrifugation at 340×g, was resuspended in 30% Percoll (Amersham, Norway) and layered over 80% Percoll. Leukocytes were collected from the 30%/80% interface after centrifugation at 1140×g for 25 minutes at room temperature. The same protocol is also used to derive leukocytes from the liver, with the tissue weighed before processing.

Isolation of Leukocytes from the Spleen, Blood and Bone Marrow

For flow cytometric analysis, the right femur was dissected out and bone marrow cells flushed out using PBS loaded syringes. For bone marrow precursor isolation, femurs and tibias from at least 4 mice were utilized. The cellular suspension achieved after flushing was filtered through a 70 µm cell strainer and centrifuged for 5 mins at 340 g. Red blood cells in the resulting pellet were lysed in NH$_4$Cl-based red cell lysis buffer (BD Pharm Lyse™; BD Pharmingen), before centrifugation for 5 mins at 340×g. In the case of peripheral blood, blood was collected via cardiac puncture and immediately transferred into citrate buffer (mMol, Sigma Alrich). The resulting suspension was layered over 70% Percoll and centrifuged at 1140×g for 20 minutes at room temperature with the brake off. The interface was collected and the cells washed once in PBS, centrifuged at 340×g. For the isolation of splenic leukocytes, spleens were passed through a 7070 µm cell strainer and centrifuged for 5 mins at 340 g. Red blood cells in the resulting pellet were lysed in NH$_4$Cl-based red cell lysis buffer (BD Pharm Lyse™; BD Pharmingen), before centrifugation for 5 mins at 340×g.

Flow Cytometry

Cells collected (as described above) from the brain, liver, blood, and bone marrow were washed in PBS, and blocked with anti-CD16/CD32 antibody (Biolegend). Viable cells were counted using trypan blue exclusion, which routinely showed >95% cell viability.

Cell surface molecule expression was measured and cell sorts carried out on a FACS ARIA (Becton Dickinson), equipped with an Argon ion and HeNe laser. Viable populations were gated by forward and side scatter and identified fluorescent populations determined by forward-gating thereafter. Sorting was carried out using specific fluorescent and scatter parameters identifying the population of interest. Sorting stringencies was set to purity to achieve >98% purity for bone marrow populations.

Acquired FACS data files were analysed using the flow cytometry program, Flow Jo (FlowJo, Ashland, Oreg., USA). Quantification of cell populations of interest were calculated based on flow cytometry percentages at analysis and absolute cell counts from each organ.

Adoptive Transfer

Experiments were conducted during development of embodiments of the present invention to investigate a second model of active disease termed adoptive transfer. Rather than immunizing the animals with the peptide, the lymphocytes from the spleen of mice with active disease were transferred to a recipient, who would subsequently develop disease. Experiments were conducted during development of embodiments of the present invention to characterize the ability of the PLG nanoparticles to deactivate the adoptively transferred activated effector cells. Mice treated with particles or splenocytes coupled with a control peptide had an increase in clinical score beginning at day 4. Mice treated with PLG-PLP$_{139-151}$ particles at day 2 had a mean clinical score of 0 for all but two time points through day 40, and the mean clinical score for those other time points was 0.25.

Multiplex ELISA

Multiplexed plate ELISAs were performed according to the manufacturers instructions (Quansys Biosciences, Logan, Utah, USA). Briefly, brain, spleen, and liver tissue were homogenized in PBS, clarified by a 1000×g spin, and stored at −20° C. until the assay was performed. Serum samples were also used. Thawed samples and standards were diluted in the provided buffer, and 30 µl of each were plated in each well that contains 16 spots each containing a capture antibody for a particular soluble protein. Plates were then incubated for 1 hour on an orbital shaker at 120 r.p.m. Plates were washed 3 times, and 30 µl of detection antibody was added to each well and incubated for another hour. After washing 3 times, strepavidin-HRP was added and incubated for a further 15 minutes. Plates were then washed 6 times, and substrate mix was added. Plates were immediately read on a CCD imager (Kodak, Rochester N.Y., USA). Plate images were analysed using Quansys Q-view software (Quansys Biosciences).

Induction and Evaluation of Experimental Autoimmune Encephalitis (EAE)

Mice were injected sub-cutaneously with emulsion containing 0.1 mg MOG Peptide (MEVGWYRSPFSRVVH-LYRNGK (SEQ ID NO:1); Auspep, Parkville, Victoria, Australia; >95% HPLC purified) and Complete Freund's adjuvant containing 2 mg/mL *Mycobacterium tuberculosis*

(Sigma Aldrich). Two days later, mice were administered 500 µl Pertussis toxin (Sigma Aldrich) i.p. Mice were monitored for disease progression, and graded on the following scale: 1, limp tail and/or weakness of 1 hind limb; 2, weakness in more than one limb, gait disturbance; 3, paralysis in 1 limb; 4, paralysis in more than one limb, incontinence; 5, moribund.

Statistics

Graphs were made and computerized statistical analysis was performed in GraphPad Prism, and InStat, respectively (both programs from GraphPad software, San Diego, Calif., USA). Depending on the data, an unpaired, two-tailed Student t-test, or one way ANOVA with a Tukey-Kramer post test was performed, with P<0.05 considered to be significant.

For correlation analysis between parameters such as weight loss, infiltration, and virus titre, a non-linear regression (curve fit) was used, with a second order polynomial $(Y=A+B*X+C*X^2)$.

Example 1

Preparation of Negatively Charged Immune Modifying Particles (IMPs)

To a solution of Poly(ethylene-maleic anhydride) (PEMA) in $D_2O$ (4 mL, 1% w/v) was added dropwise a solution of poly(lactide-co-glycolic acid) (PLG) in dichloromethane (DCM) (2 mL, 20% w/v). The mixture was allowed to sonicate on ice at 16 watts for 30 sec using the VC 30 Ultrasonic Processor. The resulting homogenized crude was then poured into a solution of $D_2O$ (200 mL containing 0.5% w/v of PEMA). The homogenized slurry was allowed to stir overnight at speed setting of 3.5 using Bellco Glass, Inc., Bellstir Multi-stir 9 magnetic stirrer (10 W for 10 s, 16 W for 10 s, 16 W for 30 s).

Results

After three hours of stirring, particle size analyses were performed using dynamic light scattering in disposable polystyrene cuvettes
 a. 10 W, 10 s—Z-average=499.9 nm—PdI=0.23, Peak=634.5 nm
 b. 16 W, 10 s—Z-average=528.9 nm—PdI=0.227, Peak=657.5 nm
 c. 16 W, 30 s—Z-average=471.6 nm—PdI=0.228, Peak=580.5 nm
 d. 16 W, 60 s—Z-average=491.1 nm—PdI=0.275, Peak=600.8 nm After the reaction was complete, the resulting crude suspension was then purified.

Purification

Fresh $D_2O$ and 10× sodium bicarbonate buffer were chilled overnight to 4° C. Using a 40 µm cell strainer, 36 mL of particle suspension were filtered from each batch into an appropriately-labelled 50 mL centrifuge tube containing 4 mL chilled 10× sodium bicarbonate buffer. Each beaker produced approximately 6 such tubes. All tubes were centrifuged for about 15 minutes at 7000 g at 4° C. and the supernatant was aspirated. Preparation of the suspension was repeated using the above-mentioned procedure and much of the particle pellets were suspended as possible in 1 mL chilled $D_2O$.

The resuspended particles were transferred into a fresh tube with 4 mL of chilled 10× sodium bicarbonate buffer. (Step 1)

Resuspension of the particle was repeated until the entire particle pellets haves been successfully resuspended. (Step 2)

The 6 centrifugal tubes were then combined into one centrifuge tube (50 mL tube) and the tube was filled with the remaining volume to 40 mL of chilled $D_2O$ (Wash 1).

The tube was centrifuged for 20 minutes at 7000 g at 4° C. and the supernatant was aspirated.

Step 1 and 2 and Wash 1 of the resulting particle were repeated each time at least two more times. Finally, the resulting particle pellets were then subjected to a flash-freeze in liquid nitrogen and lyophilized to dryness in the manifold to obtain negatively IMPs.

FIG. 1 shows characterization of surface-functionalized poly(lactide-co-glycolide) particles by dynamic light scattering analysis. Surface-functionalized poly(lactide-co-glycolide) particles were analysed on a Malvern Zetasizer Nano ZS (Malvern Instruments, Westborough, Mass.) at a count rate of $2.5\times10^5$ counts per second in 18.2 MΩ water. The population of surface-functionalized poly(lactide-co-glycolide) particles had a Z-average diameter of 567 nm, a peak diameter of 670 nm and a polydispersity index of 0.209.

Table 4 shows the measurements for surface functionalized PLG-PEMA particles. The data in the table is representative, as each batch is slightly different. The numbers in the table were based on combining several batches of particles though. The measurements for the double emulsion particles are similar to those in Table 2.

TABLE 4

Measurements for the surface functionalized PLG-PEMA particles

| Particle | Z-average size by intensity (nm) | ζ-potential (mV) |
|---|---|---|
| PLG (Phosphorex) | 624.3 | −32.7 ± 4.71 |
| PLG-PEMA | 429.9 | −67.4 ± 10.9 |

Example 2

Administration of Antigen-Coupled PLGA Beads Prevents Relapsing Experimental Autoimmune Encephalitis PLG nanoparticles were investigated with the immunodominant proteolipid protein $PLP_{139-151}$ epitope (PLG-$PLP_{139-151}$) to induce tolerance for prevention of Relapsing Experimental Autoimmune Encephalitis (R-EAE). The R-EAE mice were generated as described above.

The peptides administered to the animals were coupled to particles with the mean diameter of 500 nm. Mice were treated with either $PLP_{139-151}$-PLGA (N=5), $OVA_{323-339}$-PLGA (N=5), or unconjugated PLGA (N=5) on day −7 relative to the time of immunization (day 0). Peak disease was typically observed around day 12 to 14, and mice are scored for clinical disease. Particles without peptide, or modified with the control peptide $OVA_{323-339}$ did not prevent disease induction. However, PLGA particles modified with $PLP_{139-151}$ produced a clinical score of 0 (no disease) at all except low clinical scores of under 1 exhibited between days 20 and 30 (FIG. 2). Previous studies with unmodified PLG or using polystyrene particles did not produce this effective disease reduction, with polystyrene bound particles commonly triggering anaphylaxis.

Furthermore, specific inactivation of myelin-specific $CD4^+$ T cells was demonstrated by lack of delayed-type hypersensitivity (DTH) responses to both immunizing $PLP_{139-151}$ epitope. Taken together, prophylactic treatment with PLG-$PLP_{139-151}$ on day-7 specifically prevented EAE development, and represents an improvement in the ability of particles to prevent disease. The scores produced with the particles are as good as, and perhaps better, than the scores produced with antigen-coupled splenocytes.

Figure 3A:
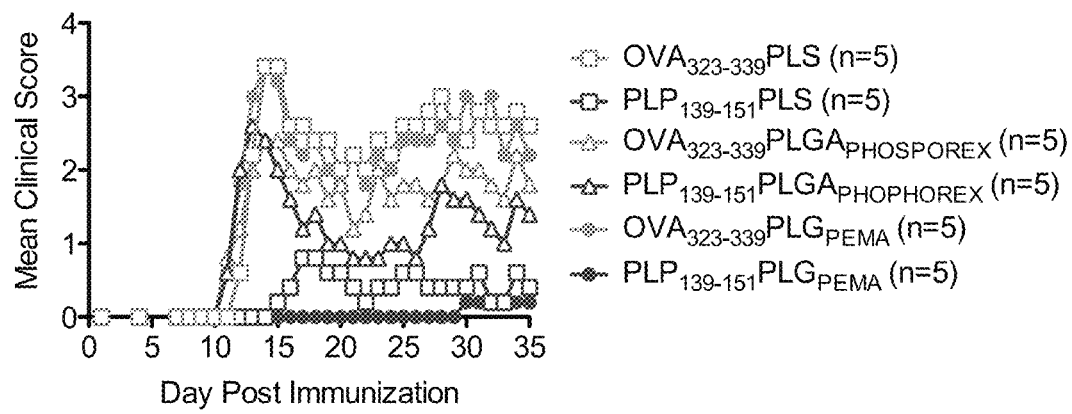
FIGS. 3A-3B show that the type of particle administered has an effect on the development of EAE in the mouse model.
Figure 3B:
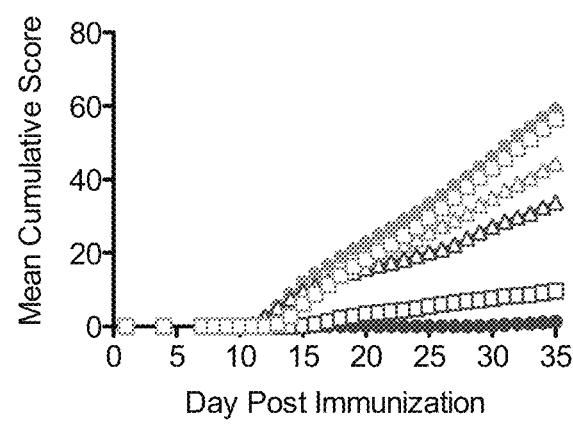

The type of particle administered also has an effect on the development of EAE in the mouse model. Mice were treated with either $OVA_{323-339}$-PLS (N=5), $OVA_{323-339}$-$PLGA_{PHOSPOREX}$ (N=5), $OVA_{323-339}$-$PLGA_{PEMA}$ (N=5), $PLP_{139-151}$-PLA (N=5), $PLP_{139-151}$-$PLGA_{PHOSPOREX}$ (N=5), or $PLP_{139-151}$-$PLG_{PEMA}$ (N=5) on day −7 relative to the time of immunization (day 0). Peak disease was typically observed around day 12 to 14, and mice are scored for clinical disease. Particles, of any composition that were modified with the control peptide $OVA_{323-339}$ did not prevent disease induction. However, the $PLP_{139-151}$ coupled PLG beads were more effective in down-regulating induction of R-EAE than $PLP_{139-151}$ coupled commercial (Phosphorex) pLG or polystyrene (FIGS. 3A and 3B).

Example 3

Intravenous Infusion of Antigen Coupled PLG Particles does not Induce Anaphylaxis-Induced Temperature Drop in OVA/Alum Pre-Sensitized Animals Due to the presence of active disease, anaphylaxis to the antigens is a concern, which could result in immediate mortality, and has been described with polystyrene bound particles. Anaphylaxis is associated with a significant drop in body temperature. To test whether intravenous administration of OVA-PLG induces an anaphylaxis-induced temperature drop in pre-sensitized animals, mice were immunized at day 0 with 10 μg OVA/Alum via intraperitoneal injection. On day 14, the mice were again immunized with 10 μg OVA/Alum via intraperitoneal injection, and then tolerized with OVA-PLG administered intravenously on day 21. On day 28, the mice were then tolerized with either OVA-PLG particles or OVA via intravenous administration.

Figure 4:
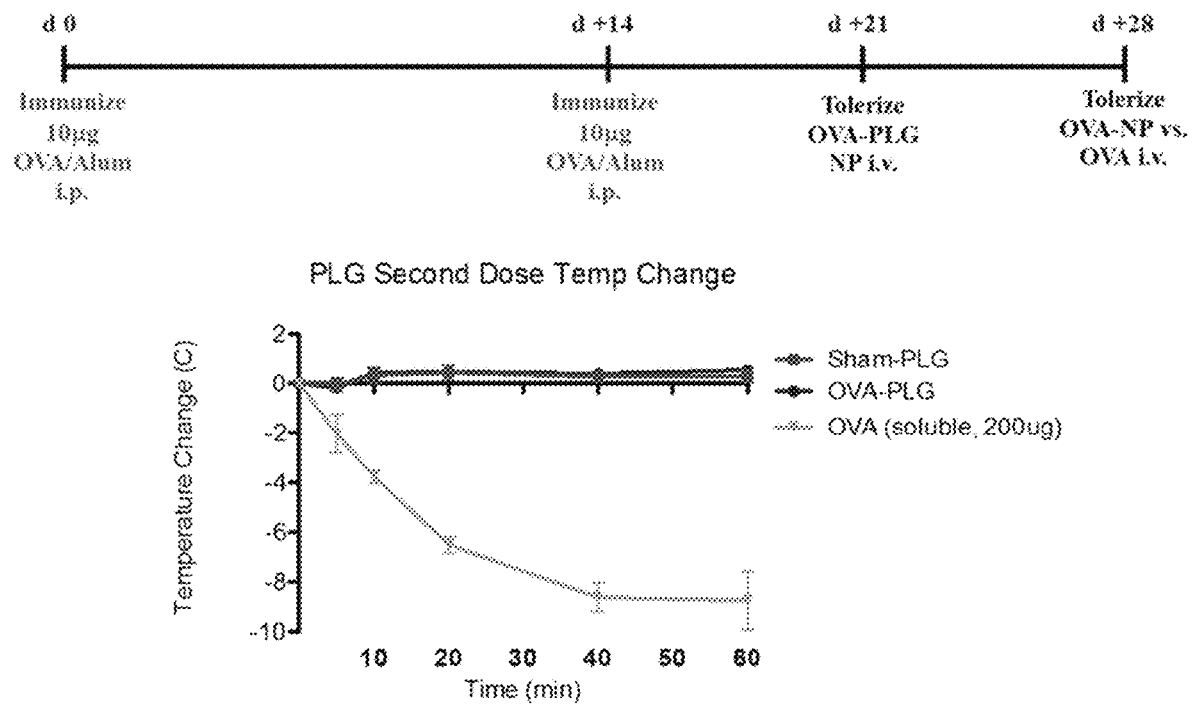
FIG. 4 shows that those mice treated with soluble OVA on day 28 exhibited a decrease in temperature compared with those animals treated with the OVA-PLG particle. No decrease in body temperature was observed within 1 hour of delivering the particles.

As shown in FIG. 4 those mice treated with soluble OVA on day 28 exhibited decrease in temperature compared with those animals treated with the OVA-PLG particle. No decrease in body temperature was observed within 1 hour of delivering the particles.

Figure 5A:
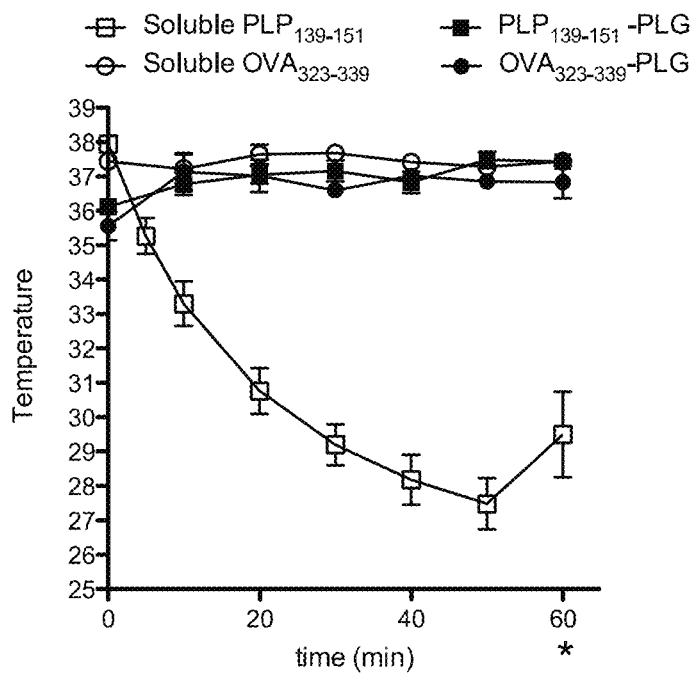
FIGS. 5A-5B show that administration of PLP-PLG during remission does not result in any anaphylaxis-associated mortality. EAE was induced in six to eight week old female SJL/J mice by subcutaneous injection of $PLP_{139-151}$ in CFA, and development of clinical disease was monitored and recorded (FIG. 5B). On day 21 relative to disease induction, mice were given iv injections of soluble $PLP_{139-151}$ (clear squares), soluble $OVA_{323-339}$ (clear circles), or the same peptides coupled to PLG nanoparticles (solids). Temperature of animals was monitored and recorded every 10 minutes for 1 hour following injection (FIG. 5A)
Figure 5B:
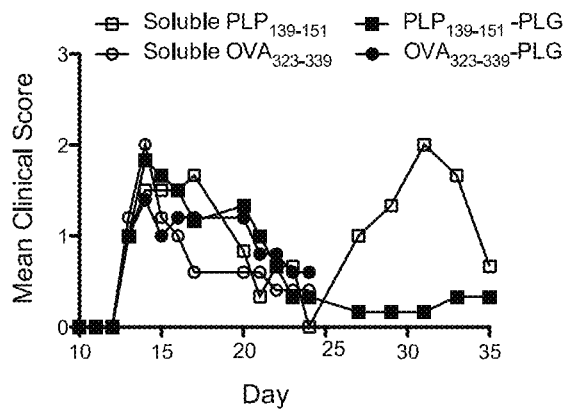

FIG. 5 shows that administration of PLP-PLG during remission does not result in any anaphylaxis-associated mortality. EAE was induced in six to eight week old female SJL/J mice by subcutaneous injection of $PLP_{139-151}$ in CFA, and development of clinical disease was monitored and recorded (FIG. 5B). On day 21 relative to disease induction, mice were given iv injections of soluble $PLP_{139-151}$ (clear squares), soluble $OVA_{323-339}$ (clear circles), or the same peptides coupled to PLG nanoparticles (solids). Temperature of animals was monitored and recorded every 10 minutes for 1 hour following injection (FIG. 5A).

Example 4

Figure 6A:
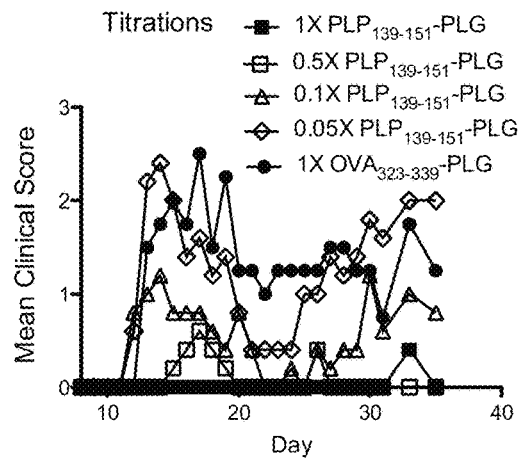
FIGS. 6A-6F show the optimal dosing of $PLP_{139-151}$-PLG administered intravenously seven days prior to disease induction. Development of clinical disease was measured in comparison to SJL/J mice treated with $OVA_{323-339}$-PLG (FIG. 6A). Six to eight week old female SJL/J mice were injected iv with either $PLP_{139-151}$ (square)- or $OVA_{323-339}$ (circle)-coupled PLG nanoparticles. EAE was induced by subcutaneous injection of $PLP_{139-151}$ in CFA 7 days (FIG. 6B), 25 days (FIG. 6C), or 50 days (FIG. 6D) later. Animals from panel B were followed for clinical disease for 100 days. On day 8 relative to disease induction, a delayed-type hypersensitivity (DTH) reaction was carried out in a subset of the mice shown in panel B (FIG. 6E). Selected representative animals from the $PLP_{139-151}$/CFA primed groups in panel B ($OVA_{323-339}$-PLG and $PLP_{139-151}$-PLG) were ear-challenged with the priming $PLP_{139-151}$ epitope and the $OVA_{323-339}$ control peptide. Ear swelling as a measure of DTH was determined 24 h later and responses prior to challenge were subtracted. Six to eight-week old female SJL/J mice were injected intravenously with $PLP_{178-191}$ (triangle)-, $OVA_{323-339}$ (circle), or $PLP_{139-151}$ (square)-coupled PLG nanoparticles, or with uncoupled particles alone (outlined circle) (FIG. 6F). EAE was induced 7 days afterward by subcutaneous injection of $PLP_{178-191}$ in CFA, and disease was monitored at the time points shown.
Figure 6B:
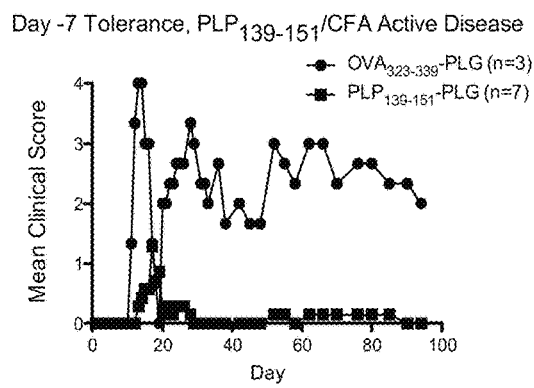
Figure 6C:
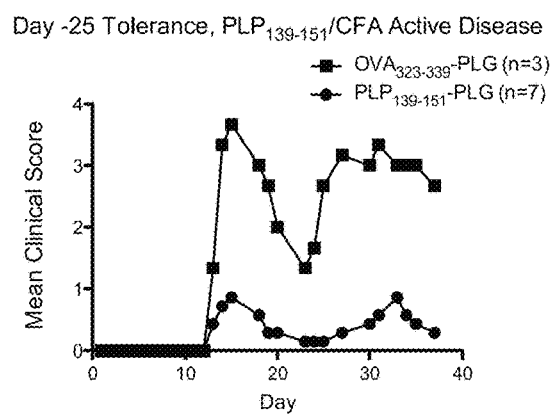
Figure 6D:
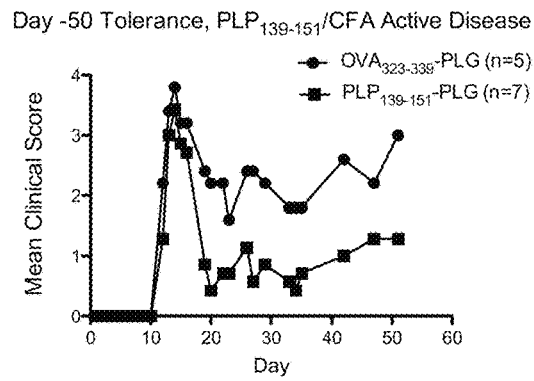
Figure 6E:
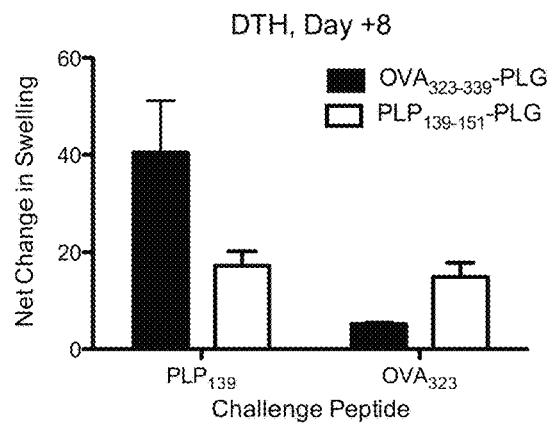
Figure 6F:
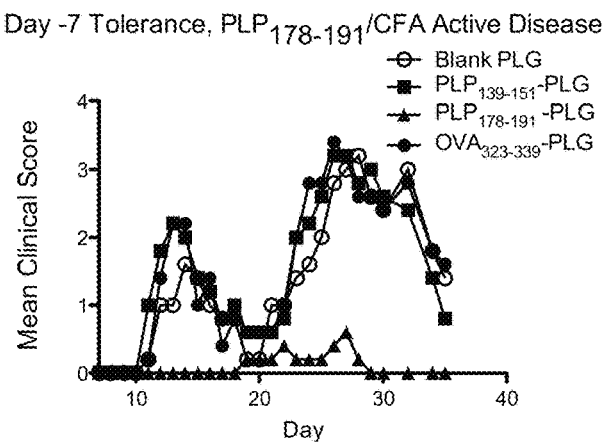
Figure 7A:
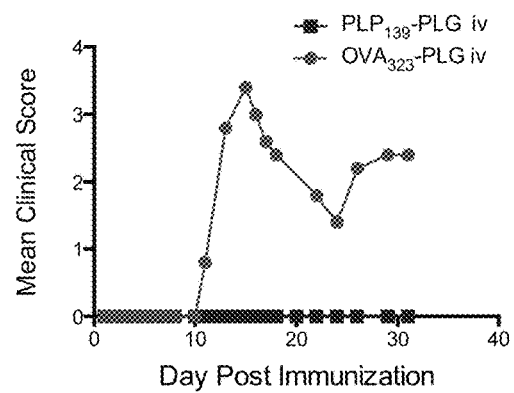
FIGS. 7A-7D show prophylactic tolerance is most efficient when the PLG-$PLP_{139-151}$ particles are administered either intravenously or intraperitoneally. Animals treated with $PLP_{139-151}$-PLG administered intravenously did not develop disease and had mean clinical scores of 0 at most time points.
Figure 7B:
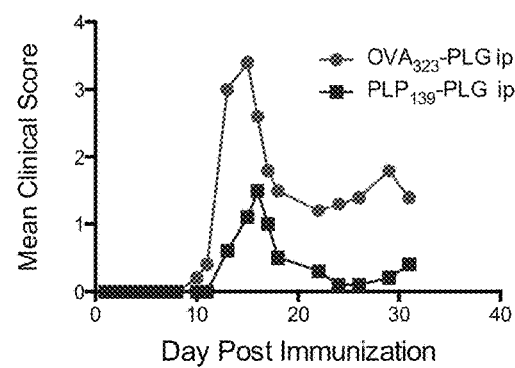
Figure 7C:
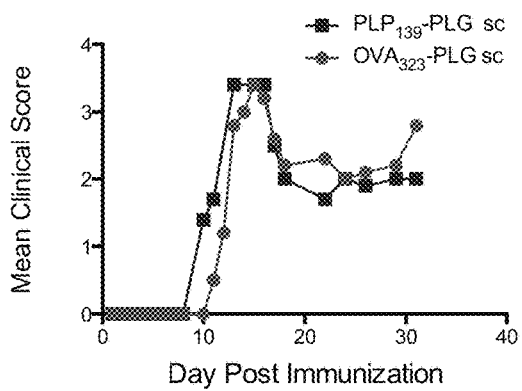
Figure 7D:
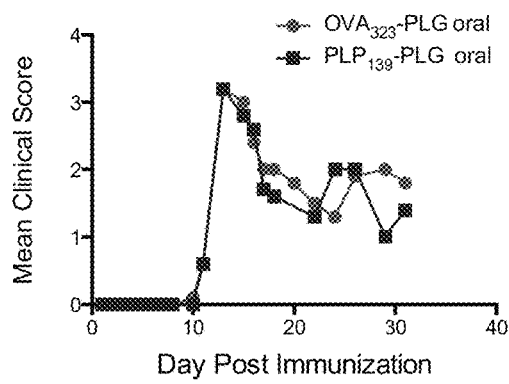
Figure 8A:
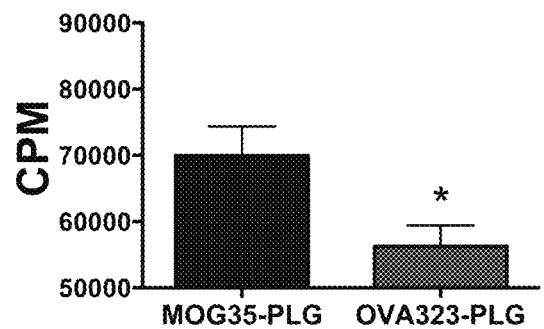
FIGS. 8A-8F show that the administration of $OVA_{323-339}$-PLG particles inhibited the Th1 and Th17 responses in the treated animals.
Figure 8B:
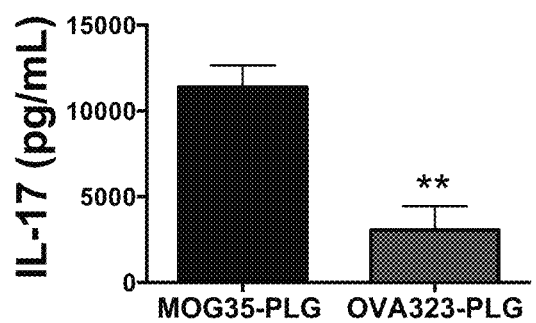
Figure 8C:
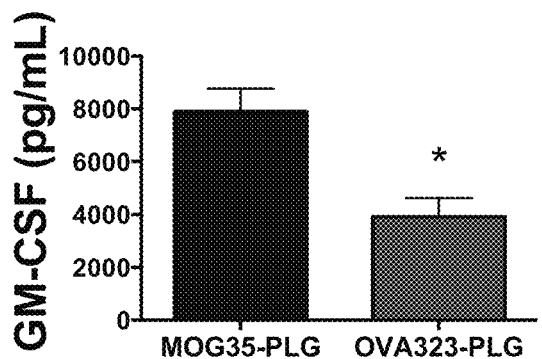
Figure 8D:
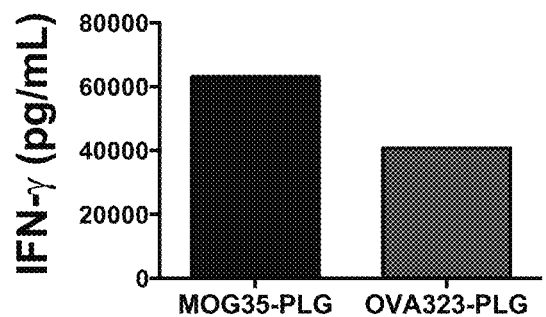
Figure 8E:
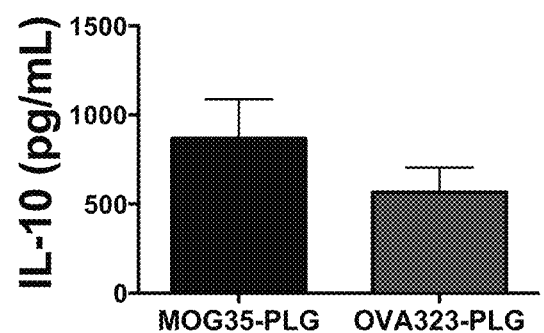
Figure 8F:
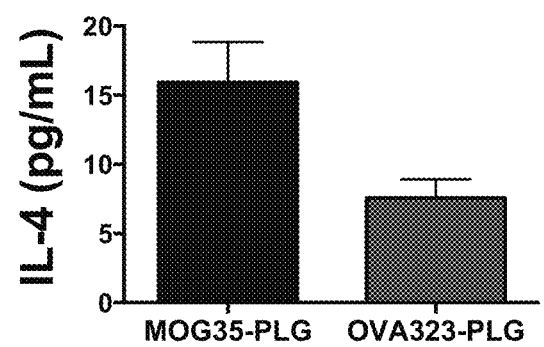

Prophylactic Treatment with PLP-PLG Particles Induces Long-Term, Antigen-Specific Tolerance Optimal dosing was determined by intravenous administration of increasing concentrations of $PLP_{139-151}$-PLG seven days prior to disease induction, and monitored for development of clinical disease in comparison to SJL/J mice treated with $OVA_{323-339}$-PLG (FIG. 6A). Six to eight week old female SJL/J mice were injected iv with either $PLP_{139-151}$ (square)- or $OVA_{323-339}$ (circle)-coupled PLG nanoparticles. EAE was induced by subcutaneous injection of $PLP_{139-151}$ in CFA 7 days (FIG. 6B), 25 days (FIG. 6C), or 50 days (FIG. 6D) later. Animals from panel B were followed for clinical disease for 100 days. FIG. 6E shows that on day 8 relative to disease induction, a delayed-type hypersensitivity (DTH) reaction was carried out in a subset of the mice shown in panel B. Selected representative animals from the $PLP_{139-151}$/CFA primed groups in panel B ($OVA_{323-339}$-PLG and $PLP_{139-151}$-PLG) were ear-challenged with the priming $PLP_{139-151}$ epitope and the $OVA_{323-339}$ control peptide. Ear swelling as a measure of DTH was determined 24h later and responses prior to challenge were subtracted. FIG. 6F shows that six to eight-week old female SJL/J mice were injected intravenously with $PLP_{178-191}$ (triangle)-, $OVA_{323-339}$ (circle), or $PLP_{139-151}$ (square)-coupled PLG nanoparticles, or with uncoupled particles alone (outlined circle). EAE was induced 7 days afterward by subcutaneous injection of $PLP_{178-191}$ in CFA, and disease was monitored at the time points shown.

Example 5

Treatment of Relapsing Experimental Autoimmune Encephalitis with Antigen-Coupled Particles Experiments were conducted during development of embodiments of the present invention to investigate the ability of the PLG-$PLP_{139-151}$ particles to treat disease rather than prevent disease, and to determine whether the route of administration affected the development of disease. Mice were immunized at day 0 with $PLP_{139-151}$ and an adjuvant. Mice normally have maximal clinical scores at day 12-14. In this model, the mice were treated at day 10 with the PLG-$PLP_{139-151}$ particles or with control PLG-$OVA_{323-339}$ particles either via intravenous (iv) administration, intraperitoneal (ip) administration, subcutaneous (sc) administration, or orally. As shown in FIG. 7, prophylactic tolerance is most efficient when the PLG-$PLP_{139-151}$ particles are administered either intravenously or intraperitoneally. Animals treated with $PLP_{139-151}$-PLG administered intravenously did not develop disease and had mean clinical scores of 0 at most time points. This is in contrast to animals treated with $PLP_{139-151}$ polystrene particles, whereby >70% of animals where observed to die from anaphylaxis.

Example 6

Antigen-Coupled Particle Tolerance Inhibits Induction of Antigen-Specific Th1 and Th17 Responses in Active Relapsing Experimental Autoimmune Encephalitis To determine whether administration of antigen-coupled particles inhibit induction of T-helper cells, either $MOG_{35-55}$-PLG or $OVA_{323-339}$-PLG particles were administered intravenously to BALB/c mice at Day −7. On Day 0, $OVA_{323-339}$-PLG particles and Complete Freund's Adjuvant (CFA) were administered subcutaneously to the mice. The animals were re-stimulated with either $MOG_{35-55}$-PLG or $OVA_{323-339}$-PLG particles on Day 10 and the draining lymph node cells were isolated. The CPM and levels of IL-17, GM-CSF, IFN-γ, IL-10, and IL-4 were measured at Day 10. As shown in FIG. 8, the administration of $OVA_{323-339}$-PLG particles inhibited the Th1 and Th17 responses in the treated animals.

Example 7

Tolerance is Induced by PLP-$_{139-151}$ Coupled PLGA Particles

Figure 9A:
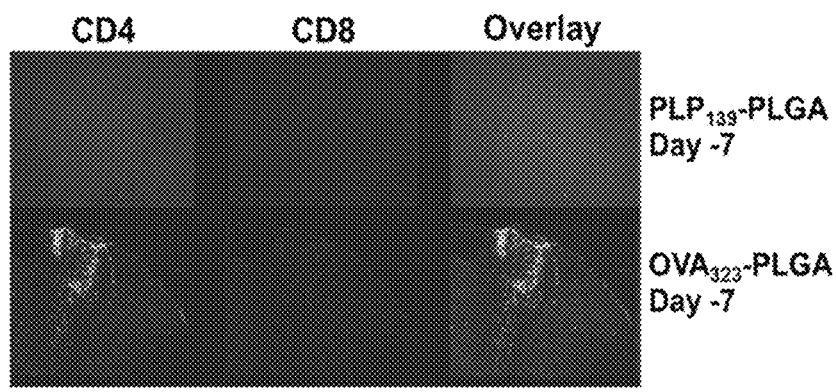
FIGS. 9A-9C show a reduction in immune cell infiltration within the spinal cord of animals treated with $PLP_{139-151}$-PLG that and was more similar to native tissue than to tissue from $OVA_{323-339}$-PLG treated animals. $OVA_{323-339}$-PLG treated animals had positive staining for CD45, CD4, and CD11b; whereas, $PLP_{139-151}$-PLG treated animals had minimal staining for these factors.
Figure 9B:
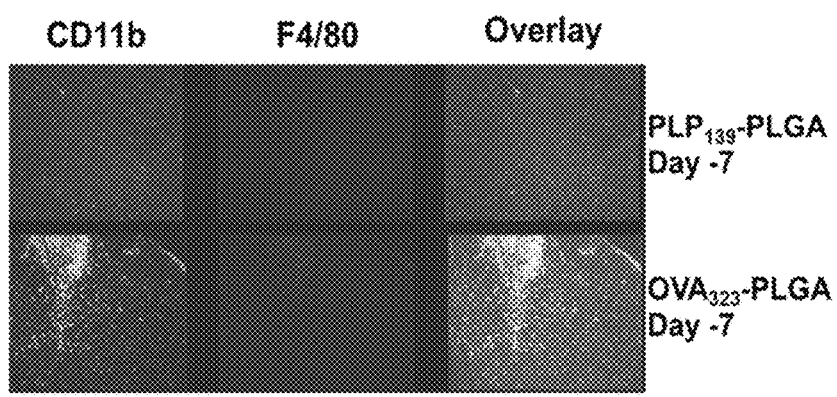
Figure 9C:
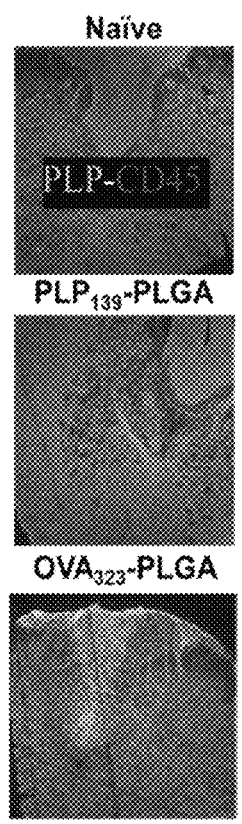

An additional therapeutic tolerance strategy was performed by delivering $PLP_{139-151}$-PLG or $OVA_{323-339}$ PLG to mice. Histological analysis showed that the administration of the PLP$_{139-151}$-PLG particles inhibits cervical spinal cord inflammation and demyelination. Mice were treated with PLP-PLG or OVA$_{323-339}$-PLG and the tissue was retrieved at day 40. The cervical spinal cord was isolated and sectioned to investigate the immune response within the CNS, which underlies the pathology of R-EAE and multiple sclerosis. FIG. 9 shows a reduction in immune cell infiltration within the spinal cord of animals treated with PLP$_{139-151}$-PLG that and was more similar to native tissue than to tissue from OVA$_{323-339}$-PLG treated animals. OVA$_{323-339}$-PLG treated animals had positive staining for CD45, CD4, and CD11b; whereas, PLP$_{139-151}$-PLG treated animals had minimal staining for these factors.

Figure 10A:
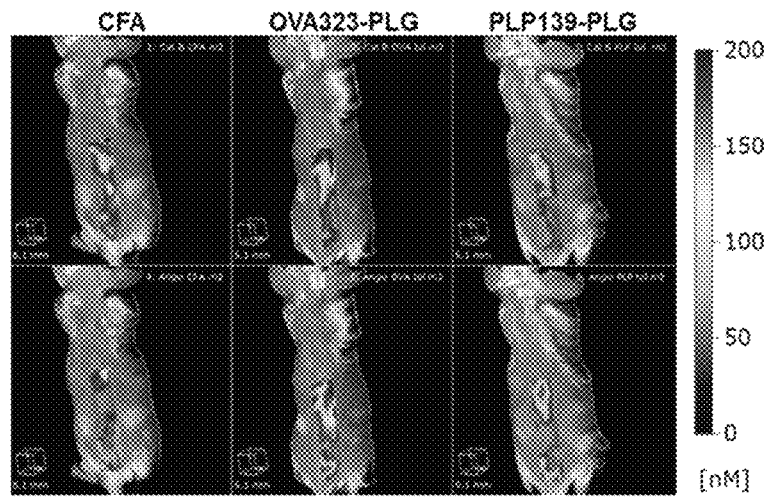
FIGS. 10A-10C show that administration of $PLP_{139-151}$-PLG particles inhibits blood brain barrier (BBB) disruption and macrophage activation in the spinal cord of treated mice. Animals were treated with either Complete Freund's Adjuvant (CFA), $OVA_{323-339}$ PLG particles, or $PLP_{139-151}$-PLG particles. The clinical scores and percent incidence of EAE were determined (FIG. 10B) and the spinal cords observed via in vivo imaging (FIG. 10A and FIG. 10C).
Figure 10B:
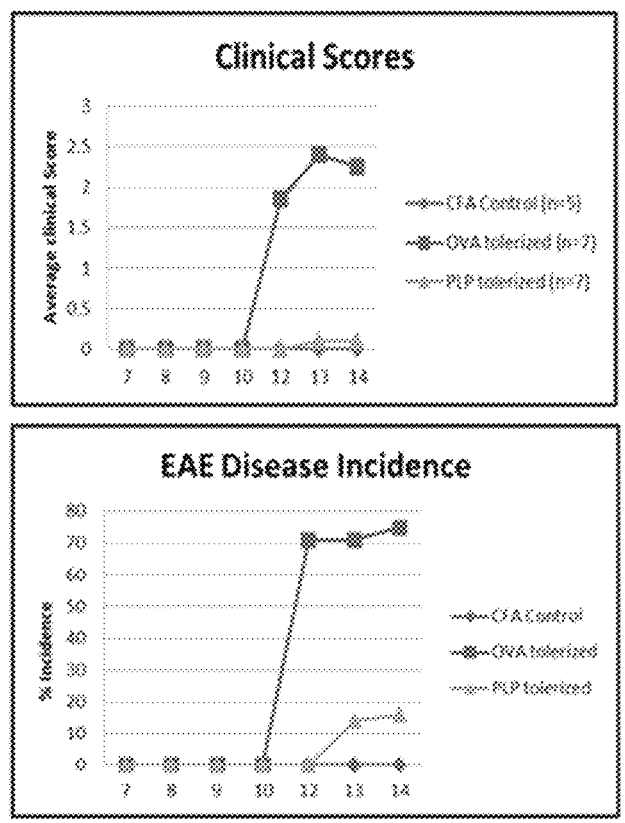
Figure 10C:
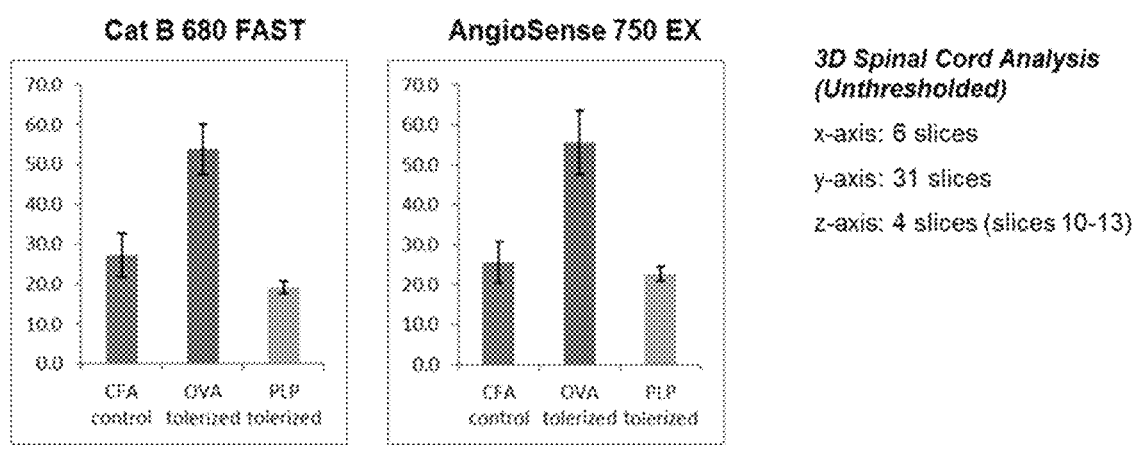
Figure 11A:
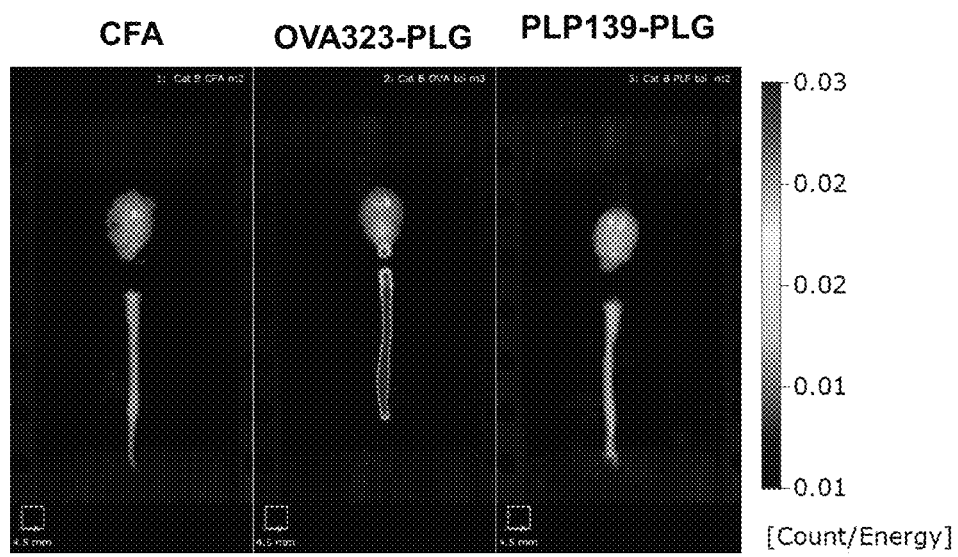
FIGS. 11A-11F show the spinal cords of treated mice via in vivo imaging.
Figure 11B:
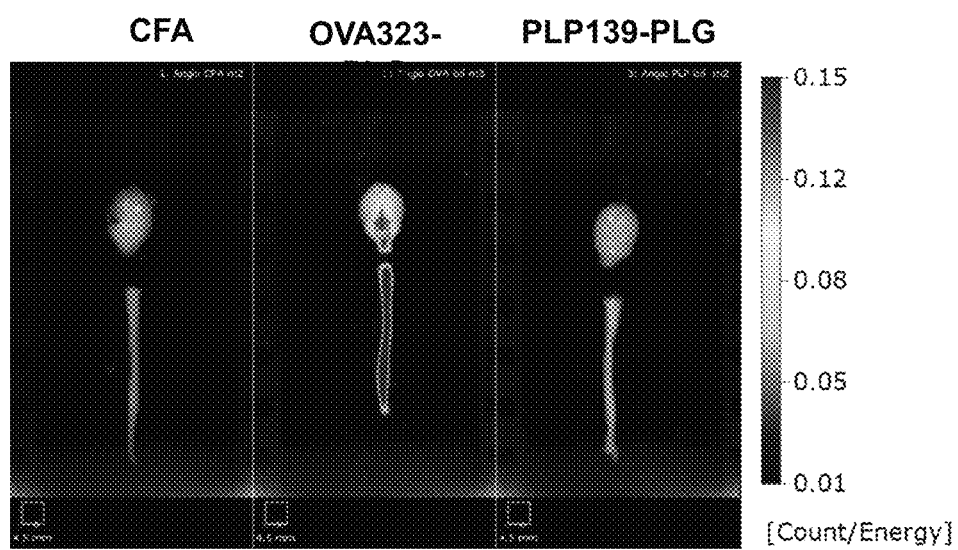
Figure 11C:
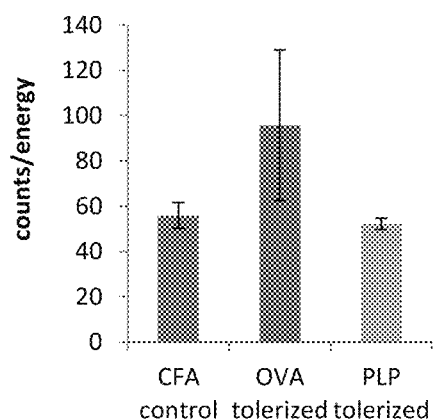
Figure 11D:
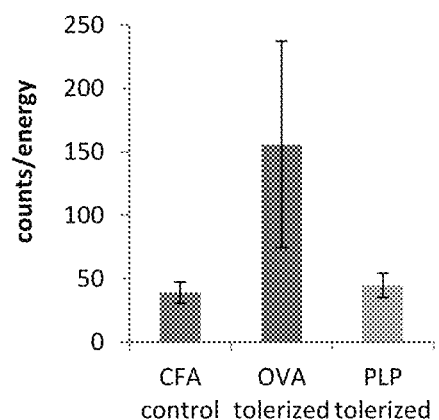
Figure 11E:
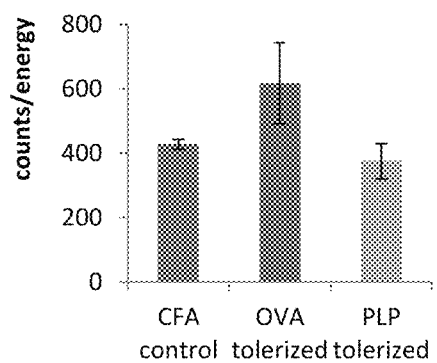
Figure 11F:
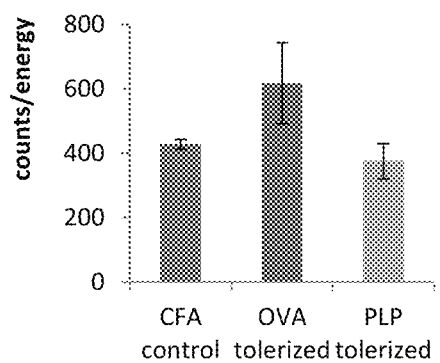

Administration of PLP$_{139-151}$-PLG particles also inhibits blood brain barrier (BBB) disruption and macrophage activation in the spinal cord of treated mice. Animals were treated with Complete Freund's Adjuvant (CFA), OVA$_{323-339}$ PLG particles, or PLP$_{139-151}$-PLG particles. The clinical scores and percent incidence of EAE were determined (FIG. 10B) and the spinal cords observed via in vivo imaging (FIGS. 10A and 11). Angiosense measures vascular leak in the CNS and prosense reports activated macrophages (cathepsin activation cleaves the reporter revealing the fluorescent signal). The bar graphs give the numerical numbers to the signal strength shown in the brain and SC scans.

Figure 12:
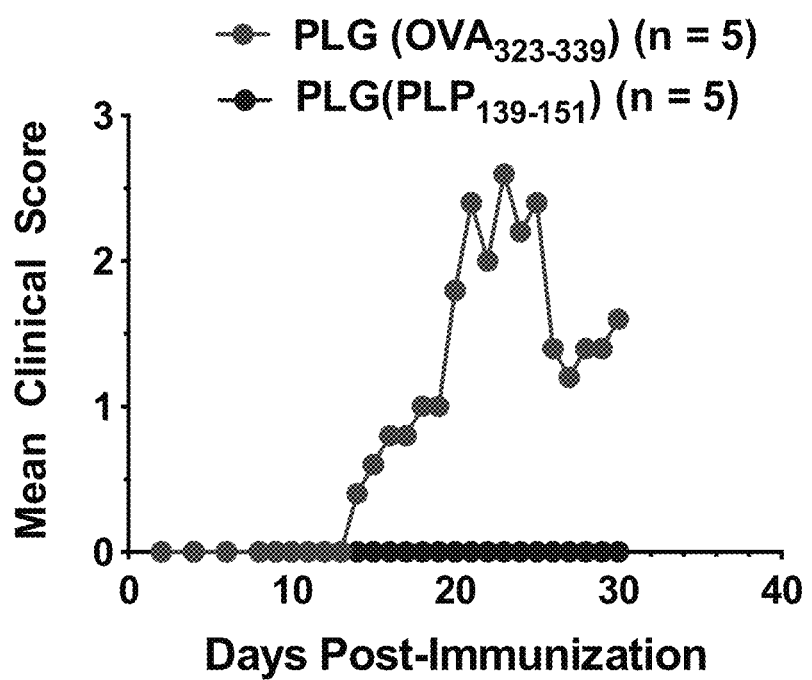
FIG. 12 shows that the administration of PLG particles in which $PLP_{139-151}$ has been encapsulated inhibits the induction of R-EAE in mice. The ability to encapsulate autoantigens allows for the used of complex mixtures of proteins or even organ homogenates not possible with surface binding, allowing for more antigen coverage and thus more effectively deal with epitope spreading.

Tolerance can also be induced by particles in which the antigen has been encapsulated. FIG. 12 shows that the administration of PLG particles in which PLP$_{139-151}$ has been encapsulated inhibits the induction of R-EAE in mice. The ability to encapuslate autoantigens allows for the used of complex mixtures of proteins or even organ homogenates to achieve more antigen coverage and thus more effectively deal with epitope spreading.

Example 8

Figure 13:
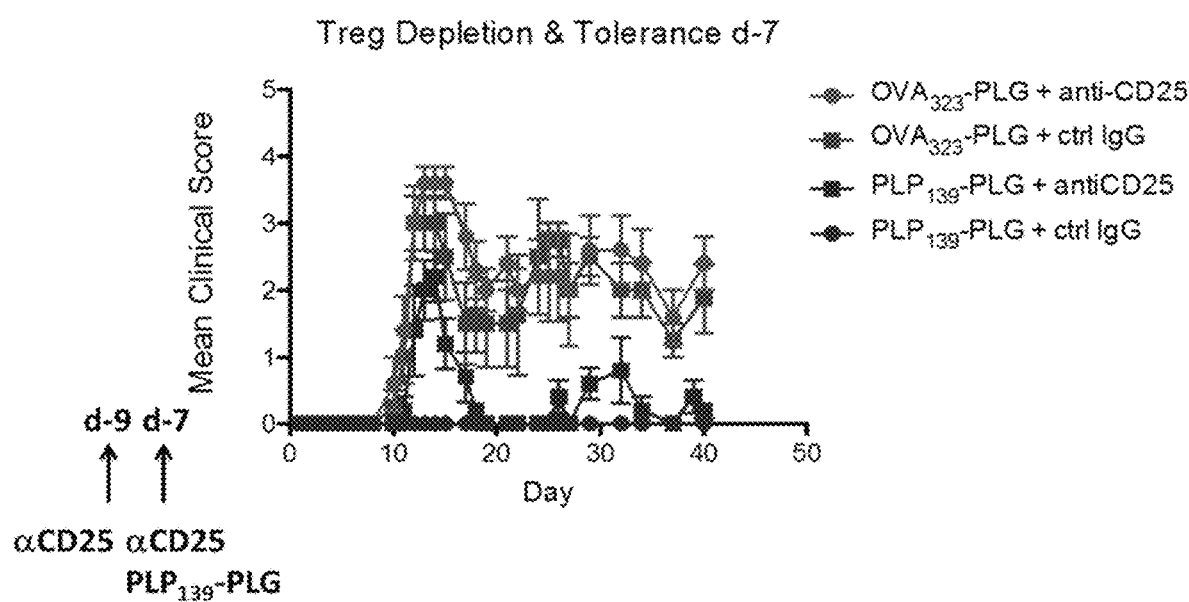
FIG. 13 shows that animals treated with the $PLP_{139-151}$-PLG particles and an anti-CD25 antibody demonstrated, at times, a greater mean clinical score than those animals treated with PLP$_{139-151}$-PLG particles and a control IgG antibody.

Tolerance Induced by PLP-$_{139-151}$ Coupled PLGA Particles is Partially Dependent on the Expansion/Activation of Regulatory T-Cells SJL/J mice were treated with an anti-CD25 antibody, a common marker for regulatory T cells (Tregs) on Day −9, and then on Day −7 were treated with either OVA$_{323-339}$ PLG particles and anti-CD25 antibody, OVA$_{323-339}$ PLG particles and a control IgG antibody, PLP$_{139-151}$-PLG particles and an anti-CD25 antibody, or PLP$_{139-151}$-PLG particles and a control IgG antibody. As shown in FIG. 13, animals treated with the PLP$_{139-151}$-PLG particles and the anti-CD25 antibody demonstrated, at times, a greater mean clinical score than those animals treated with PLP$_{139-151}$-PLG particles and a control IgG antibody. This confirms that Tregs, or at least T cells expressing CD25, play a role in the initiation of tolerance.

Example 9

Figure 14A:
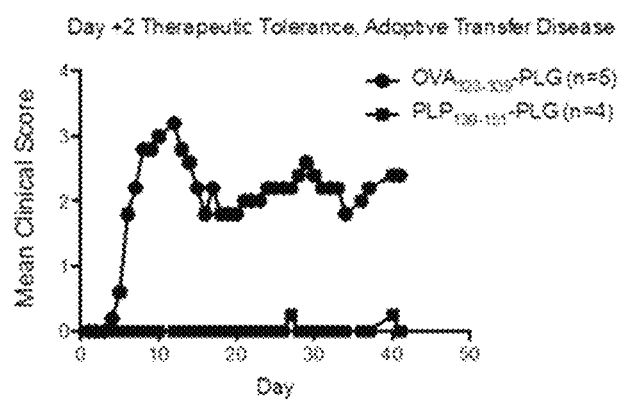
FIGS. 14A-14E show that therapeutic tolerance induced by PLP$_{139-151}$-PLG particles in active and adoptive EAE. Adoptive EAE was induced in six to eight-week old female SJL/J mice by adoptive transfer of 2.5×10$^6$ PLP$_{139-151}$-activated blasts. Mice were injected iv with PLP$_{139-151}$ (squares) or OVA$_{323-339}$ (circles) peptide coupled to 500 nm PLG nanoparticles 2 days (FIG. 14A), 14 days (FIG. 14C), 18 days (FIG. 14E), or 21 days (FIG. 14F) following disease induction. Clinical disease scores were compared to those following treatment with antigen-coupled splenocytes (FIG. 14A). Brain and spinal cord were collected from PLP$_{139-151}$- or OVA$_{323-339}$-tolerized mice for histological analysis on day 42. Sections from mice from panel A were stained for PLP protein and CD45 (FIG. 14B). Spinal cord sections from mice from panel (FIG. 14C) were stained with Luxol Fast Blue (FIG. 14D). Areas of demyelination and cellular infiltration are indicated by arrows.
Figure 14B:
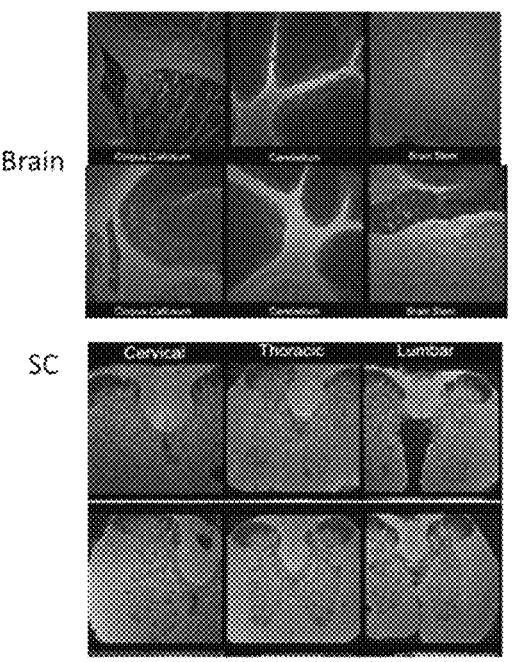
Figure 14C:
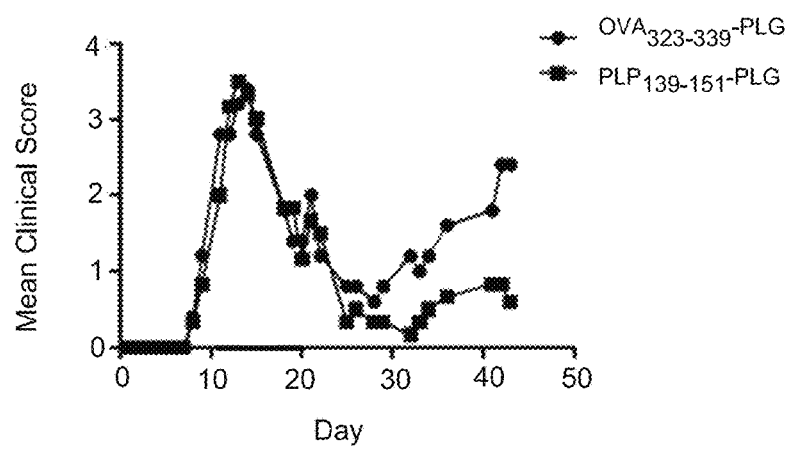
Figure 14D:
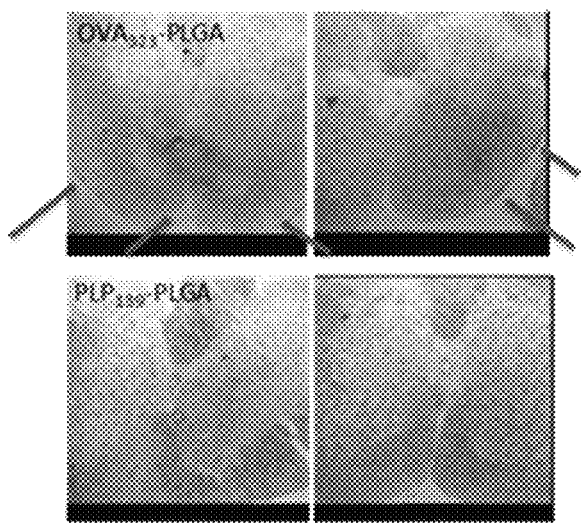
Figure 14E:
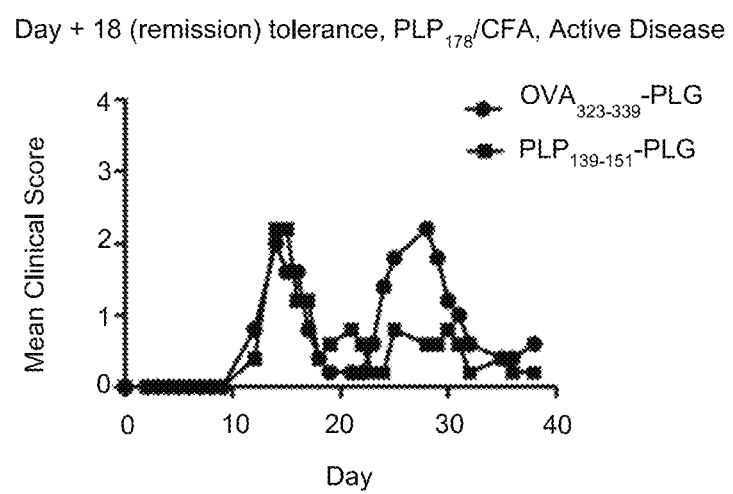

Therapeutic Tolerance is Induced by PLP$_{139-151}$-PLG Particles in Active and Adoptive EAE Therapeutic tolerance induced by PLP$_{139-151}$-PLG particles was compared in active and adoptive EAE. Adoptive EAE was induced in six to eight-week old female SJL/J mice by adoptive transfer of 2.5×10$^6$ PLP$_{139-151}$-activated blasts. Mice were injected iv with PLP$_{139-151}$ (squares) or OVA$_{323-339}$ (circles) peptide coupled to 500 nm PLG nanoparticles 2 days (FIG. 14A), 14 days (FIG. 14C), 18 days (FIG. 14E), or 21 days (FIG. 14F) following disease induction. Clinical disease scores were compared to those following treatment with antigen-coupled splenocytes (FIG. 14A). Brain and spinal cord were collected from PLP$_{139-151}$- or OVA$_{323-339}$-tolerized mice for histological analysis on day 42. Sections from mice from panel A were stained for PLP protein and CD45 (FIG. 14B). Spinal cord sections from mice from panel C were stained with Luxol Fast Blue (FIG. 14D). Areas of demyelination and cellular infiltration are indicated by arrows. The results show that tolerance is induced by PLP$_{139-151}$-PLG particles in mice with adoptive EAE.

Figure 15A:
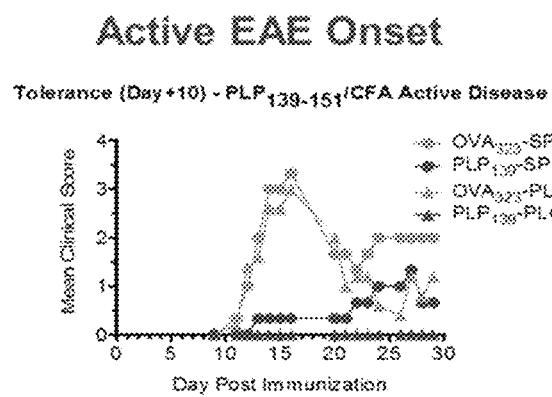
FIGS. 15A-15B show graphs depicting the mean clinical scores of mice with either active EAE and adoptive EAE after treatment with either SP or PLG particles conjugated to OVA$_{323-339}$ or PLP$_{139-151}$. Mice were injected iv with PLP$_{139-151}$-SP, PLP$_{139-151}$-PLG, or OVA$_{323-339}$-SP, or OVA$_{323-339}$-PLG peptide coupled to 500 nm nanoparticles 10 days (FIG. 15A) or 2 days (FIG. 15B) following disease induction and the mean clinical score was determined. In both cases, administration of PLP$_{139-151}$-PLG particles induces tolerance in the mice.
Figure 15B:
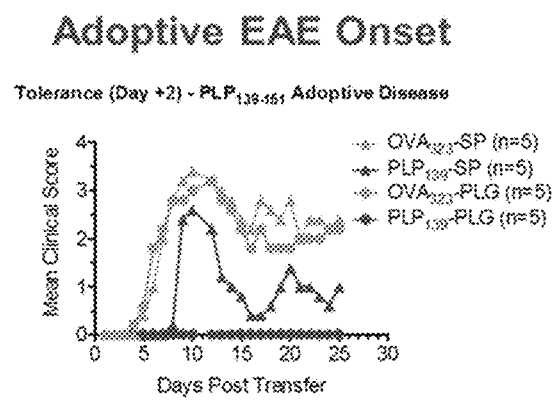

FIG. 15 shows graphs depicting the mean clinical scores of mice with active EAE and adoptive EAE after treatment with either SP or PLG particles conjugated to OVA$_{323-339}$ or PLP$_{139-151}$. Mice were injected iv with PLP$_{139-151}$-SP, PLP$_{139-151}$-PLG, or OVA$_{323-339}$-SP, or OVA$_{323-339}$-PLG peptide coupled to 500 nm nanoparticles 10 days (FIG. 15A) or 2 days (FIG. 15B) following disease induction and the mean clinical score was determined. In both cases, administration of PLP$_{139-151}$-PLG particles reduced disease, indicative of tolerance induction.

Figure 16A:
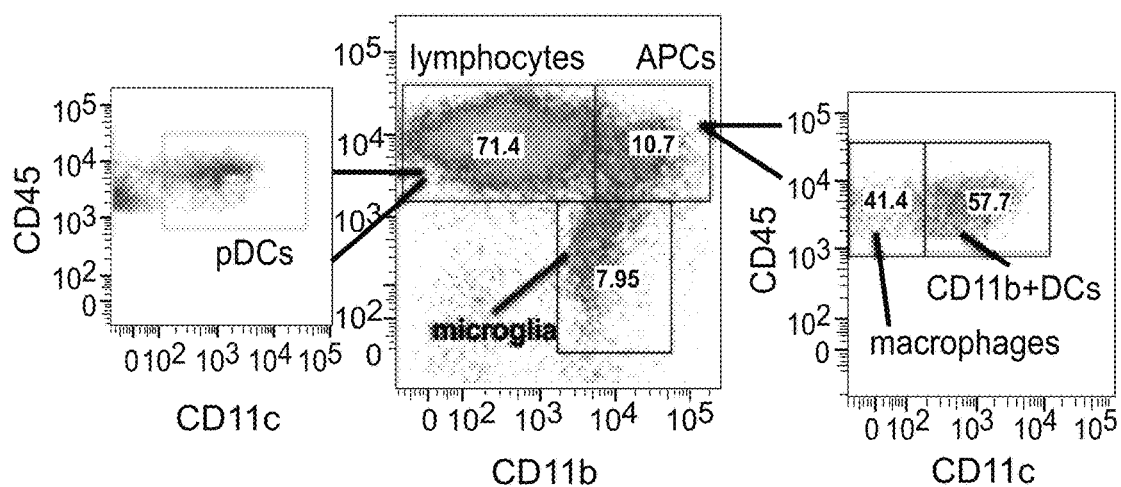
FIGS. 16A-16H show the infiltration of central nervous system immune cells is also drastically reduced in PLP-PLG tolerized mice. SJL/J mice were injected i.v. with 500 nm PLG nanoparticles coupled with PLP$_{139-151}$ (squares) or OVA$_{323-339}$ (circles) 2 days following EAE induction by adoptive transfer. At the peak of disease (day 14) brains and spinal cords were removed and the number of lymphocytes (FIG. 16B), APCs (FIG. 16C), microglia (FIG. 16D), peripheral dendritic cells (FIG. 16E), myeloid dendritic cells (FIG. 16F) and macrophages (FIG. 16G) were enumerated by flow cytometry. The gating strategy for these populations is depicted in (FIG. 16A). CNS cell preparations were stimulated with PMA and ionomycin for 5 h prior to intracellular staining for IL-17A and IFN-γ (H).
Figure 16B:
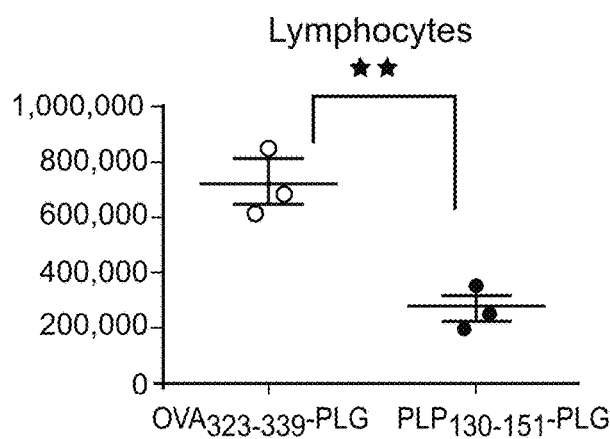
Figure 16C:
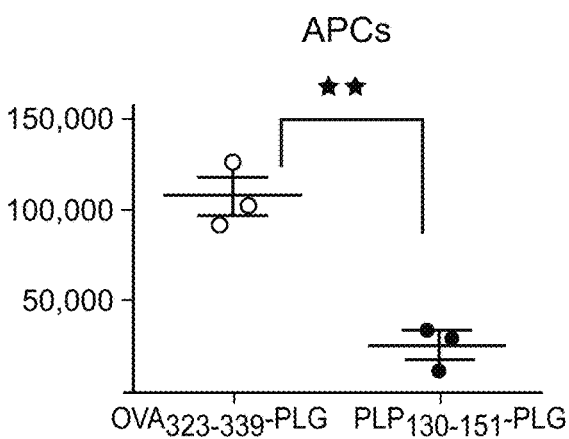
Figure 16D:
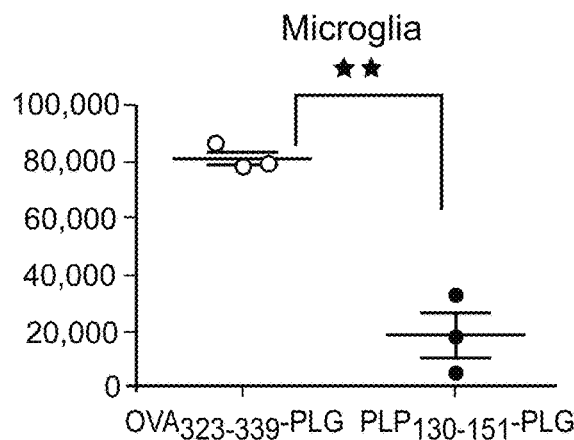
Figure 16E:
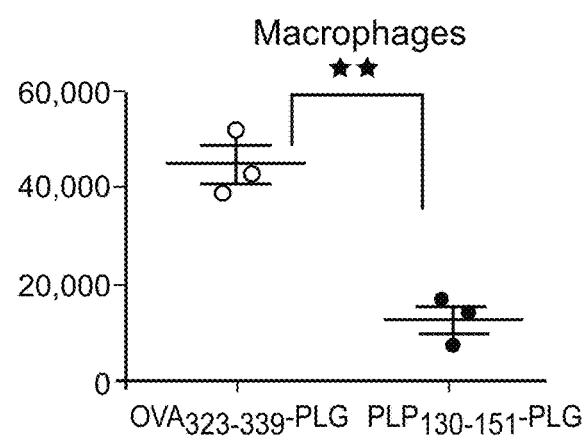
Figure 16F:
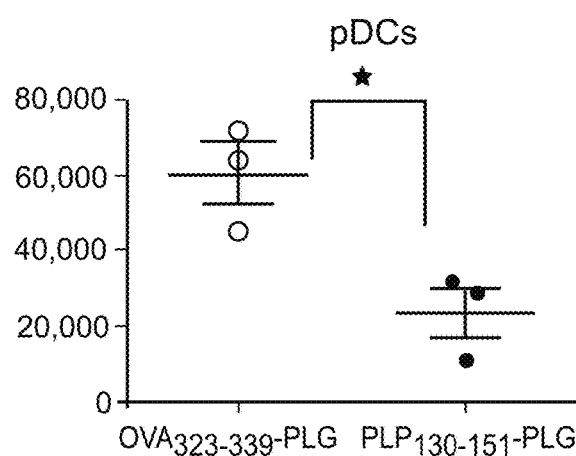
Figure 16G:
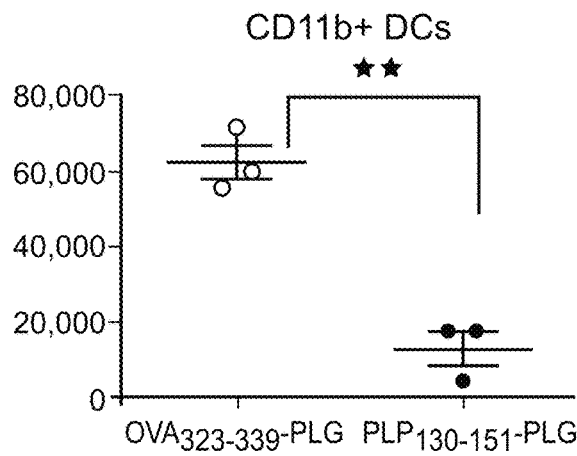
Figure 16H:
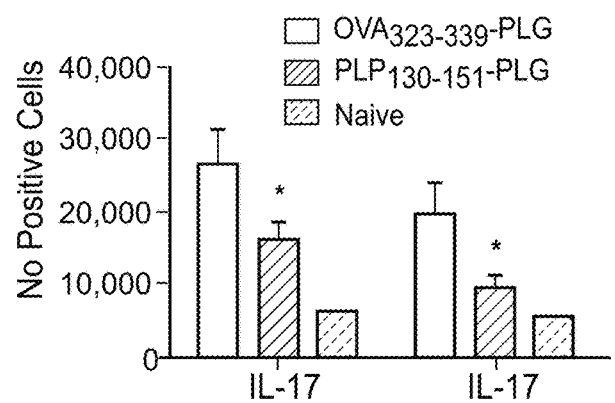

The infiltration of central nervous system immune cells is also drastically reduced in PLP-PLG tolerized mice. SJL/J mice were injected i.v. with 500 nm PLG nanoparticles coupled with PLP$_{139-151}$ (squares) or OVA$_{323-339}$ (circles) 2 days following EAE induction by adoptive transfer. At the peak of disease (day 14) brains and spinal cords were removed and the number of lymphocytes (FIG. 16B), APCs (FIG. 16C), microglia (FIG. 16D), peripheral dendritic cells (FIG. 16E), myeloid dendritic cells (FIG. 16F) and macrophages (FIG. 16G) were enumerated by flow cytometry. The gating strategy for these populations is depicted in (FIG. 16A). CNS cell preparations were stimulated with PMA and ionomycin for 5 h prior to intracellular staining for IL-17A and IFN-γ (FIG. 16H).

Example 10

Treatment with an Anti-PD-1 Monoclonal Antibody Abrogates Tolerance Induction with PLG Nanoparticles Encapsulating PLP$_{139-151}$ in Adoptive Transfer EAE To test the effect of treatment with an anti-PD-1 antibody on PLP$_{139-151}$ induced tolerance in mice with adoptive EAE, on Day 0, mice received 3×10$^6$ PLP$_{139-151}$ activated T-cell blasts via intravenous administration. On Day 2, they received PLP$_{139-151}$ or OVA$_{323-339}$ encapsulated in PLG particles via intravenous administration with either PBS or an anti-PD-1 antibody. On days 4, 6, 8, 10, and 12 all animals received either 250 μg anti-PD-1 antibody or PBS.

Figure 17:
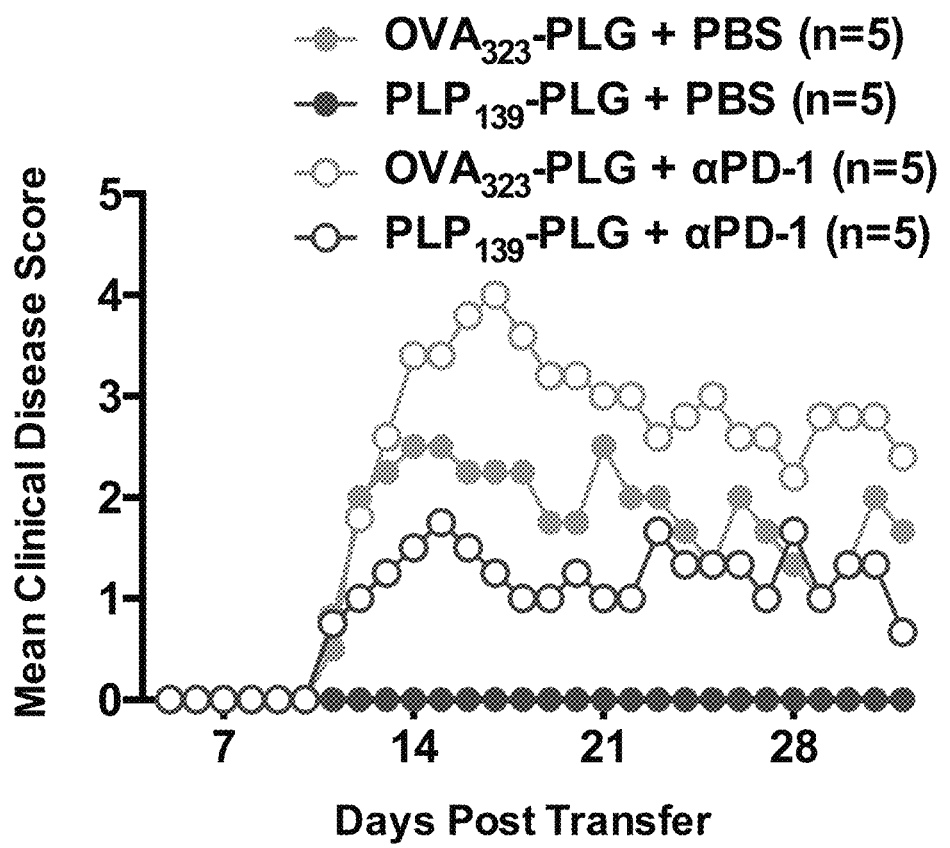
FIG. 17 shows that administration of the PLP$_{139-151}$ peptide encapsulated in a PLG particle induces tolerance when the particle is administered with PBS. However, administration of the anti-PD-1 antibody decreases this tolerance.

As shown in FIG. 17, administration of the PLP$_{139-151}$ peptide encapsulated in a PLG particle induces tolerance when the particle is administered with PBS. However, administration of the anti-PD-1 antibody decreases this tolerance.

Example 11

Treatment with an Agonistic Anti-CD40 Monoclonal Antibody Abrogates Tolerance Induction with PLG Nanoparticles Encapsulating PLP$_{139-151}$ in Adoptive Transfer EAE in an IL-12 Dependent Manner To test the effect of treatment with an agonistic anti-CD40 antibody on PLP$_{139-151}$ induced tolerance in mice with adoptive EAE, on Day 0, mice received 3×10$^6$ PLP$_{139-151}$ activated T-cell blasts via intravenous administration. On Day 2, the mice received PLP$_{139-151}$ or OVA$_{323-339}$ encapsulated in PLG particles via intravenous administration. On day 3, the animals received a control IgG2a antibody, an anti-CD40 antibody, or an anti-CD40 antibody and an anti-Il-12 antibody.

Figure 18:
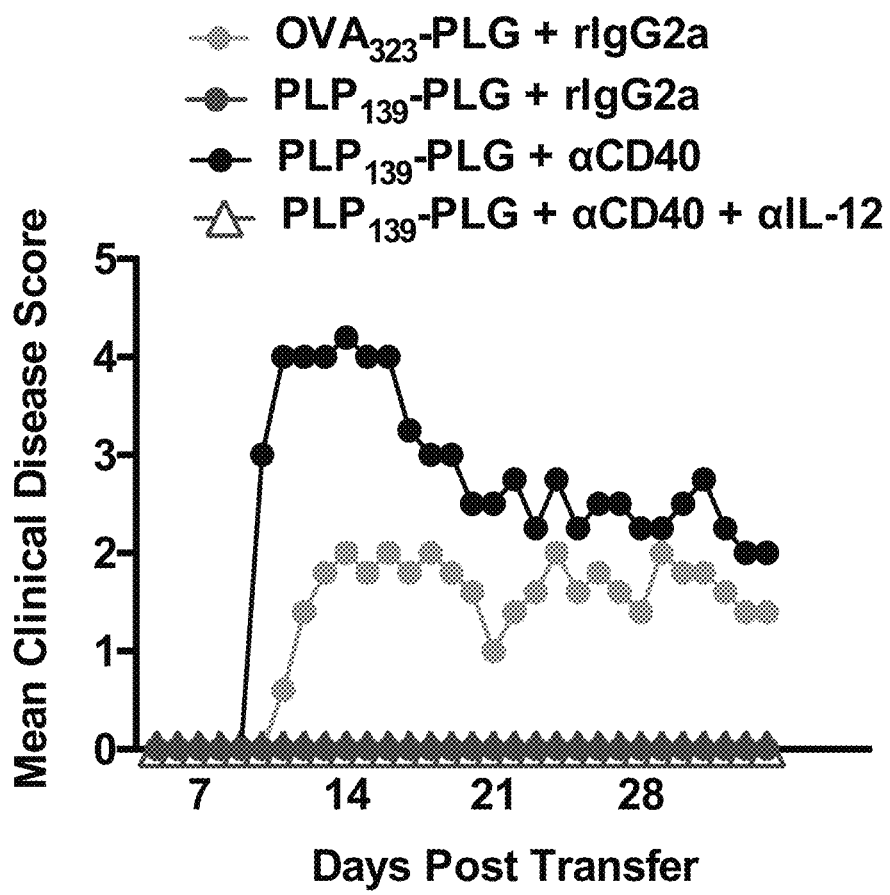
FIG. 18 shows that administration of the PLP$_{139-151}$ peptide encapsulated in a PLG particle induces tolerance when the particle is administered with PBS. Administration of an anti-CD40 antibody decreases this tolerance, but this decrease in tolerance is reversed by the addition of an anti-IL-12 antibody.
Figure 19A:
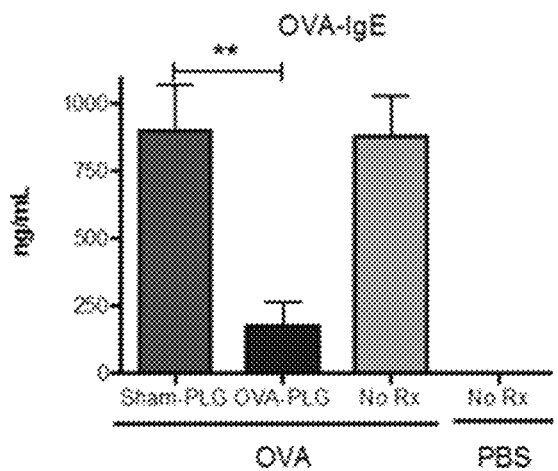
FIGS. 19A-19G show that the prophylactic administration of OVA-PLG decreased the secretion of IL-4, IL-5, IL-13 and IL-10, and reduced the levels of serum OVA IgE and eosinophils in the lung.
Figure 19D:
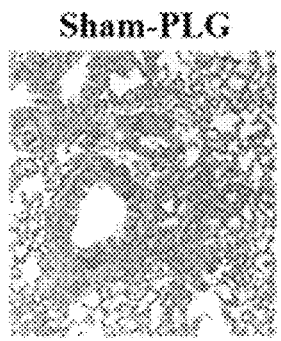
Figure 19B:
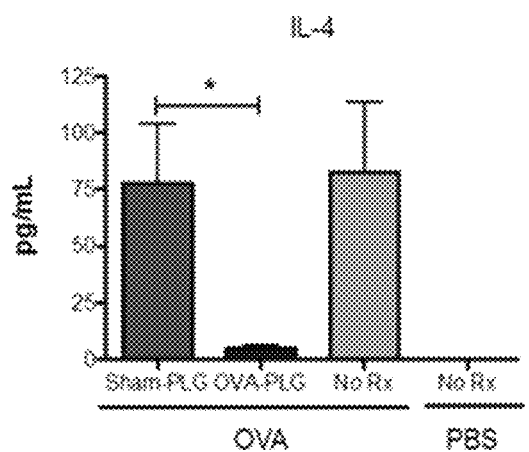
Figure 19B:
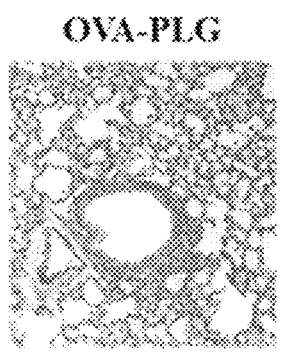
Figure 19C:
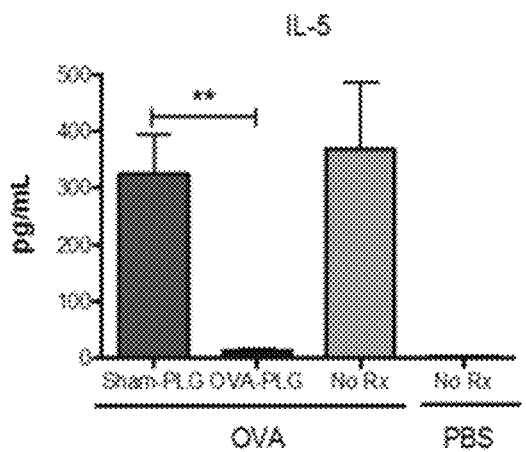
Figure 19E:
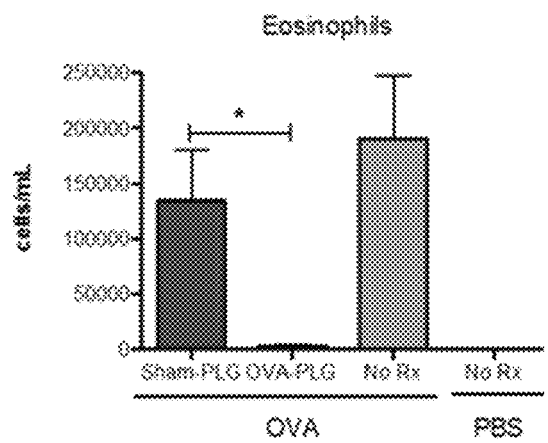
Figure 19F:
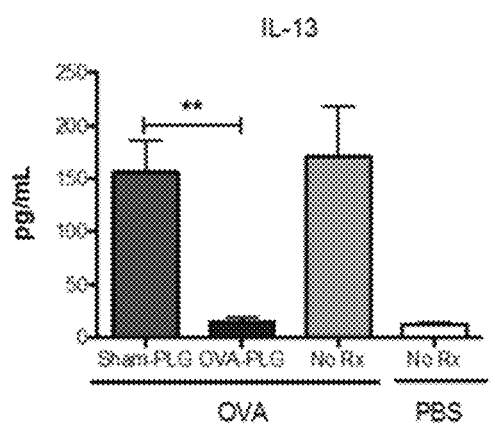
Figure 19G:
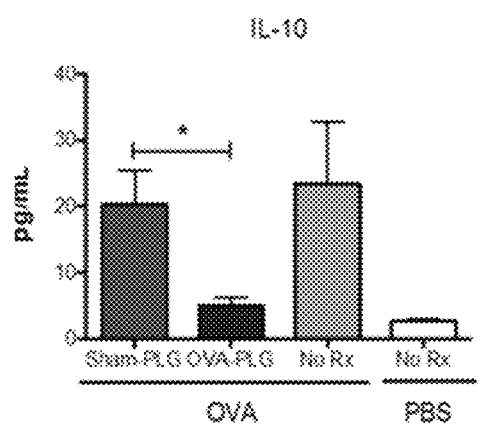

As shown in FIG. 18, administration of the $PLP_{139\text{-}151}$ peptide encapsulated in a PLG particle induces tolerance when the particle is administered with PBS. Administration of the agonistic anti-CD40 antibody decreases this tolerance, but this decrease in tolerance is reversed by the addition of an anti-IL-12 antibody.

Example 12

OVA Encapsulated in PLG Particles Prophylactically Inhibits Allergic Airway Inflammation and In Vivo OVA-Specific Th2 Responses To test the prophylactic effect of OVA encapsulated in PLG particles on airway inflammation, mice were treated intravenously with OVA-PLG at day −7. On day 0, the mice received intraperitoneal injections of OVA/Alum at a dose of 10 μg/mouse. On day 7, the mice were again treated intravenously with OVA-PLG and received another 10 μg/mouse ip injection of OVA/Alum on day 14. Between days 28 and 30, the mice were treated three times with aerosolized OVA.

As shown in FIG. 19, the prophylactic administration of OVA-PLG decreased the secretion of IL-4, IL-5, IL-13 and IL-10, and reduced the levels of serum OVA IgE and eosinophils in the lung.

Figure 20A:
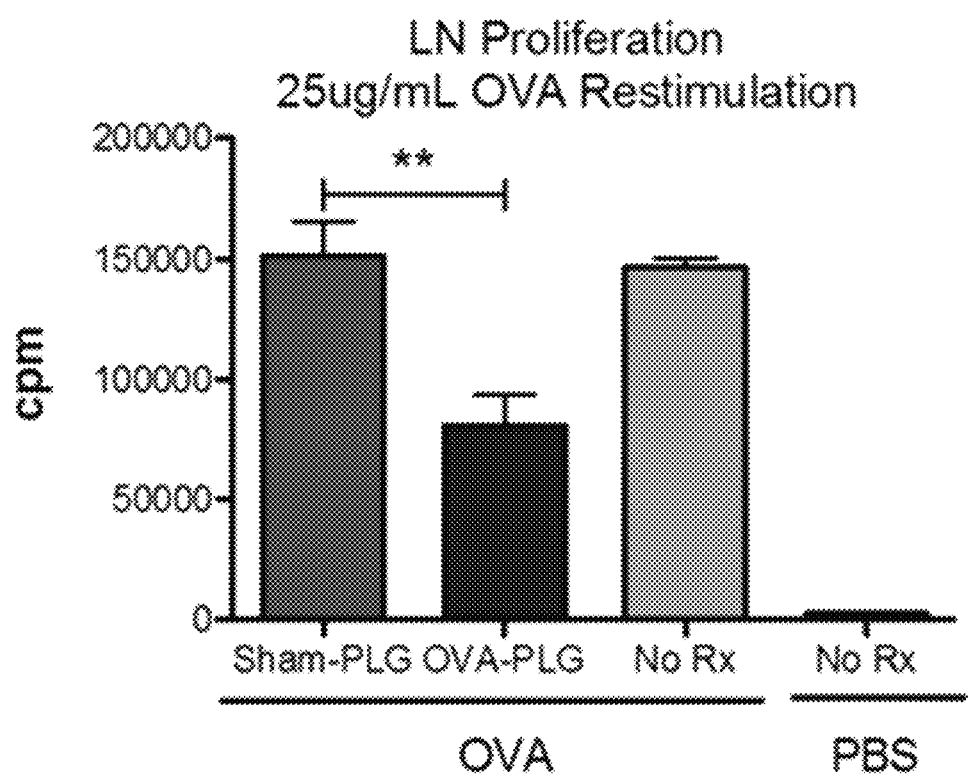
FIGS. 20A-20B show that OVA encapsulated in PLG particles prophylactically inhibits OVA-specific in vitro recall responses from mediastinal lymph nodes. The lymph node proliferation observed after restimulation with 25 µg OVA is decreased in those animals treated with OVA-PLG (FIG. 20A). Moreover treatment with OVA-PLG decreases the release of cytokines after restimulation with OVA. Levels of IL-4, IL-5, IL-13, and IL-10 are decreased in mice treated with OVA-PLG (FIG. 20B).
Figure 20B:
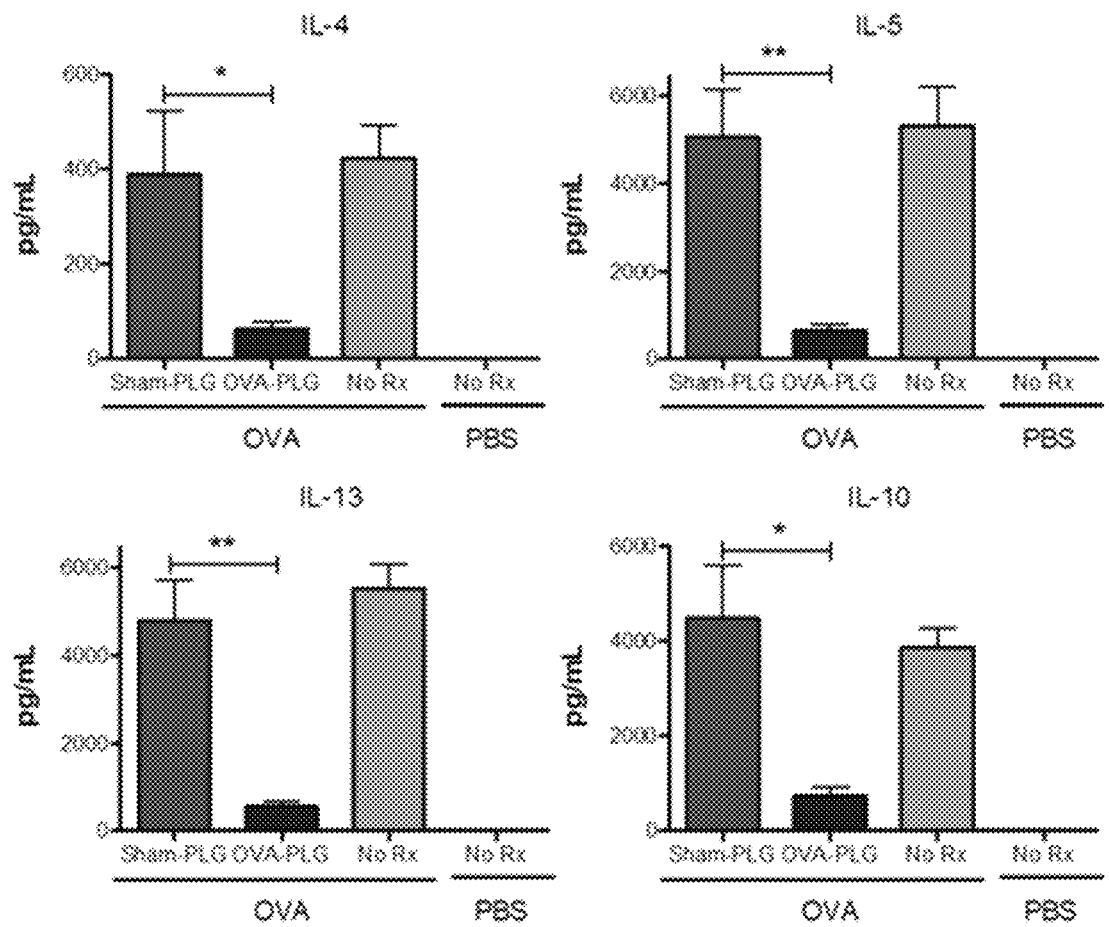

OVA Encapsulated in PLG particles prophylactically inhibits OVA-specific in vitro recall responses from mediastinal lymph nodes. As shown in FIG. 20A, the lymph node proliferation observed after restimulation with 25 μg OVA is decreased in those animals treated with OVA-PLG. Moreover treatment with OVA-PLG decreases the release of cytokines after restimulation with OVA. FIG. 20B shows that levels of IL-4, IL-5, IL-13, and IL-10 are decreased in mice treated with OVA-PLG.

Example 13

OVA Encapsulated in PLG Particles Therapeutically Inhibits Allergic Airway Inflammation and In Vivo OVA-Specific Th2 Responses To test the therapeutic effect of OVA encapsulated in PLG particles on airway inflammation, mice were treated intraperitoneally with OVA/Alum at a dose of 10 μg/mouse on day 0 and day 14. The mice were intravenously administered with OVA-PLG on days 28, and 42. Between days 56-58, the mice were treated three times with aerosolized OVA.

Figure 21B:
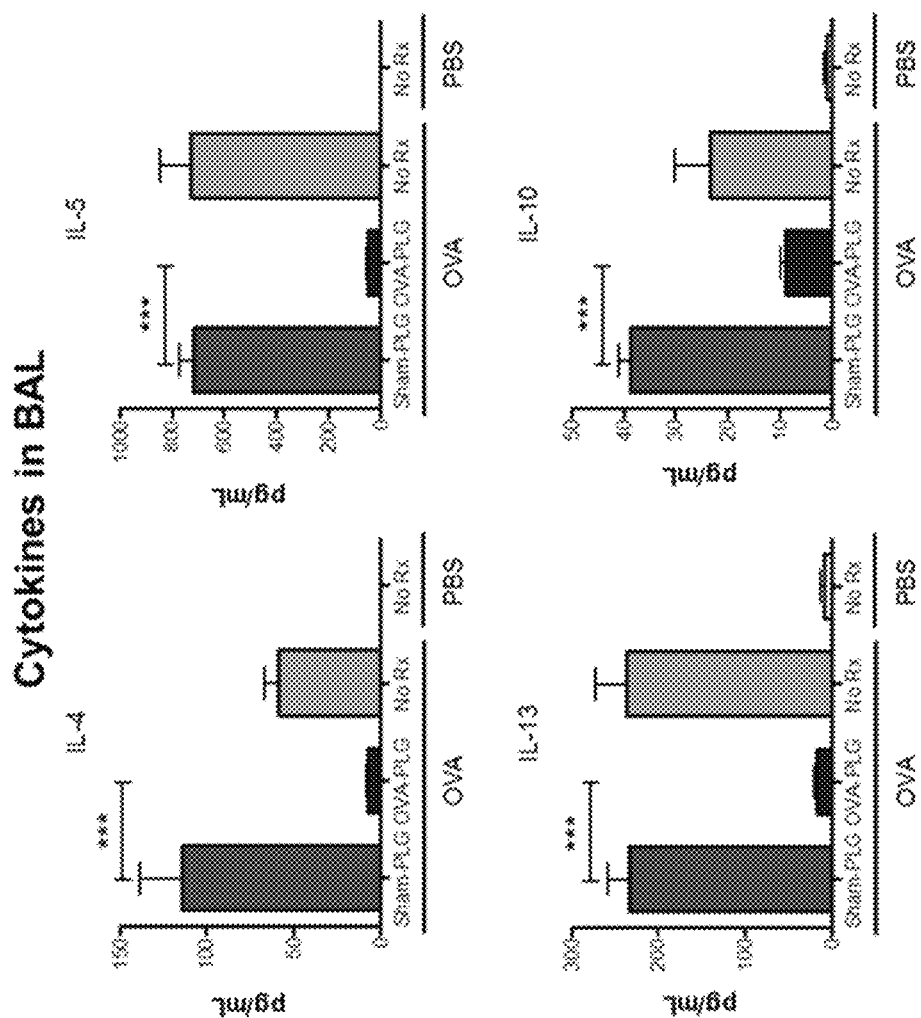
FIGS. 21A and 21B show that the therapeutic administration of OVA-PLG decreased the secretion of IL-4, IL-5, IL-13 and IL-10, and reduced the levels of serum OVA IgE and eosinophils in the lung.
Figure 21A:
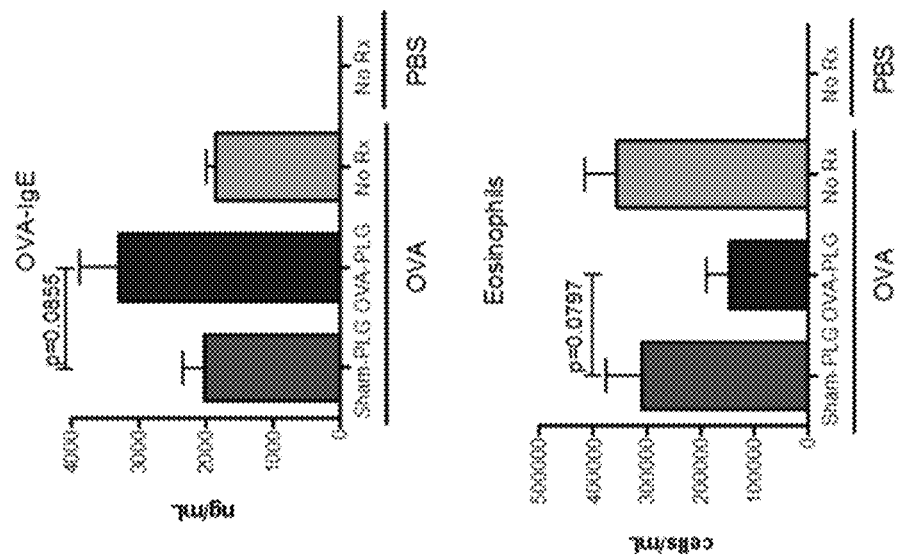

As shown in FIG. 21, the therapeutic administration of OVA-PLG decreased the secretion of IL-4, IL-5, IL-13 and IL-10, and reduced the levels of serum OVA IgE and eosinophils in the lung.

Figure 22A:
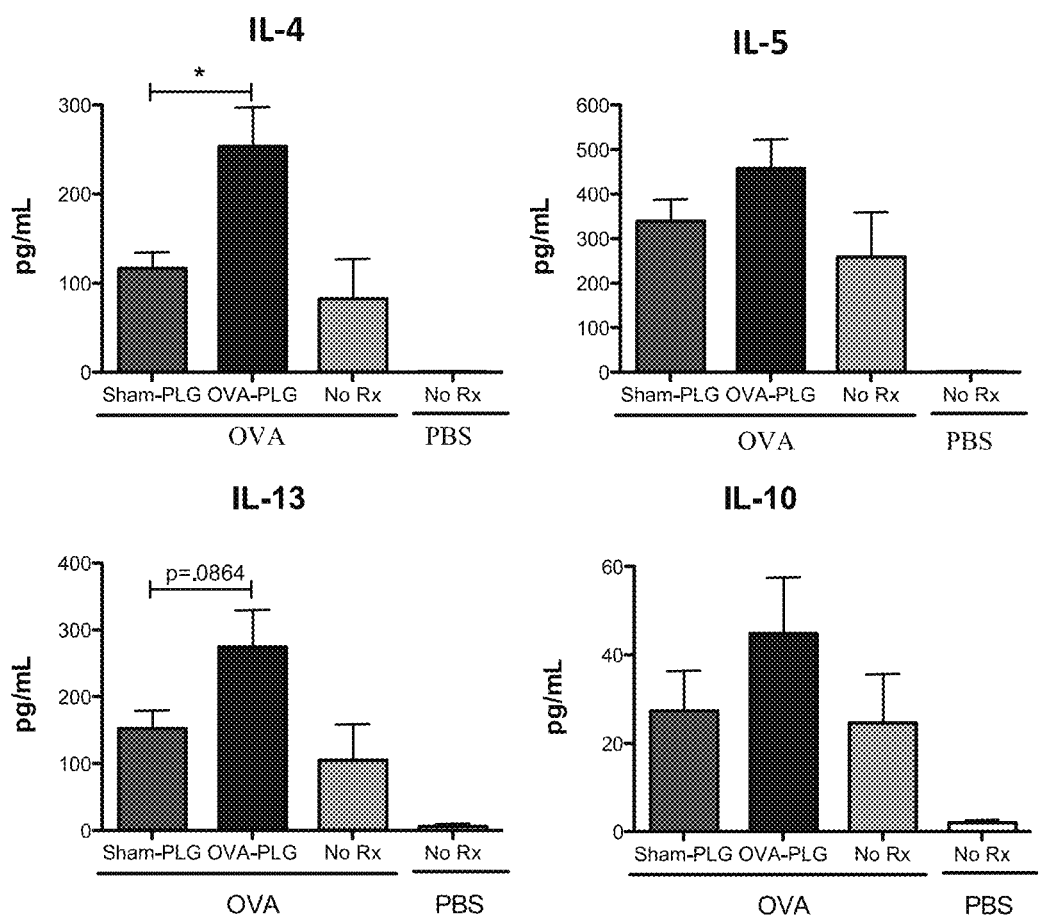
FIGS. 22A-22B show that OVA encapsulated in PLG particles therapeutically downregulates OVA-Specific Th2 Cytokines in the BAL fluid better than OVA-coupled PLG particles. Mice were treated intraperitoneally with OVA/Alum at a dose of 10 µg/mouse on day 0 and day 14. The mice were intravenously administered with either OVA-coupled to PLG particles or OVA encapsulated in PLG particles on days 28, and 42. Between days 56-58, the mice were treated three times with aerosolized OVA. The graphs depict cytokine secretion when the animals were treated with either OVA coupled to PLG particles (FIG. 22A) or OVA encapsulated within PLG particles (FIG. 22B).
Figure 22B:
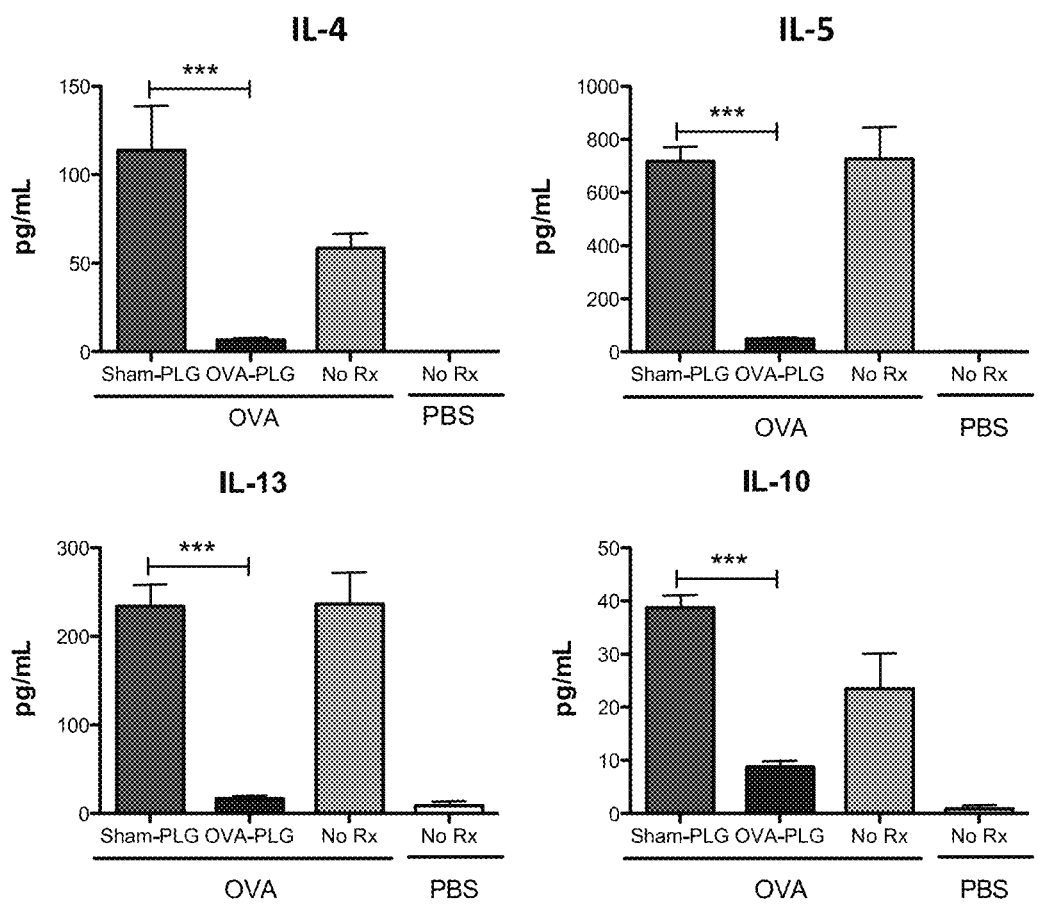

FIG. 22 shows OVA Encapsulated in PLG particles therapeutically downregulates OVA-Specific Th2 Cytokines in the BAL Fluid Better than OVA-coupled PLG particles. The animals were treated as described above except that on days 28 and 42, the mice were treated with either OVA encapsulated in PLG particles, or OVA coupled to PLG particles. Surprisingly, the encapsulated OVA inhibited the secretion of Th2 cytokines more than the OVA peptide coupled to the surface of the PLG particle.

Example 14

Tolerance Induced by Chromogranis A p31 Peptide-PLG Particles Inhibits Type 1 Diabetes Type 1 diabetes was induced in BDC2.5 mice by isolating spleen, axillary, brachial, inguinal, and pancreatic lymph node cells from mice at 3 weeks. The isolated cells were cultured and activated in vitro by incubating $2\times10^6$ cells/mL with 0.5 μM p31 peptide for 96 hours. $5\times10^6$ cells were transferred via intravenous administration to NOD.SCID mice (6-8 weeks) at Time 0. The mice were tolerized via intravenous administration with p31 or $MOG_{35\text{-}55}$ peptide coupled to SP or PLG 2 hours to 3 days later.

Figure 23A:
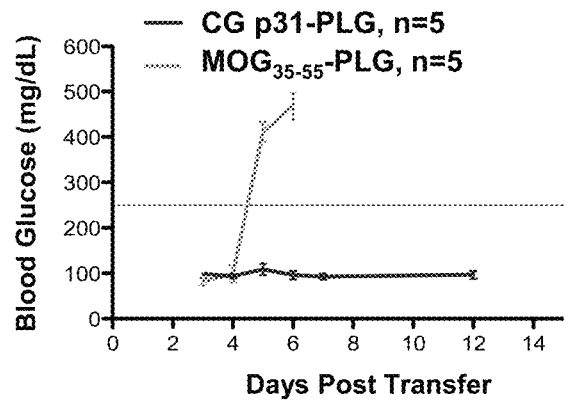
FIGS. 23A-23C show the blood glucose levels of type 1 diabetic animals after treatment with p31-PLG particles. Administration of the p31 peptide coupled PLG particles resulted in lower blood glucose levels compared to those seen after administration with the MOG$_{35-55}$ peptide coupled particles (FIG. 23A and FIG. 23B). The percent of IFNγ secreting cells observed in the animals was also reduced in the p31-PLG treated mice compared with the MOG$_{35-55}$ peptide-PLG treated mice (FIG. 23C).
Figure 23B:
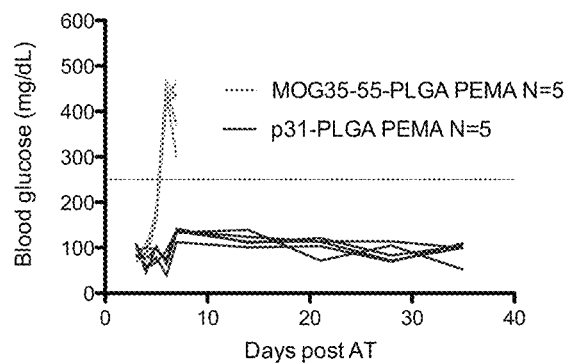
Figure 23C:
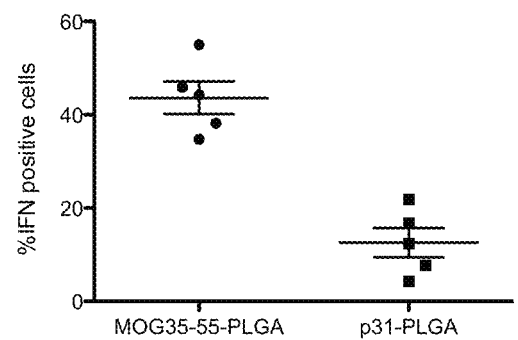
Figure 24A:
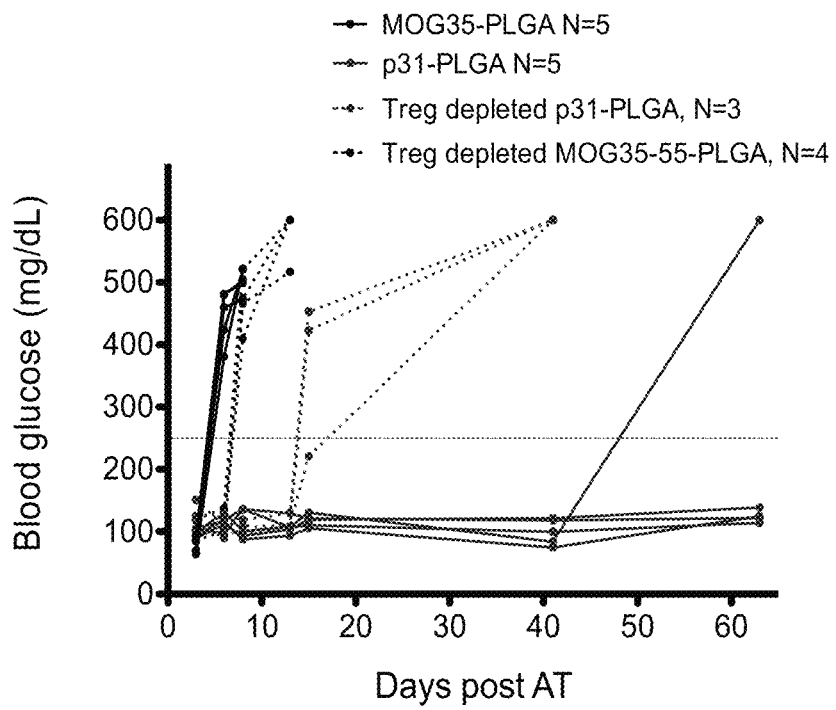
FIGS. 24A-24B show p31-PLG induced tolerance requires Tregs. Type 1 diabetes was induced in mice by adoptive transfer. Two hours after the activated cells were transferred to the NOD.SCID mice, the mice were tolerized with either p31-PLG or MOG$_{35-55}$ PLG particles. Depletion of Tregs abrogates the tolerance induced by administration of p31-PLG particles.
Figure 24B:
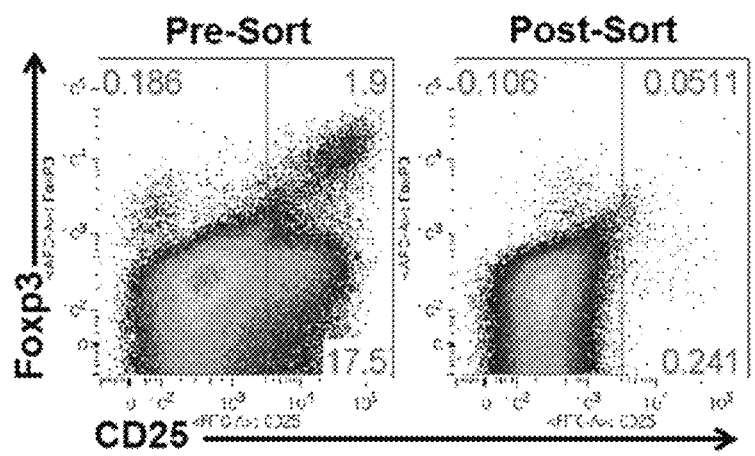

FIGS. 23A and 23B show the blood glucose levels in the animals after treatment. Administration of the p31 peptide coupled PLG resulted in lower blood glucose levels compared to those seen after administration with the $MOG_{35\text{-}55}$ peptide coupled particles. FIG. 23C shows that the percent of IFNγ secreting cells observed in the animals was also reduced in the p31-PLG treated mice compared with the $MOG_{35\text{-}55}$ peptide-PLG treated mice.

p31-PLG induced tolerance requires Tregs. Type 1 diabetes was induced in mice as described above, and 2 hours after the activated cells were transferred to the NOD.SCID mice, the mice were tolerized with either p31-PLG or $MOG_{35\text{-}55}$ PLG particles. As shown in FIG. 24, depletion of Tregs abrogates the tolerance induced by administration of p31-PLG particles.

Example 15

Figure 25:
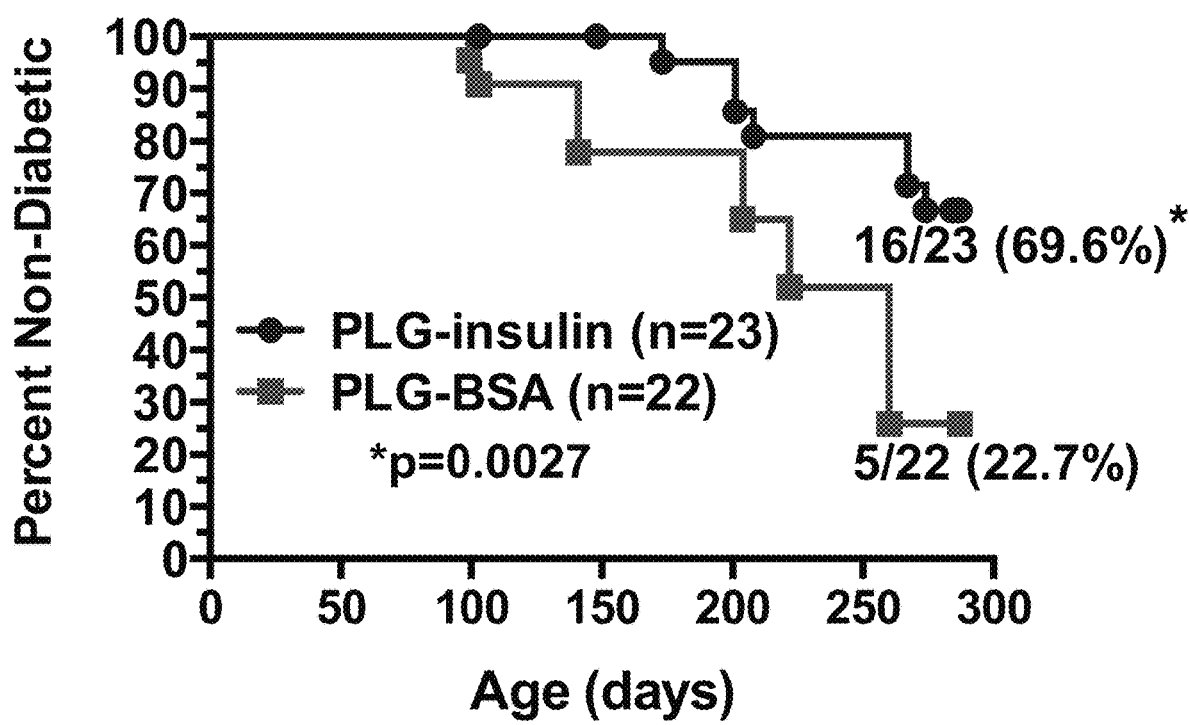
FIG. 25 shows administration of insulin coupled PLG particles significantly increased the percentage of mice that did not develop diabetes over 300 days (69.6% compared to 22.7%; p=0.0027). NOD mice were treated with either BSA (N=22) or insulin (N=23) coupled PLG particles via intravenous administration at 6, 8, and 10 weeks of age. The mice were then assayed for the development of diabetes.

Tolerance Induced by Insulin-Coupled PLG Particles Inhibits the Development of Spontaneous Type 1 Diabetes in NOD Mice NOD mice were treated with either BSA (N=22) or insulin (N=23) coupled PLG particles via intravenous administration at 6, 8, and 10 weeks of age. The mice were then assayed for the development of diabetes which was defined as blood glucose >250 mg/dL. As shown in FIG. 25, administration of the insulin coupled PLG particles significantly increased the percentage of mice that did not develop diabetes over 300 days (69.6% compared to 22.7%; p=0.0027).

Example 16

Engraftment Kinetics

Figure 26:
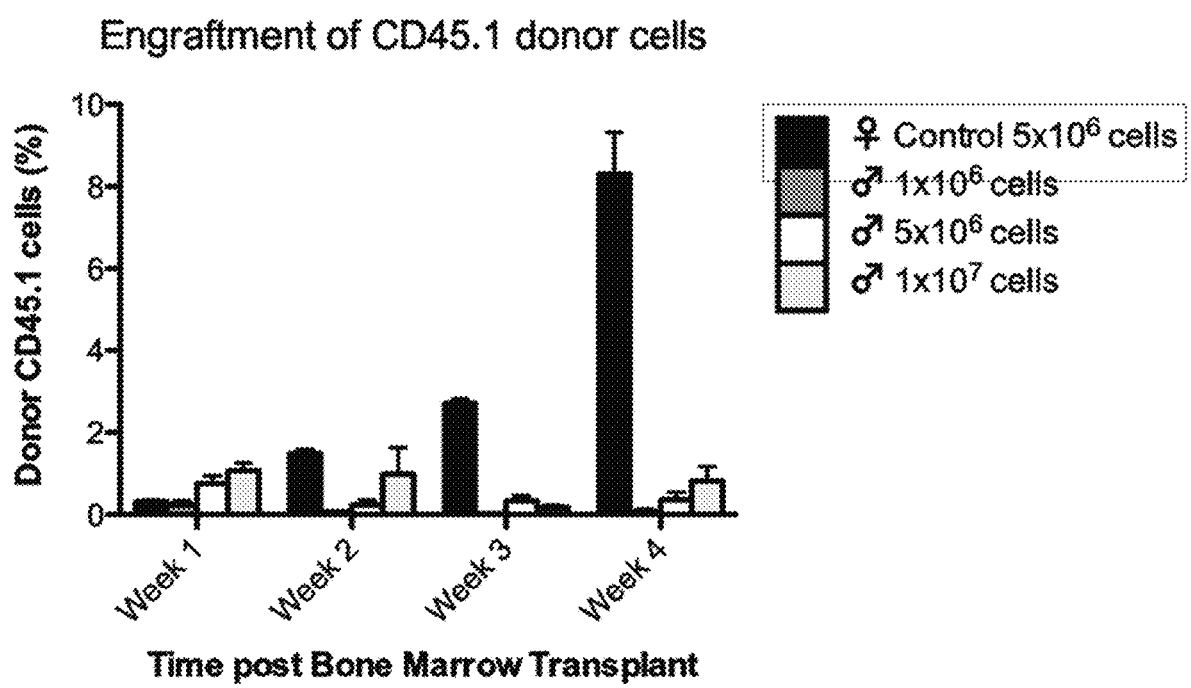
FIG. 26 shows the percent of CD45.1 donor cells observed in the recipient mice. Female CD45.2 mice were tolerized with either OVA-PLG or Dby-PLG on day −7. On day −1, the mice were irradiated with 200 rads and were then transplanted with 1×10$^6$, 5×10$^6$, or 1×10$^7$ bone marrow cells from male CD45.1 mice on day 0. The recipient mice were then tolerized with either OVA-PLG, Dby-SP, or Dby-PLG on day 1 and the blood harvested for FACS analysis of chimerism.

Female CD45.2 mice were tolerized with either OVA-PLG or the control peptide Dby-PLG (the major H-Y antigen expressed by Male C57BL/6 mice) on day −7. On day −1, the mice were irradiated with 200 rads and were then transplanted with $1\times10^6$, $5\times10^6$, or $1\times10^7$ bone marrow cells from male CD45.1 mice on day 0. The recipient mice were then tolerized with either OVA-PLG, Dby-SP, or Dby-PLG on day 1 and the blood harvested for FACS analysis of chimerism. FIG. 26 shows the percent of CD45.1 donor cells observed in the recipient mice.

Figure 27:
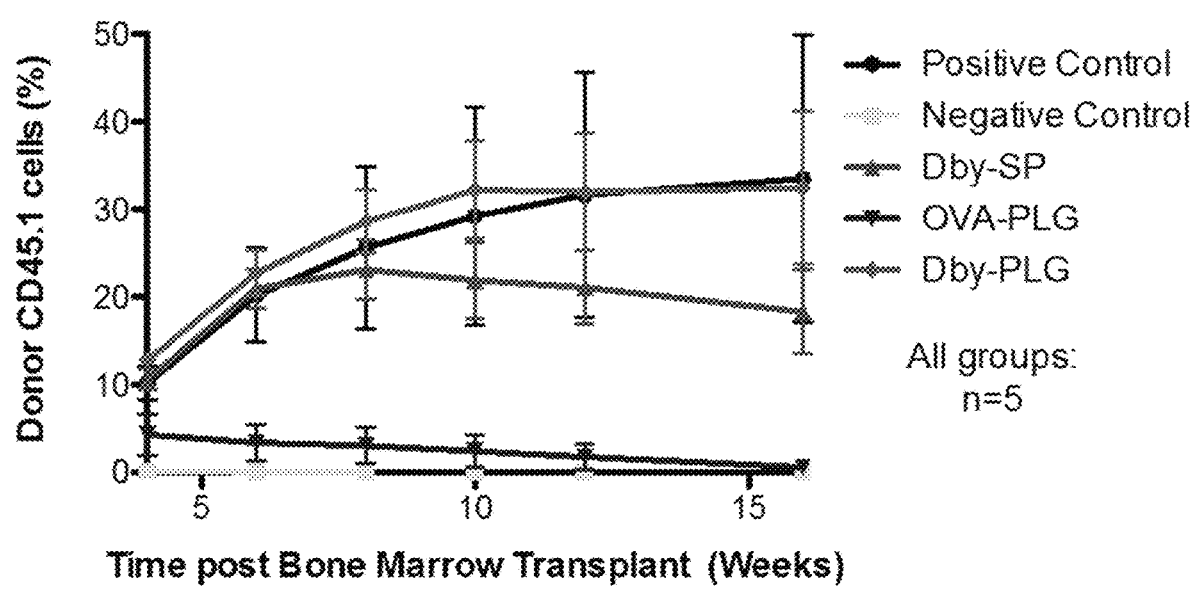
FIG. 27 shows the percent of donor CD45.1 cells in the recipient mice after tolerization with either OVA-PLG, Dby-SP, or Dby-PLG on day 1. One positive control mouse did not demonstrate significant engraftment (~10%). All negative control mice did not engraft donor cells. One Dby-SP mouse did not demonstrate significant engraftment (~10%). Two OVA-PLG mice engrafted donor cells (~10%): one completely rejected by Week 16. One Dby-PLG mouse started to reject at Week 12 and was at 10% by Week 16. The Dby-PLG group ranged from 10%-56% engraftment by Week 16. The OVA-PLG mice demonstrated: 1) Spontaneous engraftment, 2) Sequence homology between OVA$_{323}$ and Dby, or 3) tolerogenic properties of particles. Dby-PLG allows for more engraftment than Dby-SP and OVA-PLG.

FIG. 27 shows the percent of donor CD45.1 cells in the recipient mice after tolerization with either OVA-PLG, Dby-SP, or Dby-PLG on day 1. One positive control mouse did not demonstrate significant engraftment (~10%). All negative control mice did not engraft donor cells. One Dby-SP mouse did not demonstrate significant engraftment (~10%). Two OVA-PLG mice engrafted donor cells (~10%): one completely rejected by Week 16. One Dby-PLG mouse started to reject at Week 12 and was at 10% by Week 16. The Dby-PLG group ranged from 10%-56% engraftment by Week 16. The OVA-PLG mice demonstrated: 1) Spontaneous engraftment, 2) Sequence homology between $OVA_{323}$ and Dby, or 3) tolerogenic properties of particles. Dby-PLG allows for more engraftment than Dby-SP and OVA-PLG.

Figure 28:
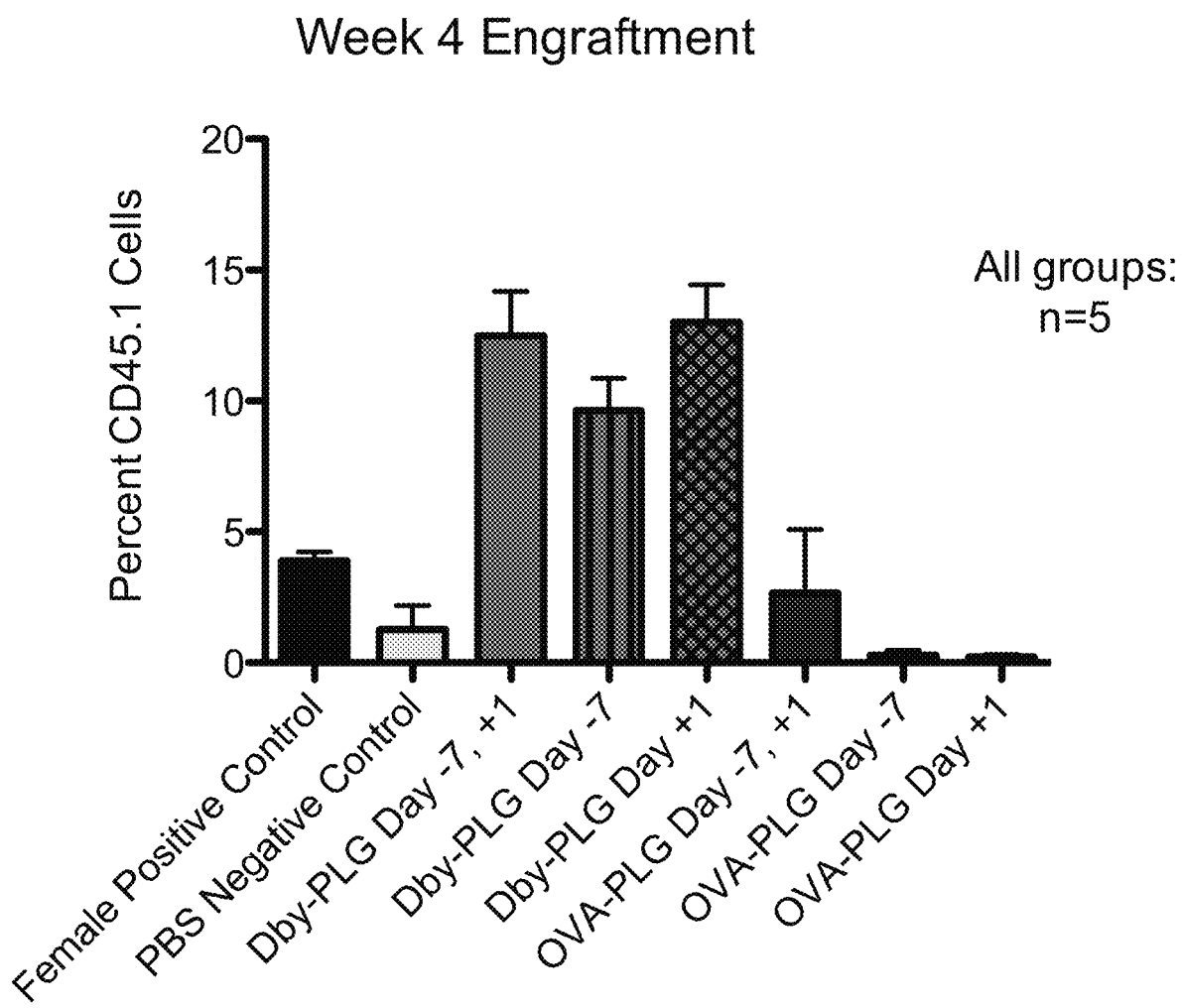
FIG. 28 shows that the timing tolerance has an effect on the percent of CD45.1 cells in the recipient mouse. Positive Controls show less engraftment (~4%) than expected (~10%). One Negative control mouse had 5% engraftment Out of all 3 OVA-PLG groups, one mouse in the Day −7, Day +1 group showed engraftment (12%). Tolerance on day 1 is more clinically relevant than tolerance on day −7.

FIG. 28 shows that the timing tolerance has an effect on the percent of CD45.1 cells in the recipient mouse. Positive Controls show less engraftment (~4%) than expected (~10%). One Negative control mouse had 5% engraftment Out of all 3 OVA-PLG groups, one mouse in the Day −7, Day +1 group showed engraftment (12%). Tolerance on day 1 is more clinically relevant than tolerance on day −7.

Example 17

Coumarin-6 PLGA Particles are not Detectable 24 Hours after Administration

Figure 29:
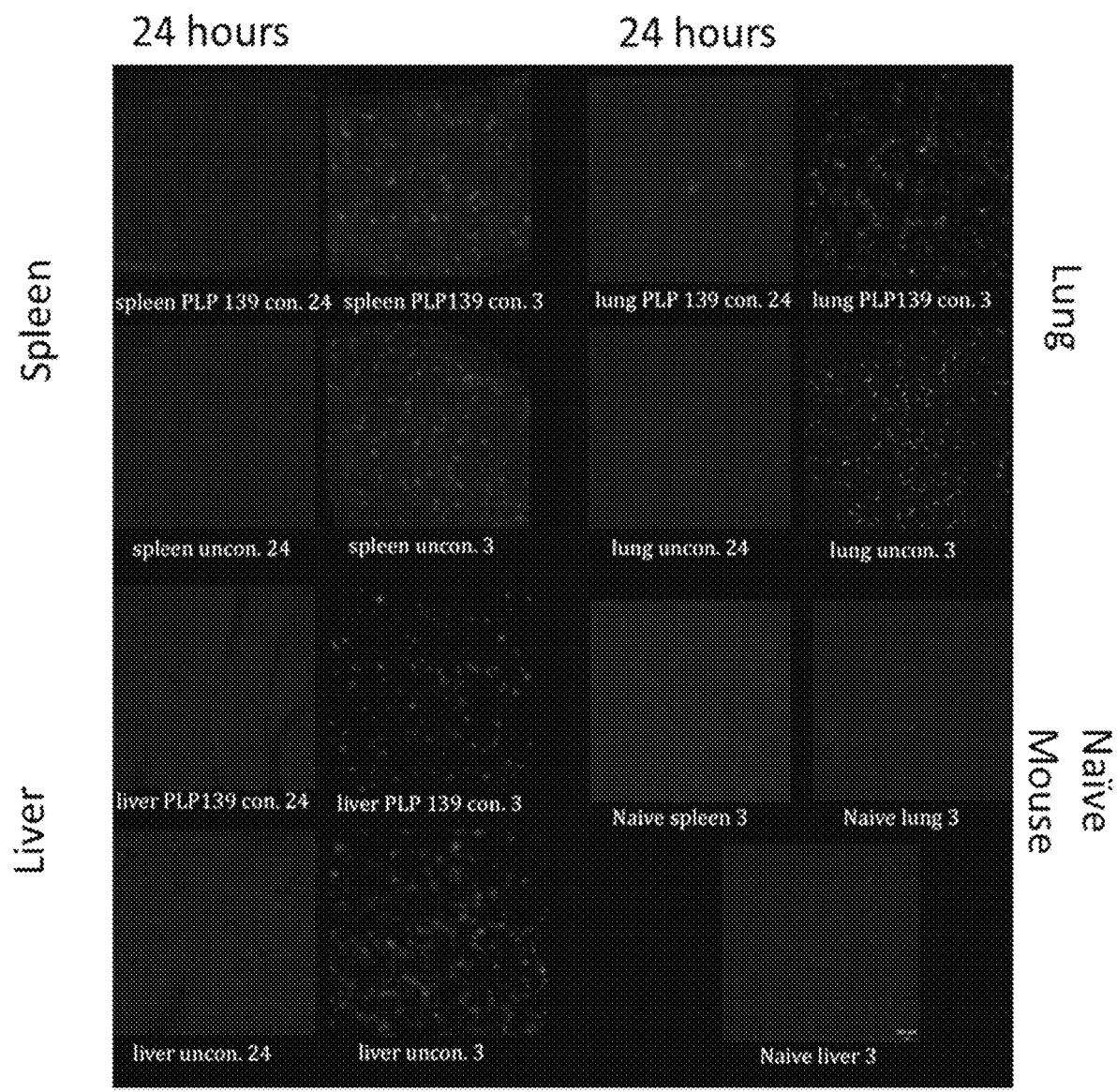
FIG. 29 shows that coumarin-6 PLGA particles, that were either coupled to an antigen or were antigen-free, were detectable at 3 hours post-administration, but not at 24 hours post-administration. The particles were detectable at 3 hours post-administration, but not at 24 hours post-administration. Naïve uninjected mouse (top row) as compared to i.v. fluorescent PLGA/PEMA microparticle injected mouse spleen (left column), liver (middle column) and lung (left column) sections at 3-hours post injection (middle row) and 24-hours (bottom row) post-injection, counterstained with DAPI.

Mice were treated with coumarin-6 PLGA particles that were either coupled to an antigen or antigen-free. As shown in FIG. 29, the particles were detectable at 3 hours post-administration, but not at 24 hours post-administration. Naïve uninjected mouse (top row) as compared to i.v. fluorescent PLGA/PEMA microparticle injected mouse spleen (left column), liver (middle column) and lung (left column) sections at 3-hours post injection (middle row) and 24-hours (bottom row) post-injection, counterstained with DAPI.

Example 18

Nanoparticles are Associated with Macrophages In Vivo

Figure 30:
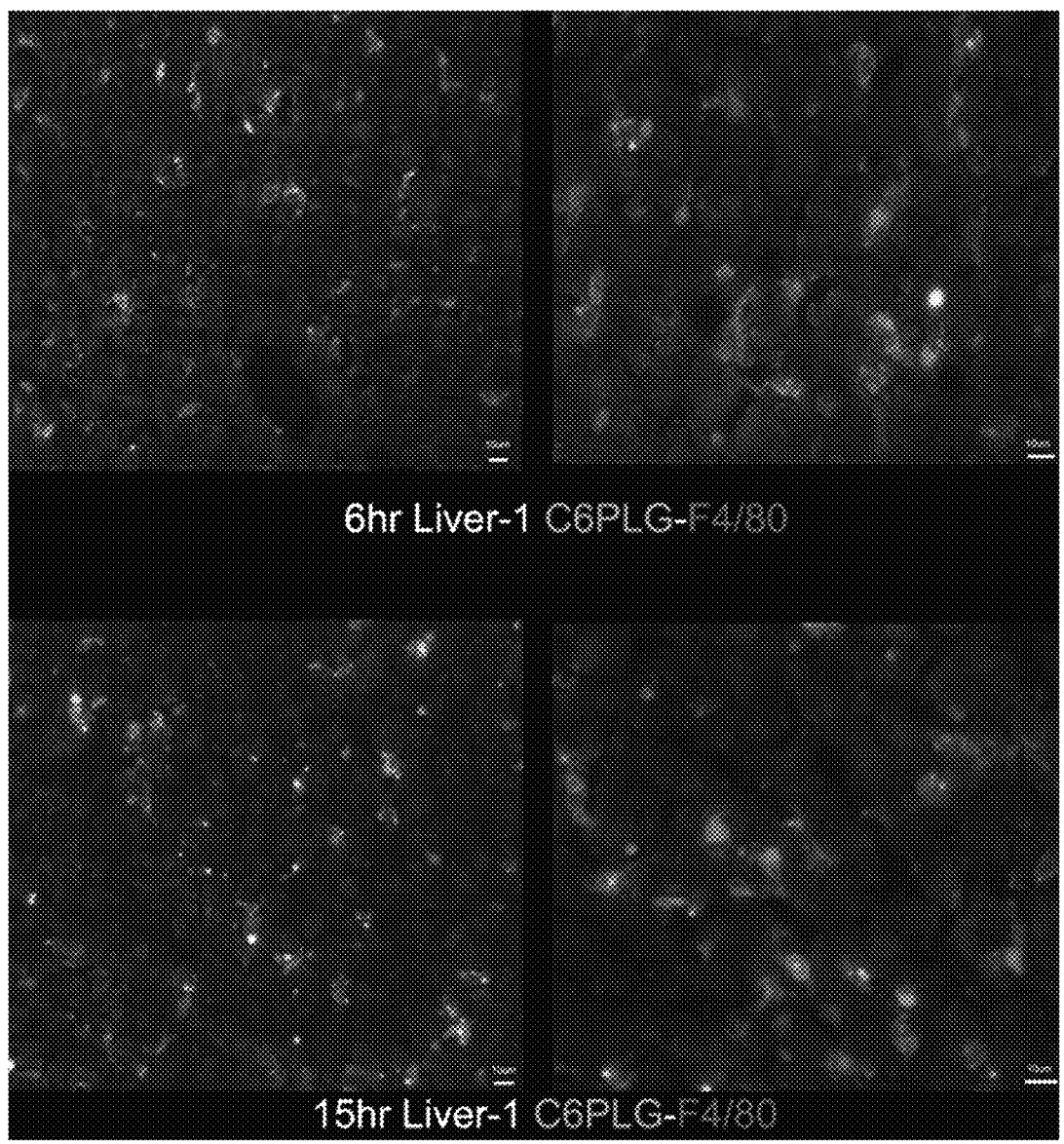
FIG. 30 shows that PLGA particles co-localized after 6 and 15 hours with F4/80+ cells in the liver.

Analysis of the liver 6 hours and 15 hours post-administration shows that PLGA particles co-localized with F4/80+ cells in the liver (FIG. 30).

Figure 31:
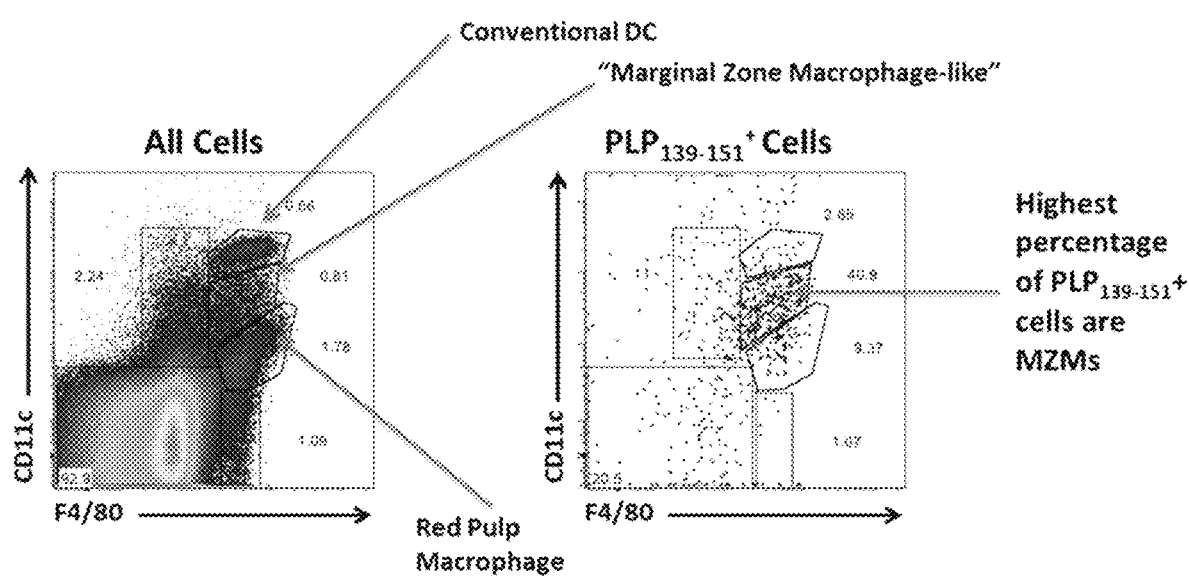
FIG. 31 shows that marginal zone macrophages predominantly uptake TAMRA-labeled $PLP_{139-151}$-coupled particles 24 hours after intravenous infusion. The highest percentage of $PLP_{139-151}$+ cells are marginal zone macrophages.

The marginal zone macrophages predominantly uptake TAMRA-labeled $PLP_{139-151}$-coupled particles 24 hours after intravenous infusion. As shown in FIG. 31, the highest percentage of $PLP_{139-151}$+ cells are marginal zone macrophages.

Example 19

Inhibition of R-EAE in SJL/J Mice Using Surface-Functionalized Poly(Lactide-Co-Glycolide) Particles Containing Soluble $PLP_{139-151}$ within their Cores Groups of SJL/J mice were injected IV with 2.5 mg 500 nm-700 nm surface-functionalized poly(lactide-co-glycolide) particles with soluble PLP139-151 peptide within their cores on Day −7 and Day −1 before relative to priming with PLP139-151/CFA on Day 0. Control mice were primed on Day 0 but did not receive particle treatment on Day −7 or Day −1. Mice were observed for clinical signs of R-EAE for an additional 20 days.

Figure 32:
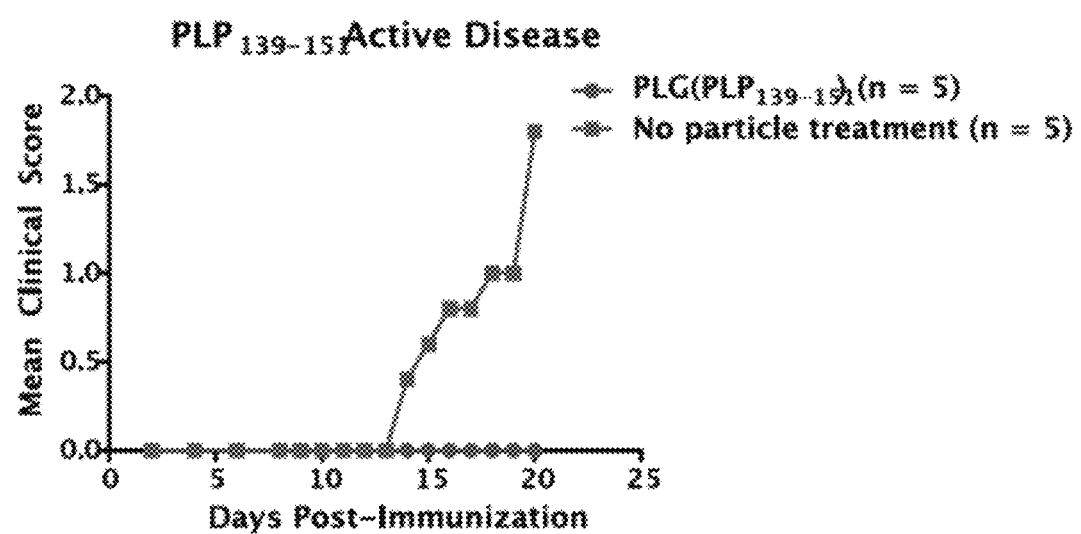
FIG. 32 depicts the daily mean clinical score against the number of days $PLP_{139}$-151/CFA priming. $PLP_{139-151}$/CFA-induced R-EAE is inhibited in SJL/J mice by the induction of immunological tolerance using surface-functionalized poly(lactide-co-glycolide) particles containing soluble $PLP_{139-151}$ within their cores.

The results depicted in FIG. 32 depict the daily mean clinical score against the number of days PLP139-151/CFA priming. PLP139-151/CFA-induced R-EAE is inhibited in SJL/J mice by the induction of immunological tolerance using surface-functionalized poly(lactide-co-glycolide) particles containing soluble PLP139-151 within their cores.

Example 20

Inhibition of Allergic Airway Inflammation by Surface-Functionalized Poly(Lactide-Co-Glycolide) Particles Containing Soluble Ovalbumin Allergic airway inflammation (AIA) was induced in mice. Groups of Balb/c mice were injected intravenously with 2.5 mg 500 nm-700 nm surface-functionalized poly(lactide-co-glycolide) particles with soluble ovalbumin or soluble bovine serum albumin (control) within their cores on Day −7 and Day +7 before priming with ovalbumin/alum on Days 0 and +14. Mice were challenged on Days +28-30 with aerosolized ovalbumin. Mice were then sacrificed and bronchoalveolar lavage fluid obtained. The serum levels of ovalbumin specific IgE were measured also.

Eosinophil counts within the bronchoalveolar lavage fluid indicate the severity of AAI—higher counts indicated worse disease. Serum levels of IgE indicate the severity of AAI—higher levels indicated worse disease.

Figure 33:
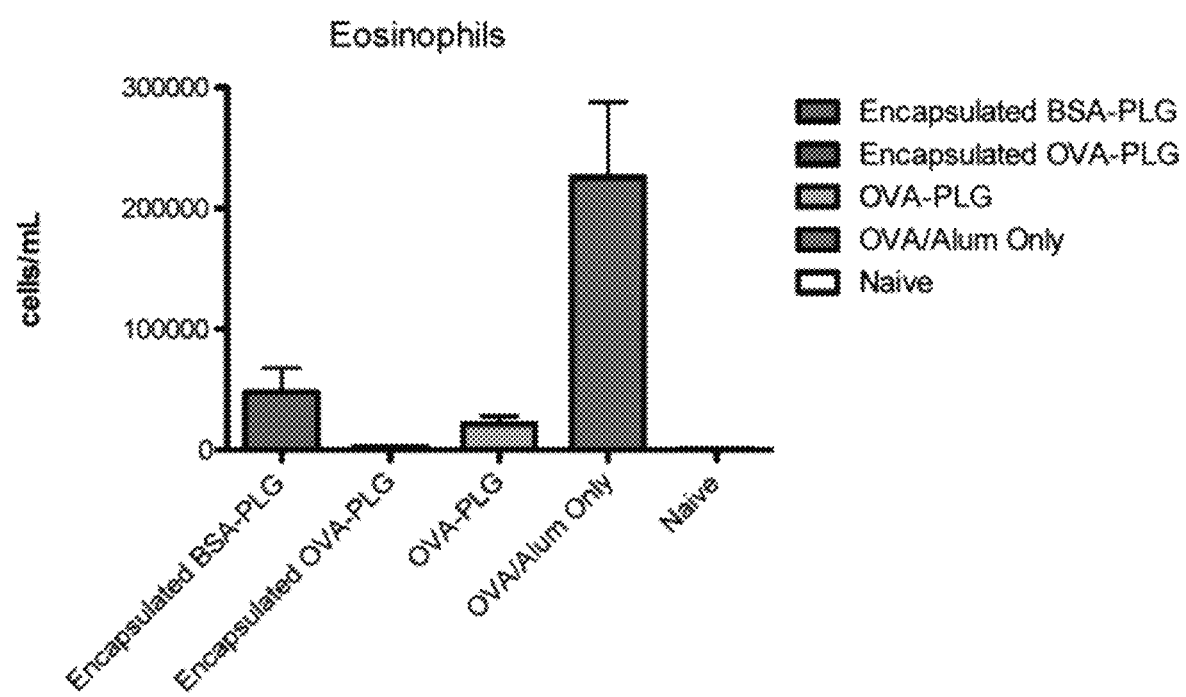
FIG. 33 shows that mice treated with encapsulated OVA-PLG showed the greatest reduction in eosinophil accumulation.
Figure 34:
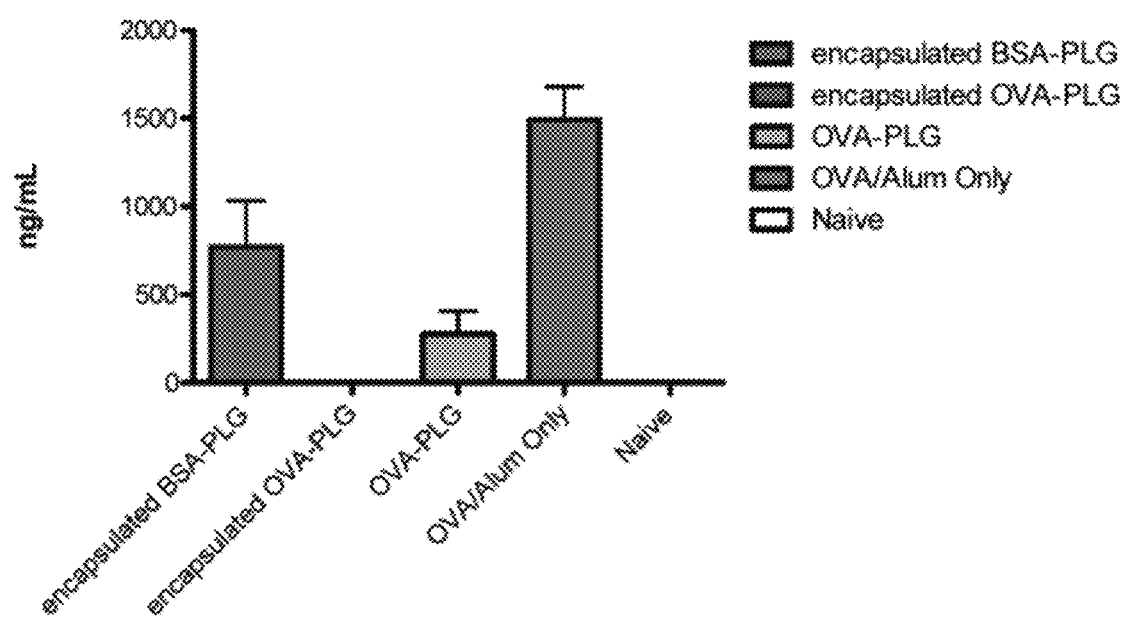
FIG. 34 shows that mice treated with encapsulated OVA-PLG showed the greatest reduction in serum IgE levels compared to untreated or control treated animals.

FIG. 33 shows that mice treated with encapsulated OVA-PLG showed the greatest reduction in eosinophil accumulation. FIG. 34 shows that mice treated with encapsulated OVA-PLG showed the greatest reduction in serum IgE levels compared to untreated or control treated animals.

Ovalbumin/alum-induced allergic airway inflammation in Balb/c mice was inhibited by the induction of immunological tolerance using surface-functionalized poly(lactide-co-glycolide) particles containing soluble ovalbumin within their cores.

Example 21

Synthesis of Surface-Functionalized Poly(Lactide-Co-Glycolide) Particles Encapsulating Antigen The present Example details the formulation and partial characterization of biodegradable poly(lactide-co-glycolide) particles that have been surface-functionalized with a high density of carboxylate groups and contain soluble antigen within their cores that are surrounded by a shell of poly (lactide-co-glycolide) for tolerance induction in autoimmune disease and for the treatment of allergies.

The high density of carboxylate groups was achieved by the use of poly(ethylene-alt-maleic anhydride (PEMA)), a polymer with carboxylate groups incorporated into its backbone, as the surfactant for the emulsification process.

As described above, biodegradable poly(lactide-co-glycolide) particles containing soluble PLP139-151 within their cores and surface-functionalized with a high density of carboxylate groups are effective for the induction of immunological tolerance in the SJL/J PLP139-151/CFA-induced R-EAE murine model of multiple sclerosis. Furthermore, biodegradable poly(lactide-co-glycolide) particles containing soluble ovalbumin within their cores and surface-functionalized with a high density of carboxylate groups are effective for the induction of immunological tolerance in the Balb/c ovalbumin/alum-induced AAI murine model of allergic asthma.

Poly(lactide-co-glycolide) particles containing soluble ovalbumin or bovine serum albumin within their cores and surface-functionalized with a high density of carboxylate groups were synthesized using a double emulsion-solvent evaporation method as follows:

1. 150 µL of 200 mg/mL ovalbumin or bovine serum albumin in endotoxin-free water was added dropwise to 2 mL of 20% w/v poly(lactide-co-glycolide) in dichloromethane in a 20 mL scintillation vial.

2. The resultant mixture was placed on ice and sonicated for 30 seconds at 10 watts using a probe sonicator.

3. 10 mL of 1% w/v poly(ethylene-alt-maleic anhydride) in water was added.

4. The resultant mixture was placed on ice and sonicated for 30 seconds at 16 watts using a probe sonicator.

5. The resultant emulsion was poured into 200 mL 0.5% w/v poly(ethylene-alt-maleic anhydride) in a 600 mL beaker and stirred overnight to allow for particle hardening.

6. The hardened particles were then purified by centrifugation and washed 3 times with bicarbonate buffer pH 9.6.

7. The purified particles were resuspended in 4% w/v sucrose and 3% w/v D-mannitol in water, flash-frozen in liquid nitrogen and lyophilized to dryness.

Figure 35:
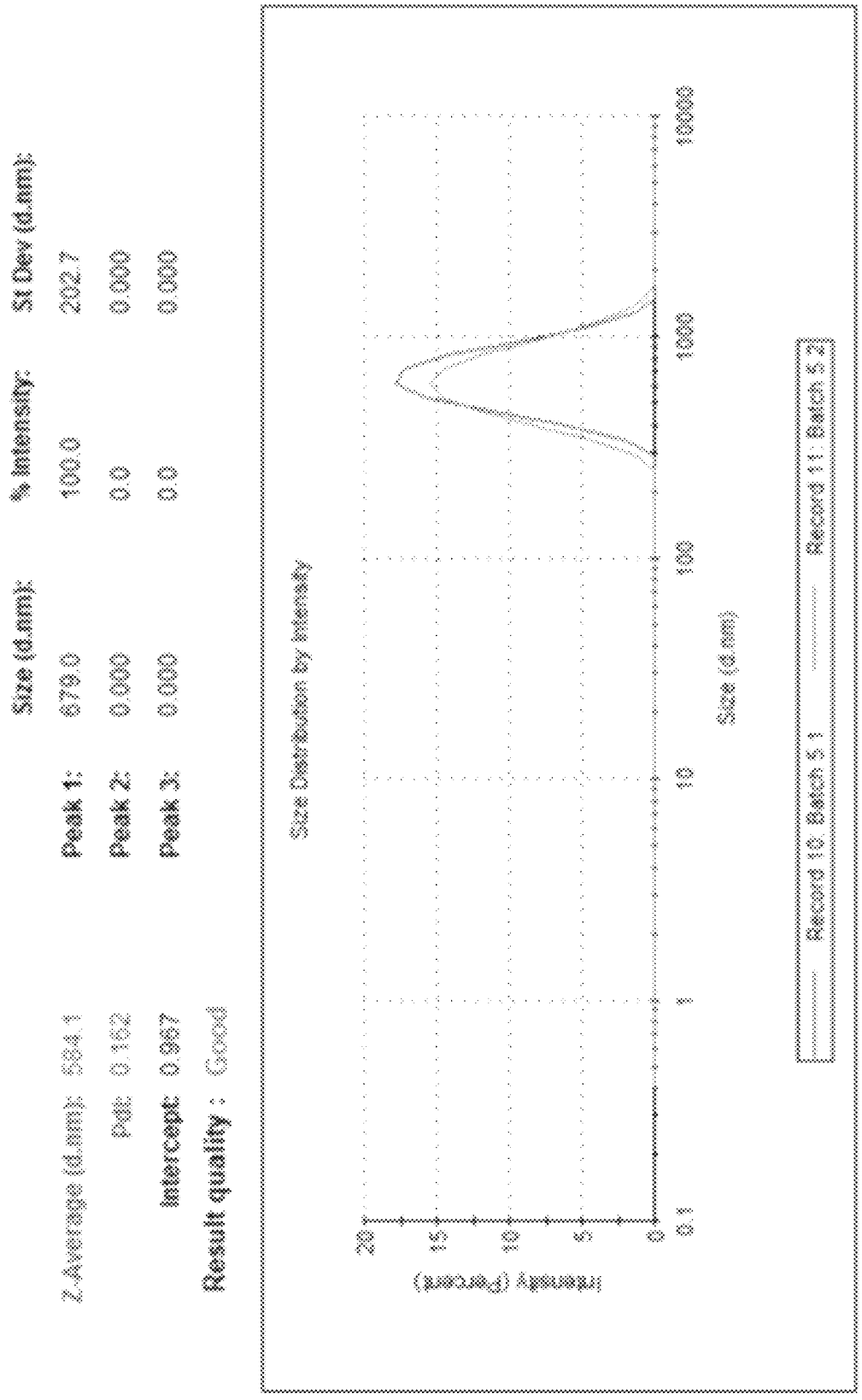
FIG. 35 shows the characterization of surface-functionalized poly(lactide-co-glycolide) particles containing soluble $PLP_{139-151}$ within their cores by dynamic light scattering analysis. Surface-functionalized poly(lactide-co-glycolide) particles were analyzed on a Malvern Zetasizer Nano ZS (Malvern Instruments, Westborough, Mass.) at a count rate of $1.792 \times 10^5$ counts per second in 18.2 MΩ water. The population of surface-functionalized poly(lactide-co-glycolide) particles had a Z-average diameter of 584 nm, a peak diameter of 679 nm and a polydispersity index of 0.162. These results are representative of 6 batches of syntheses, following the protocol written above.

FIG. 35 shows the characterization of surface-functionalized poly(lactide-co-glycolide) particles containing soluble PLP139-151 within their cores by dynamic light scattering analysis. Surface-functionalized poly(lactide-co-glycolide) particles were analyzed on a Malvern Zetasizer Nano ZS (Malvern Instruments, Westborough, Mass.) at a count rate of 1.792×105 counts per second in 18.2 MΩ water. The population of surface-functionalized poly(lactide-co-glycolide) particles had a Z-average diameter of 584 nm, a peak diameter of 679 nm and a polydispersity index of 0.162. These results are representative of 6 batches of syntheses, following the protocol written above.

Figure 36:
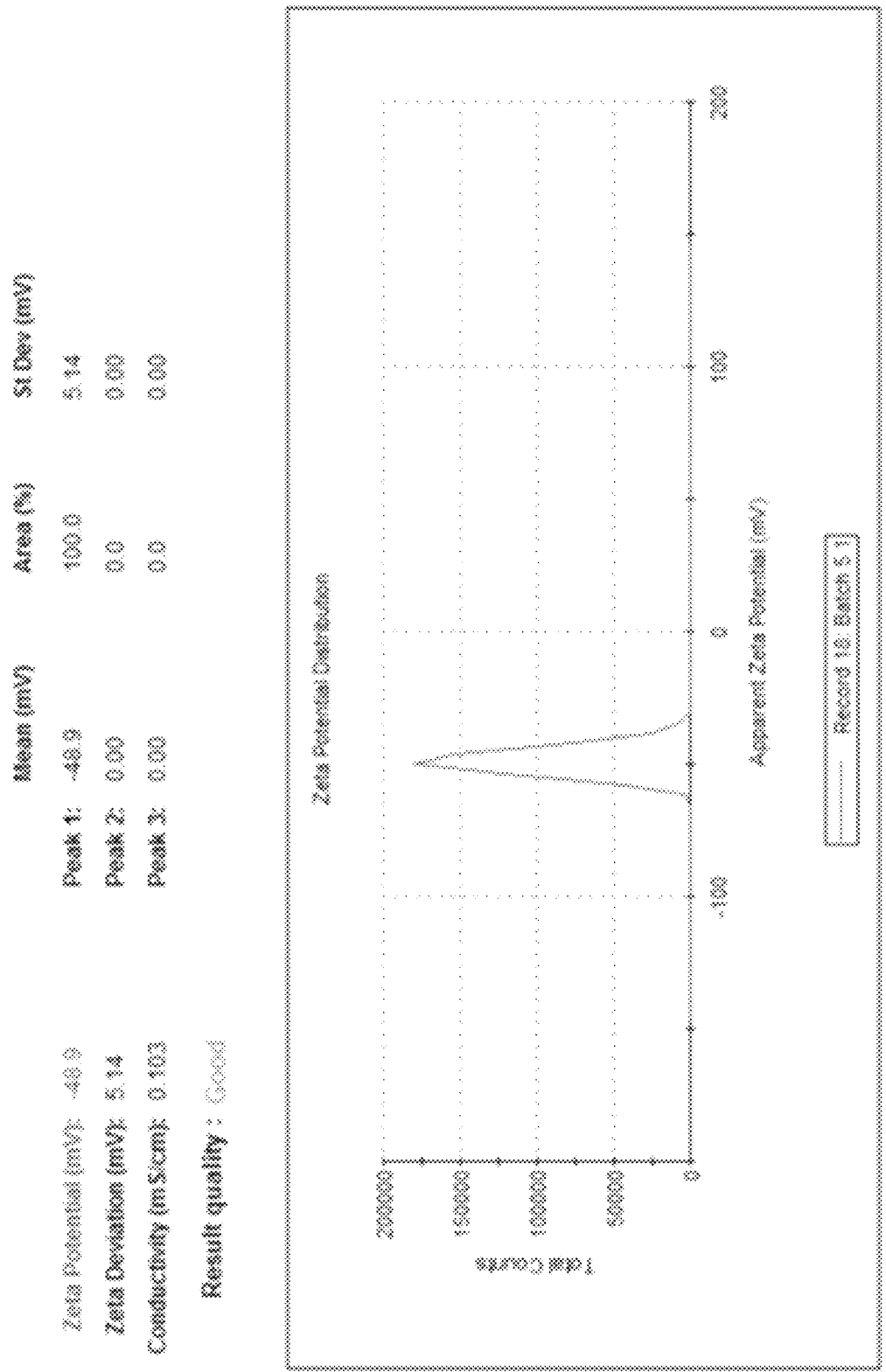
FIG. 36 shows the characterization of surface-functionalized poly(lactide-co-glycolide) particles containing soluble $PLP_{139-151}$ within their cores by ζ-potential measurement. Surface functionalized poly(lactide-co-glycolide) particles were analyzed on a Malvern Zetasizer Nano ZS (Malvern Instruments, Westborough, Mass.) at a count rate of $6.67 \times 10^4$ counts per second in 18.2 MΩ water. The population of surface-functionalized poly(lactide-co-glycolide) particles had a peak ζ-potential of −48.9 mV and a ζ deviation of 5.14 mV. These results are representative of 6 batches of syntheses, following the protocol written above.

FIG. 36 shows the characterization of surface-functionalized poly(lactide-co-glycolide) particles containing soluble PLP139-151 within their cores by ζ-potential measurement. Surface functionalized poly(lactide-co-glycolide) particles were analyzed on a Malvern Zetasizer Nano ZS (Malvern Instruments, Westborough, Mass.) at a count rate of 6.67×104 counts per second in 18.2 MΩ water. The population of surface-functionalized poly(lactide-co-glycolide) particles had a peak ζ-potential of −48.9 mV and a ζ deviation of 5.14 mV. These results are representative of 6 batches of syntheses, following the protocol written above.

Figure 37:
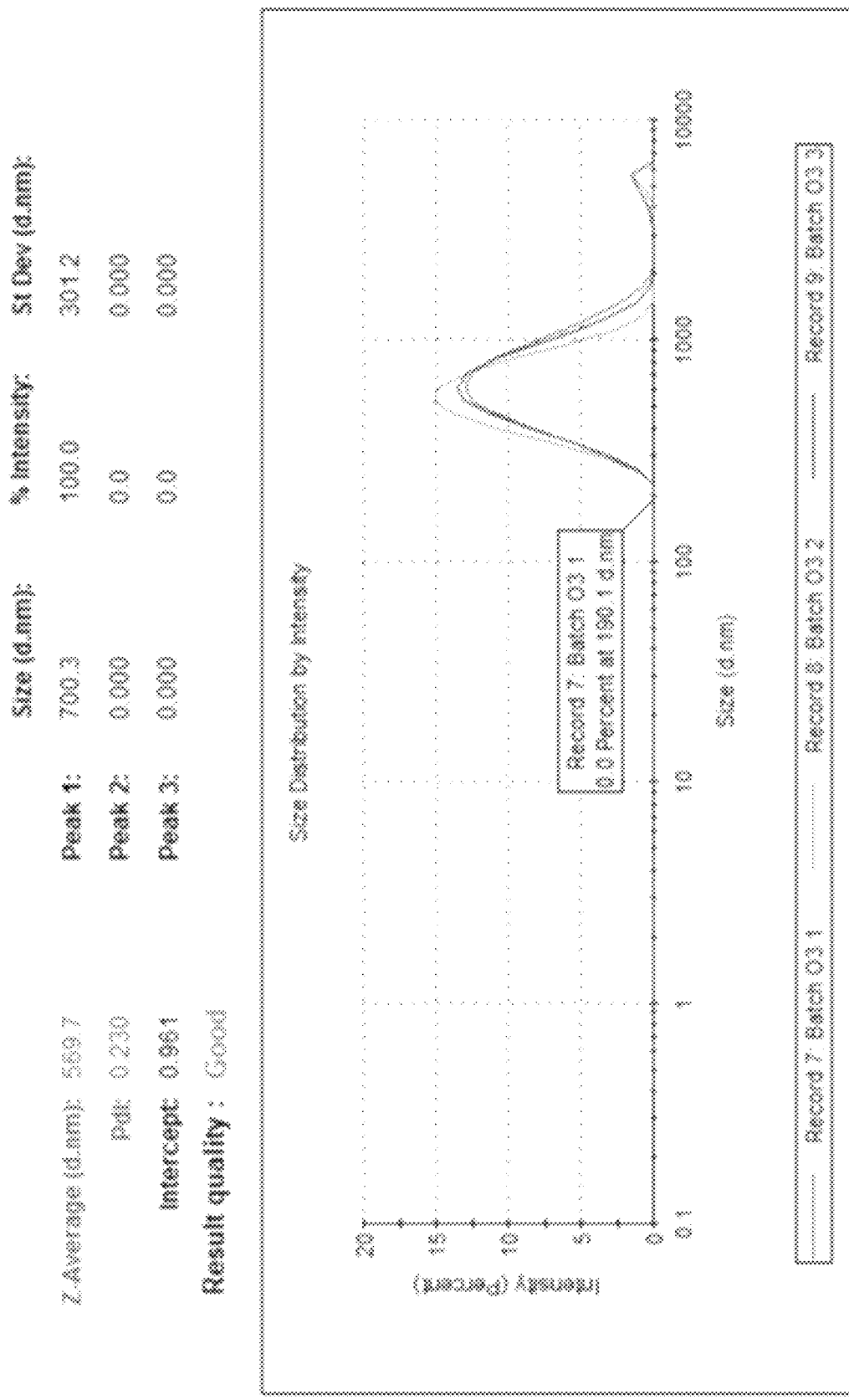
FIG. 37 shows the characterization of surface-functionalized poly(lactide-co-glycolide) particles containing soluble ovalbumin within their cores by dynamic light scattering analysis. Surface-functionalized poly(lactide-co-glycolide) particles were analyzed on a Malvern Zetasizer Nano ZS (Malvern Instruments, Westborough, Mass.) at a count rate of $1.822 \times 10^5$ counts per second in 18.2 MΩ water. The population of surface-functionalized poly(lactide-co-glycolide) particles had a Z-average diameter of 569.7 nm, a peak diameter of 700.3 nm and a polydispersity index of 0.230. These results are representative of 3 batches of syntheses, following the protocol written above.

FIG. 37 shows the characterization of surface-functionalized poly(lactide-co-glycolide) particles containing soluble ovalbumin within their cores by dynamic light scattering analysis. Surface-functionalized poly(lactide-co-glycolide) particles were analyzed on a Malvern Zetasizer Nano ZS (Malvern Instruments, Westborough, Mass.) at a count rate of 1.822×105 counts per second in 18.2 MΩ water. The population of surface-functionalized poly(lactide-co-glycolide) particles had a Z-average diameter of 569.7 nm, a peak diameter of 700.3 nm and a polydispersity index of 0.230. These results are representative of 3 batches of syntheses, following the protocol written above.

Figure 38:
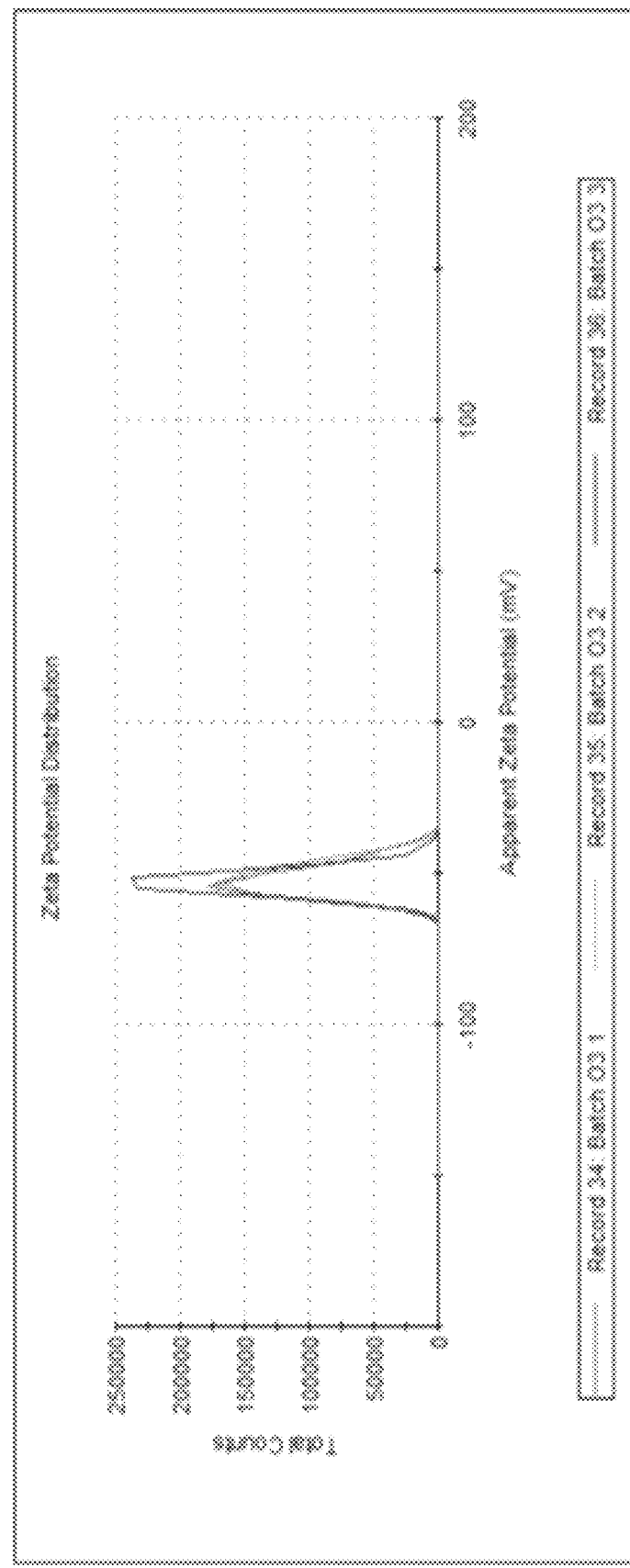
FIG. 38 shows characterization of surface-functionalized poly(lactide-co-glycolide) particles containing soluble ovalbumin within their cores by ζ-potential measurement. Surface functionalized poly(lactide-co-glycolide) particles were analyzed on a Malvern Zetasizer Nano ZS (Malvern Instruments, Westborough, Mass.) at a count rate of $2.67 \times 10^4$ counts per second in 18.2 MΩ water. The population of surface-functionalized poly(lactide-co-glycolide) particles had a peak ζ-potential of −52.2 mV and a ζ deviation of 5.38 mV. These results are representative of 3 batches of syntheses, following the protocol written above.

FIG. 38 shows Characterization of surface-functionalized poly(lactide-co-glycolide) particles containing soluble ovalbumin within their cores by ζ-potential measurement. Surface functionalized poly(lactide-co-glycolide) particles were analyzed on a Malvern Zetasizer Nano ZS (Malvern Instruments, Westborough, Mass.) at a count rate of 2.67×104 counts per second in 18.2 MΩ water. The population of surface-functionalized poly(lactide-co-glycolide) particles had a peak ζ-potential of −52.2 mV and a ζ deviation of 5.38 mV. These results are representative of 3 batches of syntheses, following the protocol written above.

Example 22

Surface-Functionalized Liposomes Containing Soluble $PLP_{139-151}$ within their Cores Induce Immunological Tolerance in the Murine R-EAE Model of Multiple Sclerosis The present inventors have also discovered that biodegradable liposomal delivery vehicles that have been surface-functionalized with a high density of negatively-charged groups and contain soluble antigen within their cores induce immunological tolerance in the R-EAE murine model of multiple sclerosis.

The liposomes used in this study were composed of the following lipids at the following molar ratios—30:30:40 phosphatidylcholine:phosphatidylglycerol:cholesterol. Groups of SJL/J mice were injected IV with 200 nm surface-functionalized liposomes (10 μmol total lipid per mouse) with soluble $PLP_{139-151}$ peptide within their cores on Day −7 relative to priming with $PLP_{139-151}$/CFA on Day 0. Control mice were primed on Day 0 and received 500 nm-700 nm surface-functionalized liposomes (10 μmol total lipid per mouse) with soluble $OVA_{323-339}$ peptide within their cores on Day −7. Mice were observed for clinical signs of R-EAE for an additional 17 days.

Figure 39:
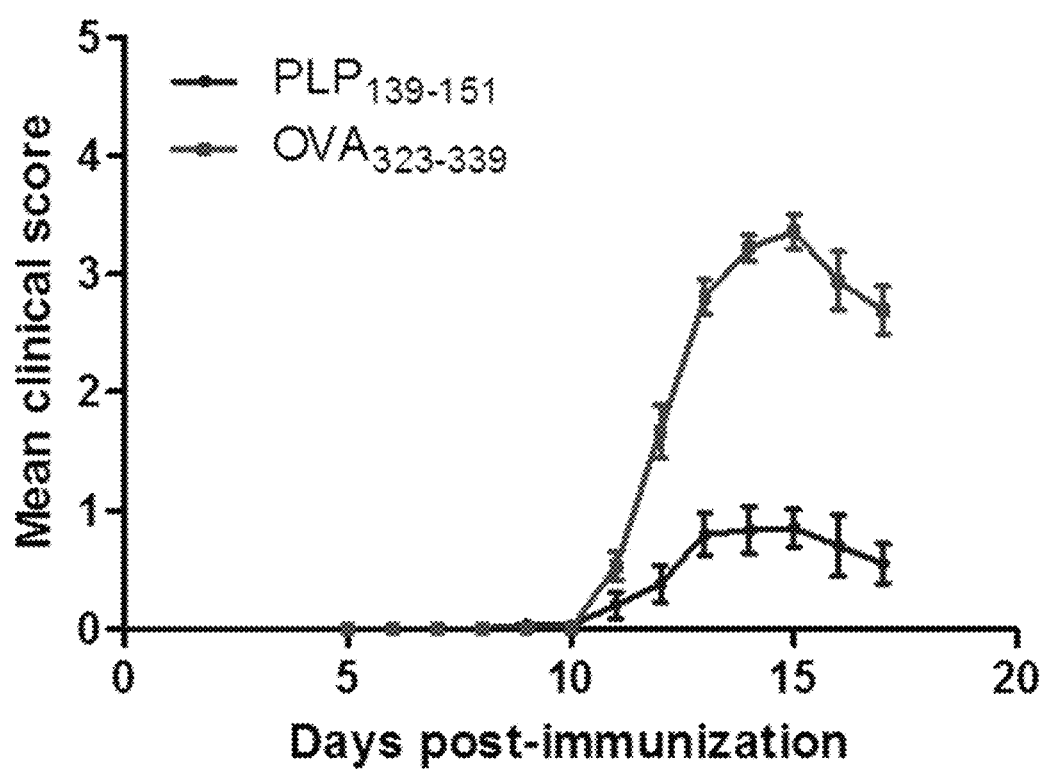
FIG. 39 shows a graph demonstrating that surface-functionalized liposomes containing soluble $PLP_{139-151}$ peptide within their cores induce immunological tolerance in the murine model of multiple sclerosis. Animals were treated with either surface-functionalized liposomes containing soluble $PLP_{139-151}$ peptide within their cores (circles) or surface-functionalized liposomes containing soluble $OVA_{323-339}$ peptide (squares). The mean clinical scores of those animals receiving the $PLP_{139-151}$ peptide liposomes was lower than that of animals receiving the $OVA_{323-339}$ peptide liposomes.

The results depict the daily mean clinical score against the number of days $PLP_{139-151}$/CFA priming. As shown in FIG. 39, the animals treated with the surface-functionalized liposomes with soluble $PLP_{139-151}$ peptide within their cores had a lower clinical score than those animals treated with the surface-functionalized liposomes containing soluble $OVA_{323-339}$ peptide.

The results of this study demonstrate that biodegradable liposomes containing soluble $PLP_{139-151}$ within their cores and surface-functionalized with high density of negatively-charged groups are effective for the induction of immunological tolerance in the SJL/J $PLP_{139-151}$/CFA-induced R-EAE murine model of multiple sclerosis.

The tolerance induced by antigen-coupled or antigen-encapsulated particles is antigen-specific, dose dependent and long-lasting (>150 days). Tolerance is best induced by intravenous administration of a coupled particle that is between 500 nm and 1 μm in diameter with a zeta potential ≤−5-mV. The induction of tolerance is dependent on the uptake of the particles by the MARCO scavenger receptor with sees polyanionic surfaces (e.g. carboxylated PS/PLG particles). The tolerance is induced and maintained by a combination of anergy (partially reversed by anti-PD-1 and agonistic anti-CD40 antibodies) and iTregs (partially reversed by anti-CD25 antibodies). The particles of the invention accumulate predominantly in the liver and splenic marginal zone macrophages ($CD11b^{hi}$ $CD11c^{lo}$ $MARCO^+$ $Sign-R1^+$ $Siglec-1^-$).

There are numerous advantages of using antigen-coupled particles for the treatment of autoimmune diseases compared with using antigen-pulsed or antigen-directed immature tolerogenic dendritic cells or engineering antigen-specific Tregs. The rapidity and simplicity of tolerogen preparation and induction using a GMP manufacturable, off-the-shelf universal tolerogenic carrier; there is no need to isolate and expand immature dendritic cells or Tregs ex vivo; there is no need to be concerned with immature dendritic cells being activated upon ex vivo manipulation and becoming stimulatory rather than tolerogenic or of Tregs converting to Th1/17 after transfer; since the hose immature marginal zone APCs process and represent the antigen in a tolerogenic manner, host APCs can select the relevant immunodominant self epitopes from PLG particles encapsulating intact autoantigens or tissue extracts (e.g. OVA encapsulated PLG particles prevent OVA/Alum-induced AAD); and the protocol is antigen-specific with no bystander suppression, is safe, highly efficient, and can induce unresponsiveness in both effector T cells (Th1, Th2, Th17, and CD8) and naïve T cells involved with epitope spreading.

Synthetic, biodegradable particles and liposomes could lead to ease of manufacturing, broad availability of therapeutic agents, and increase the number of potential treatment sites. To this end, we have specifically engineered surface-functionalized biodegradable poly(lactideco-glycolide) particles with a high density of surface carboxylate groups, using the surfactant poly(ethylene-alt-maleic anhydride).

We have also developed surface-functionalized liposomes using a 30:30:40 ratio of phosphatidylcholine:phosphatidylglycerol:cholesterol.

We have further engineered these particles to contain soluble ovalbumin within their cores so as to circumvent chemical contamination and purity issues surrounding surface-conjugation of peptide or protein. These surface-functionalized poly(lactide-co-glycolide) particles containing soluble ovalbumin within their cores are effective for the prevention of disease development and hence the induction of immunological tolerance in the Balb/c ovalbumin/alum-induced AAI murine model of allergic asthma. Peptide or protein conjugated to carboxylate-functionalized poly(lactide-co-glycolide) particles using EDC are attached in an indiscriminate fashion, resulting in antigen aggregates and particle-antigen-particle aggregates that are difficult to characterize and purify into homogeneous populations.

We have produced a homogeneous population of surface functionalized poly(lactide co-glycolide) particles containing soluble ovalbumin within their cores that do not require surface conjugation of antigen.

We have further demonstrated that biodegradable liposomes containing soluble $PLP_{139-151}$ within their cores and surface-functionalized with high density of negatively-charged groups are effective for the induction of immunological tolerance in the SJL/J $PLP_{139-151}$/CFA-induced R-EAE murine model of multiple sclerosis.

The liposomes and poly(lactide-co-glycolide) particles of the present invention offer numerous advantages. The advantages include:
1) Biodegradable particles will not persist for long times in the body, and the time for complete degradation can be controlled.
2) Particles and liposomes can be functionalized to facilitate internalization without cell activation. Toward this goal, we have loaded phosphatidylserine into PLG microspheres.
3) Particles and liposomes can also be designed to incorporate targeting ligands for a specific cell population.
4) Anti-inflammatory cytokines such as IL-10 and TGF-β, can also be included to limit activation of the cell type that is internalizing the particles and to facilitate the induction of tolerance via anergy and/or deletion and the activation of regulatory T cells.

This combinatorial function of the particle or liposome can target tolerance induction from multiple perspectives, thus designer particles are a significant advance relative to the polystyrene particles. Potential clinical applications of this tolerance inducing technology include:
(1) T cell- and antibody-mediated autoimmune diseases (such as multiple sclerosis, type 1 diabetes, rheumatoid arthritis, systemic lupus, etc.)—tolerance would be induced with particles complexed with the relevant autoantigens driving the particular autoimmune disease
(2) food and lung allergies, skin allergies, and asthma—tolerance would be induced with particles complexed with the specific foods (e.g. peanut proteins, etc.), injected (bee venom proteins, etc.), or inhaled substances (e.g., ragweed pollen proteins, pet dander proteins, etc.) which elicit the allergic reaction
(3) transplant rejection—tolerance would be induced to the transplant antigens on donor organs or cells prior to organ transplant to prevent rejection by the recipient
(4) enzyme replacement therapy—tolerance would be induced to enzymes which patients with genetic deficiencies fail to produce, to prevent them from making neutralizing antibody responses to recombinantly-produced enzymes administered to treat their particular deficiency.

Example 23

Figure 40A:
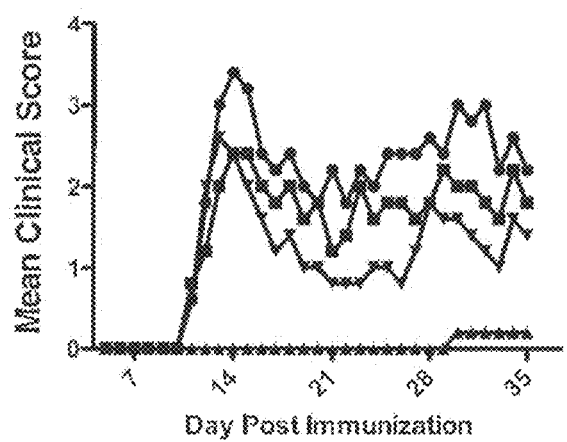
FIGS. 40A-40B show that the charge of the particle administered has an effect on the development of EAE in the mouse model.
Figure 40B:
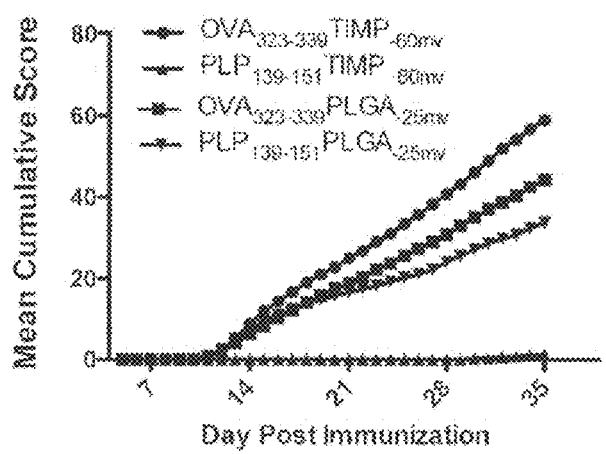

The Particles Most Effective at Inducing Tolerance are Negatively Charged and an Average Diameter of 500 nm The key particle parameters for inducing tolerance are the size and charge of the composition. As shown in FIGS. 40A and B, the charge of the particle affects the efficacy of tolerance induction. A comparison of EAE mice treated with OVA conjugated particles with a −25 mv or −60 mv charge found that compositions comprising particles with a charge of −60 mv induce tolerance more effectively than those with a −25 mV charge. Mice were treated with TIMP (tolerogenic immune modifying particles) having a charge of either −60 mv or −25 mv. Mice were treated with either $OVA_{323-339}$-$TIMP_{-60mv}$, $OVA_{323-339}$-$PLGA_{-25mv}$, $PLP_{139-151}$-$TIMP_{-60mv}$, or $PLP_{139-151}$-$PLGA_{-25mv}$ (all antigens are encapsulated) and scored for clinical disease. Panel (A) shows the mean clinical score and Panel (B) shows the mean cumulative score of the EAE animals.

Figure 41A:
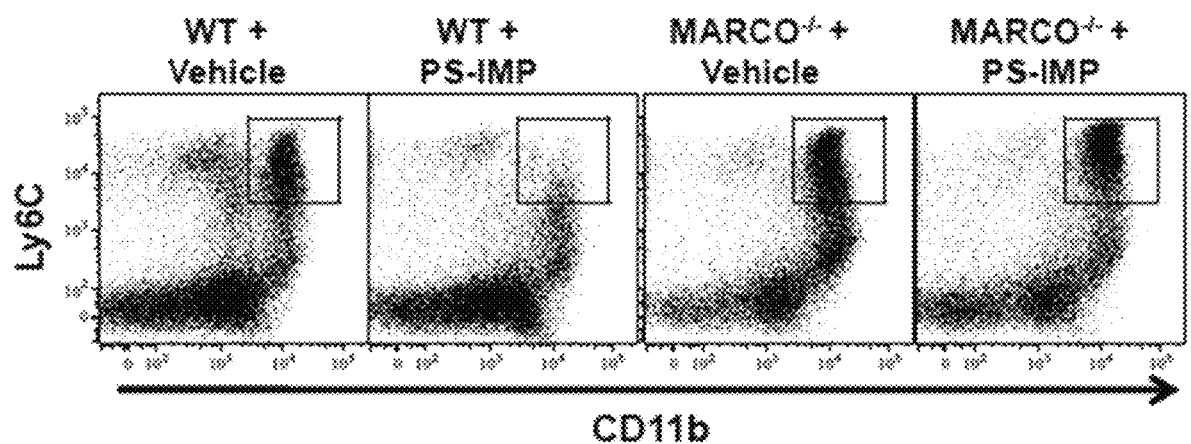
FIGS. 41A-41B show that the charge of the immune-modifying particle is important for targeting the immune modifying particle to the antigen presenting cell. Wild type or MARCO−/+animals were treated with either PS-IMP or vehicle. The results indicate that particles with a reduced negative charge have a lower efficacy because there is less interaction with the scavenger receptor MARCO (FIG. 41A). AntiMARCO antibody alone is not capable of providing similar efficacy at PLGA IMP (FIG. 41B).
Figure 41B:
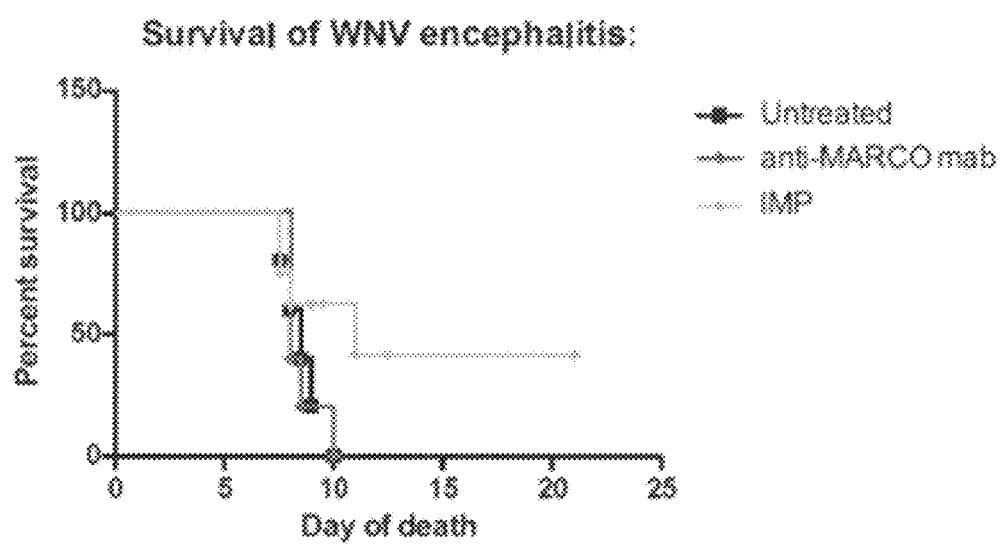

The negative charge on the particle affects the ability of the particle to interaction with the MARCO scavenger receptor. FIG. 41 shows that the charge of the immune-modifying particle is important for targeting the immune modifying particle to the antigen presenting cell. Wild type or MARCO−/+animals were treated with either PS-IMP or vehicle. The results indicate that particles with a reduced negative charge have a lower efficacy because there is less interaction with the scavenger receptors such as MARCO that have positively charged collagen-like domains.

Figure 42A:
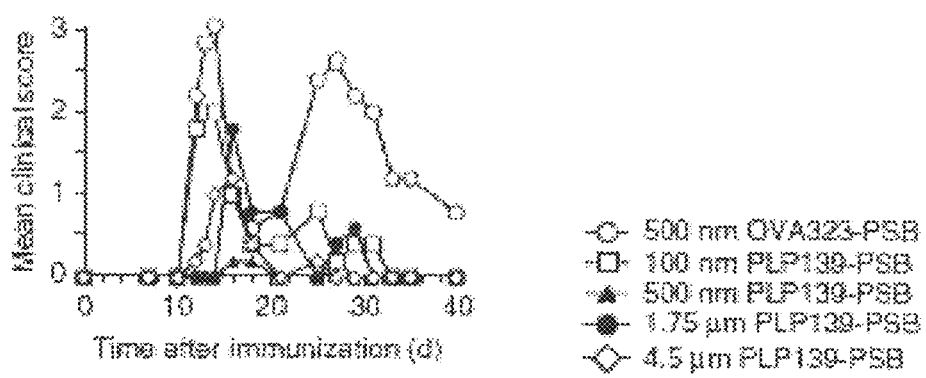
FIGS. 42A-42B demonstrate the key particle parameters required for tolerance in the EAE murine model.
Figure 42B:
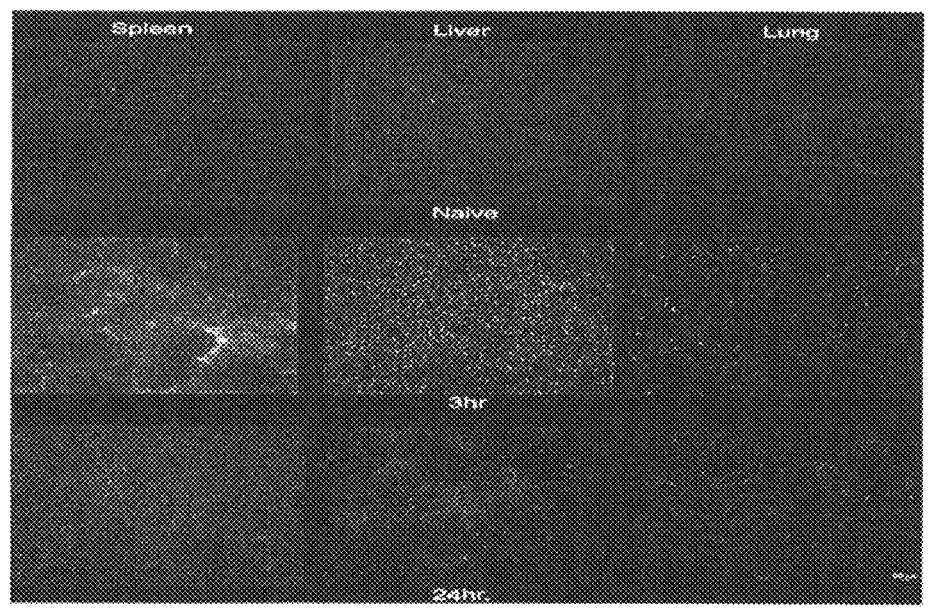

In addition to charge, the size and composition of the biodegradable TIMPs affects the induction of tolerance. As shown in FIG. 42A, the most effective particles for inducing tolerance in the EAE model are those with a mean diameter of about 500 nm. Mice were treated with either 500 nm $OVA_{323-339}$-PSB, 100 nm $PLP_{139-151}$-PSB, 500 nm $PLP_{139-151}$-PSB, 1.75 μm $PLP_{139-151}$-PSB, or 4.5 μm $PLP_{139-151}$-PSB and scored for clinical disease. PLGA carriers have slow release kinetics for over 1 month and changing the polymer ratio can impact release of the particles. Tolerance requires rapid particle uptake and clearance/degradation. Since ratios of over 50:50 lactide:glycolide slow the degradation rate, the particles of the invention in one embodiment are 50:50 lactide:glycolide. FIG. 42B shows that the particles are rapidly destroyed.

Figure 43A:
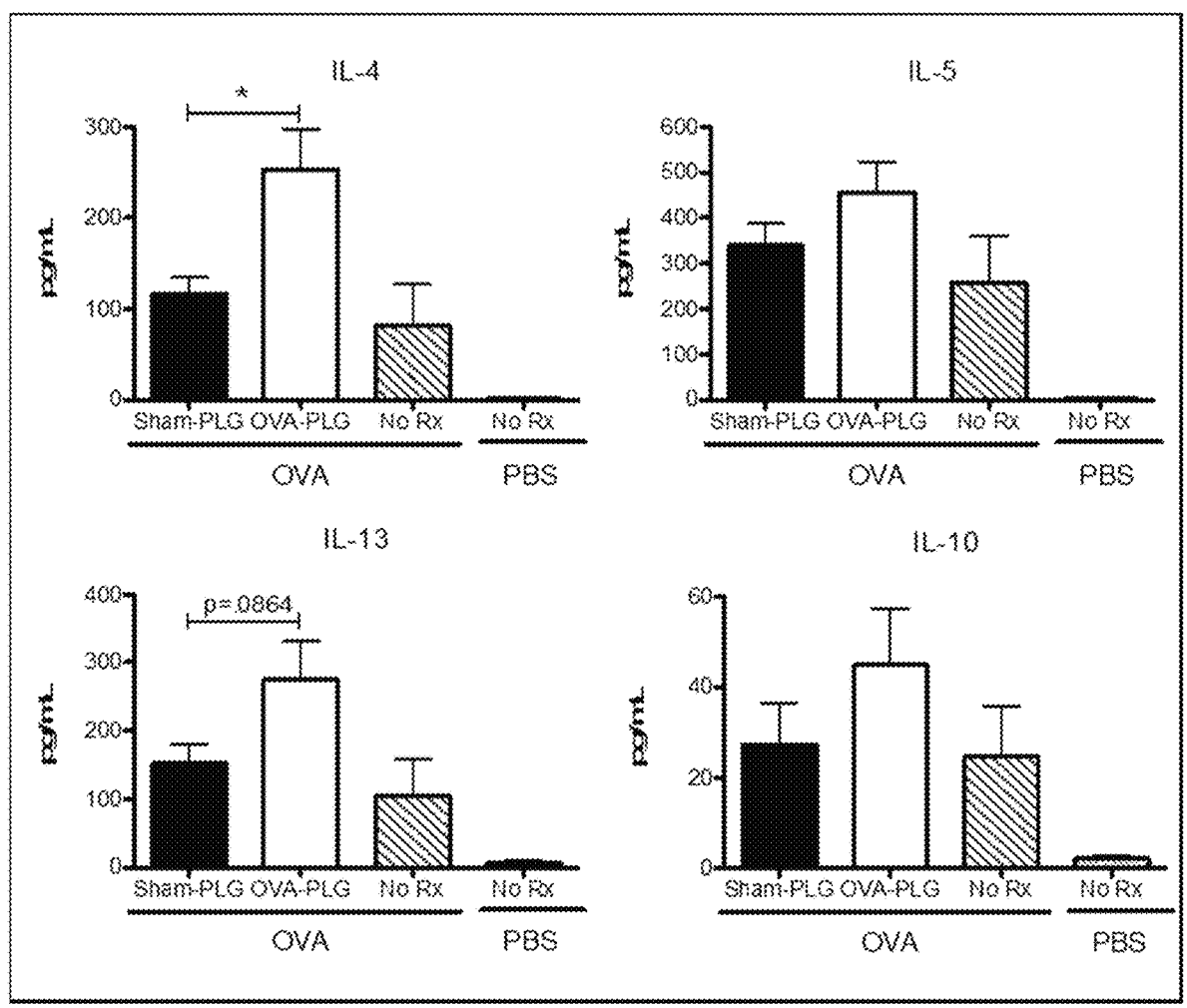
FIGS. 43A-43C demonstrate that TIMPs with encapsulated antigens are superior to peptide-coupled particles. In the murine allergy model, animals were exposed to OVA as an allergen, and were then treated with either a sham-PLG, no treatment, a PLGA particle with OVA coupled to the outside of the particle (FIG. 43A) or a PLGA particle with OVA encapsulated within the particle (TIMP) (FIG. 43B).
Figure 43B:
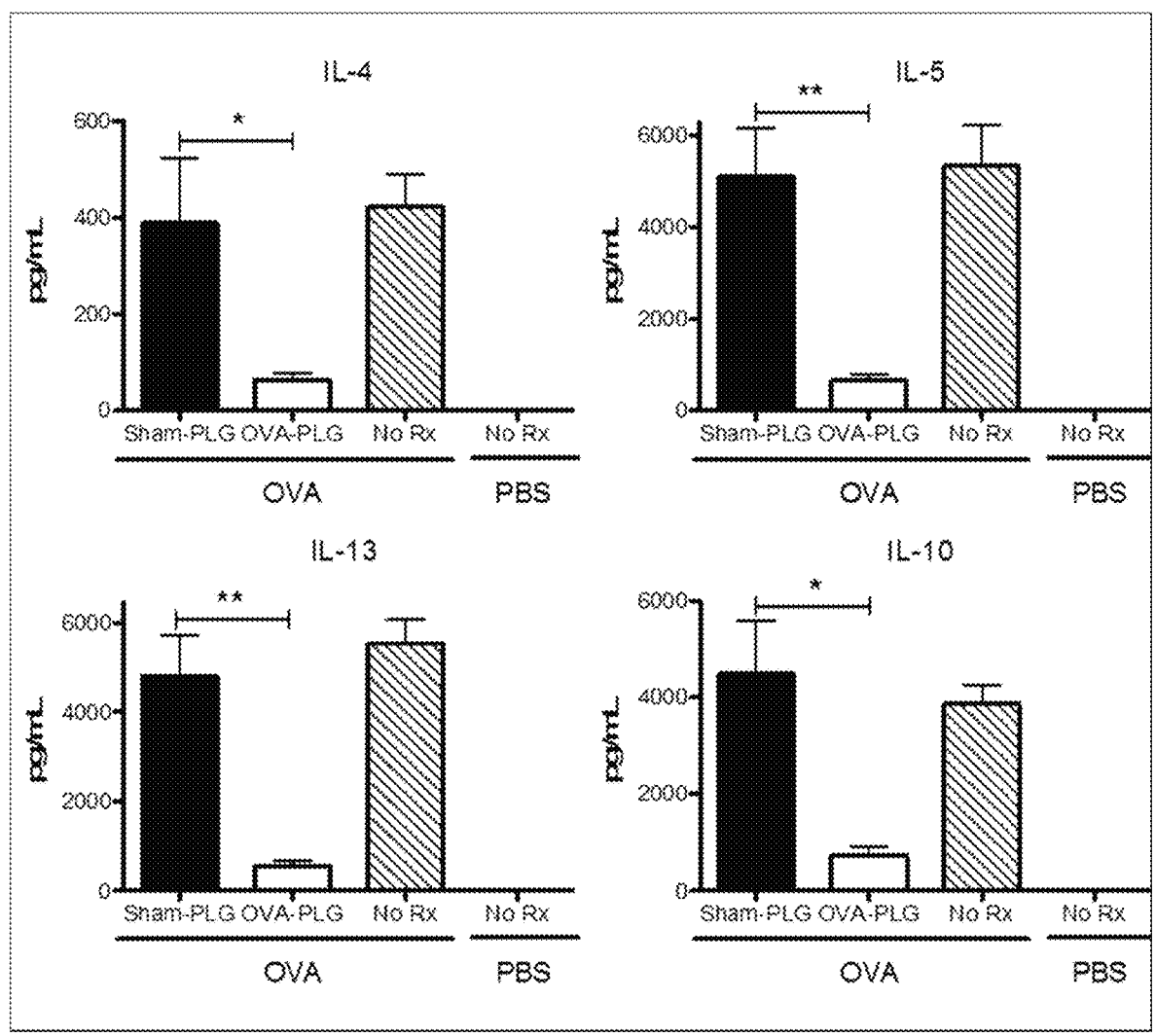
Figure 43C:
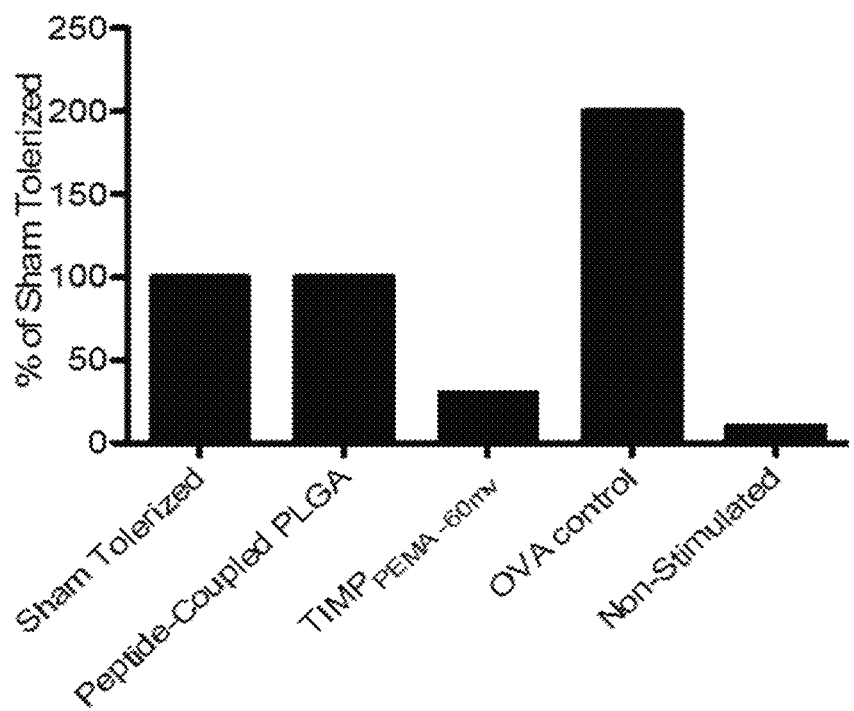

In addition to the charge and average mean diameter of the TIMPs, antigens which are encapsulated within the particle are superior to particles coupled to antigen in the allergy model. In the allergy model, coupled nanoparticles have a propensity to cause anaphylaxis and are not an effective therapy. Conversely, as shown in FIG. 43, TIMPs with a charge of −60 mv are therapeutically effective in the murine allergy model. Animals were exposed to OVA as an allergen, and were then treated with either a sham-PLG or TIMP particle, a PLG or TIMP particle with OVA, or no treatment. Panel (A) shows that OVA-PLG particles fail to reduce the TH2 response in allergy. Panel (B) shows that $TIMP_{PEMA-60mv}$ inhibit this TH2 response. Panel (C) shows that $TIMP_{PEMA-60mv}$ inhibit recall responses.

Example 24

Single-Emulsion Synthesis of Surface-Functionalized Poly (Lactide-Co-Glycolide) Particles Encapsulating Antigen Polypeptide antigens can be incorporated into poly(lactide-co-glycolide) particles using a double-emulsion process (See, Example 21), however, the present inventors have found that when incorporating more hydrophobic polypeptides, such as gliaden, it is better to incorporate the antigen into the particle with a single-emulsion process using solvents.

Poly(lactide-co-glycolide) with carboxylate end groups, a 50:50 D,L-lactide:glycolide ratio, and inherent viscosity of 0.18 dl/g in hexafluoro-2-propanol was used to create particles containing gliaden. Poly(lactide-co-glycolide) particles containing gliaden within their cores and surface-functionalized with a high density of carboxylate groups were synthesized using a single emulsion-solvent evaporation method as follows:

1. Five milligrams of gliaden and 200 mg PLG was dissolved in 50 μL of trifluoroacetic acid (TFA) and 700 μL dimethylsulphoxide and 1250 μL dichloromethane (DCM).
2. The resultant mixture was added drop-wise to 4 mL 1% w/v aqueous PEMA and sonicated for 30 seconds at 100% amplitude.
3. The resultant emulsion was poured into 200 mL of 0.5% w/v aqueous PEMA under stirring for 12 hours to allow the DCM to completely evaporate.
4. The particles were then washed three times in 0.1M sodium carbonate-sodium bicarbonate buffer pH 9.6. Alternatively, ddH$_2$O can be used to wash the particles.
5. The purified particles were resuspended in 4% w/v sucrose and 3% w/v D-mannitol in water, gradually frozen to −80° C. and lyophilized to dryness.

While specific embodiments of the invention have been described and illustrated, such embodiments should be considered illustrative of the invention only and not as limiting the invention as construed in accordance with the accompanying claims.

All patents, applications and other references cited herein are incorporated by reference in their entireties.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11129881B2). An electronic copy of the "Sequence Listing" will also be available from the USPTO upon request and payment of the fee set forth in 37 CFR 1.19(b)(3).

What is claimed is:

1. A composition comprising surface functionalized biodegradable particles comprising one or more encapsulated antigens or antigenic epitopes thereof, wherein said particles have a negative zeta potential of about −100 mV to about −30 mV, and wherein said antigen is associated with primary biliary cirrhosis (PBC).

2. The composition of claim 1, wherein said particles are poly (lactic acid) (PLA), poly (glycolic acid) (PGA), or poly (lactic co-glycolic acid) (PLGA) particles.

3. The composition of claim 1, wherein said antigen is pyruvate dehydrogenase dehydrolipoamide acetyltransferase (PCD-E2).

4. The composition of claim 1, wherein the negative zeta potential of said particles is achieved by surface functionalization.

5. The composition of claim 4, where said surface functionalization comprises carboxylation.

6. The composition of claim 1, wherein said particles are poly (lactic co-glycolic acid) (PLGA) particles.

7. The composition of claim 6, wherein the PLGA comprises a copolymer ratio of about 50:50 of polylactic acid:polyglycolic acid.

8. The composition of claim 1, wherein said particles have a zeta potential between −30 mV and −80 mV.

9. The composition of claim 1, wherein said particles have a zeta potential between −30 mV and −60 mV.

10. The composition of claim 1, wherein said particles have a diameter between 200 nm and 2000 nm.

11. The composition of claim 10, wherein said particles have a diameter between 400 nm and 800 nm.

12. The composition of claim 1 further comprising a pharmaceutically acceptable carrier or excipient.

13. The composition of claim 1 which is lyophilized.

14. A composition comprising surface functionalized biodegradable poly(lactide-co-glycolide) (PLG) particles comprising one or more encapsulated antigens or antigenic epitopes thereof, wherein said antigen is associated with primary biliary cirrhosis (PBC), wherein said PLG particles have a diameter of about 200 nm to about 2000 nm and a zeta potential of about −30 my to about −80 my.

15. A method of inducing antigen-specific tolerance in a subject comprising administering to said subject an effective amount of the composition of claim 1, wherein said subject has primary biliary cirrhosis (PBC).

16. The method of claim 15, wherein the composition is administered intravenously.

17. A method of inducing antigen-specific tolerance in a subject comprising administering to said subject an effective amount of the composition of claim 14, wherein said subject has primary biliary cirrhosis (PBC).

* * * * *

UNITED STATES PATENT AND TRADEMARK OFFICE
CERTIFICATE OF CORRECTION

PATENT NO. : 11,129,881 B2  
APPLICATION NO. : 16/847450  
DATED : September 28, 2021  
INVENTOR(S) : Lonnie D. Shea et al.

Page 1 of 1

It is certified that error appears in the above-identified patent and that said Letters Patent is hereby corrected as shown below:

In the Claims

At Column 69, Line 38, "dehydrolipoamide" should be -- dihydrolipoamide --.

At Column 69, Line 43, "where" should be -- wherein --.

At Column 70, Line 32, "comprising" should be -- comprises --.

At Column 70, Line 42, "-30 my to about -80 my." should be -- -30 mV to about -80 mV. --.

Signed and Sealed this
Twenty-second Day of February, 2022

Drew Hirshfeld
*Performing the Functions and Duties of the*
*Under Secretary of Commerce for Intellectual Property and*
*Director of the United States Patent and Trademark Office*